US010172821B2

(12) United States Patent
Bradner et al.

(10) Patent No.: US 10,172,821 B2
(45) Date of Patent: *Jan. 8, 2019

(54) HISTONE DEACETYLASE INHIBITORS

(71) Applicants: President & Fellows of Harvard College, Cambridge, MA (US); Dana-Farber Cancer Institute, Inc., Boston, MA (US)

(72) Inventors: James Elliot Bradner, Cambridge, MA (US); Ralph Mazitschek, Arlington, MA (US)

(73) Assignee: President & Fellows of Harvard College Dana-Farber Cancer Institute, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,078

(22) Filed: Jun. 29, 2017

(65) Prior Publication Data
US 2017/0360740 A1 Dec. 21, 2017

Related U.S. Application Data

(63) Continuation of application No. 14/862,679, filed on Sep. 23, 2015, now Pat. No. 9,724,321, which is a continuation of application No. 14/198,764, filed on Mar. 6, 2014, now Pat. No. 9,199,923, which is a continuation of application No. 13/944,320, filed on Jul. 17, 2013, which is a continuation of application No. 13/678,983, filed on Nov. 16, 2012, which is a continuation of application No. 12/279,398, filed as application No. PCT/US2007/062152 on Feb. 14, 2007, now Pat. No. 8,383,855.

(60) Provisional application No. 60/773,172, filed on Feb. 14, 2006.

(51) Int. Cl.
| A61K 31/165 | (2006.01) |
| A61K 31/231 | (2006.01) |
| A61K 31/337 | (2006.01) |
| C07C 259/06 | (2006.01) |
| C07D 413/12 | (2006.01) |
| C07C 235/78 | (2006.01) |
| C07D 319/06 | (2006.01) |
| A61K 9/00 | (2006.01) |

(52) U.S. Cl.
CPC .......... *A61K 31/231* (2013.01); *A61K 9/0014* (2013.01); *A61K 31/165* (2013.01); *A61K 31/337* (2013.01); *C07C 235/78* (2013.01); *C07C 259/06* (2013.01); *C07D 319/06* (2013.01); *C07D 413/12* (2013.01)

(58) Field of Classification Search
CPC .................................................. A61K 31/165
See application file for complete search history.

(56) References Cited

U.S. PATENT DOCUMENTS

| 4,631,211 | A | 12/1986 | Houghten |
| 4,639,462 | A | 1/1987 | Kramer et al. |
| 5,045,538 | A | 9/1991 | Schneider et al. |
| 5,059,698 | A | 10/1991 | Schulthess et al. |
| 5,096,815 | A | 3/1992 | Ladner et al. |
| 5,143,854 | A | 9/1992 | Pirrung et al. |
| 5,198,346 | A | 3/1993 | Ladner et al. |
| 5,223,409 | A | 6/1993 | Ladner et al. |
| 5,225,173 | A | 7/1993 | Wai |
| 5,238,781 | A | 8/1993 | Schadeli |
| 5,288,514 | A | 2/1994 | Ellman |
| 5,304,121 | A | 4/1994 | Sahatjian |
| 5,359,115 | A | 10/1994 | Campbell et al. |
| 5,362,899 | A | 11/1994 | Campbell |
| 5,393,741 | A | 2/1995 | Pettersen et al. |
| 5,440,016 | A | 8/1995 | Blondelle et al. |
| 5,480,971 | A | 1/1996 | Houghten et al. |
| 5,659,016 | A | 8/1997 | Nakamura et al. |
| 5,763,182 | A | 6/1998 | Nakamura et al. |
| 5,837,313 | A | 11/1998 | Ding et al. |
| 5,886,026 | A | 3/1999 | Hunter et al. |
| 5,891,507 | A | 4/1999 | Jayaraman |

(Continued)

FOREIGN PATENT DOCUMENTS

DE 32422252 1/1987
EP 0322335 A1 6/1989

(Continued)

OTHER PUBLICATIONS

Brachman et al., The SIR2 gene family, conserved from bacteria to humans, functions in silencing, cell cycle progression, and chromosome stability. Genes Dev. Dec. 1, 1995;9(23):2888-902.

(Continued)

*Primary Examiner* — James D. Anderson
(74) *Attorney, Agent, or Firm* — McCarter & English, LLP; Elizabeth A. Hanley; Michael J. DeGrazia

(57) ABSTRACT

In recognition of the need to develop novel therapeutic agents, the present invention provides novel histone deacetylase inhibitors. These compounds include an ester bond making them sensitive to deactivation by esterases. Therefore, these compounds are particularly useful in the treatment of skin disorders. When the compounds reaches the bloodstream, an esterase or an enzyme with esterase activity cleaves the compound into biologically inactive fragments or fragments with greatly reduced activity Ideally these degradation products exhibit a short serum and/or systemic half-life and are eliminated rapidly. These compounds and pharmaceutical compositions thereof are particularly useful in treating cutaneous T-cell lymphoma, neurofibromatosis, psoriasis, hair loss, skin pigmentation, and dermatitis, for example. The present invention also provides methods for preparing compounds of the invention and intermediates thereto.

12 Claims, 15 Drawing Sheets

(56) References Cited

U.S. PATENT DOCUMENTS

Figure 2:
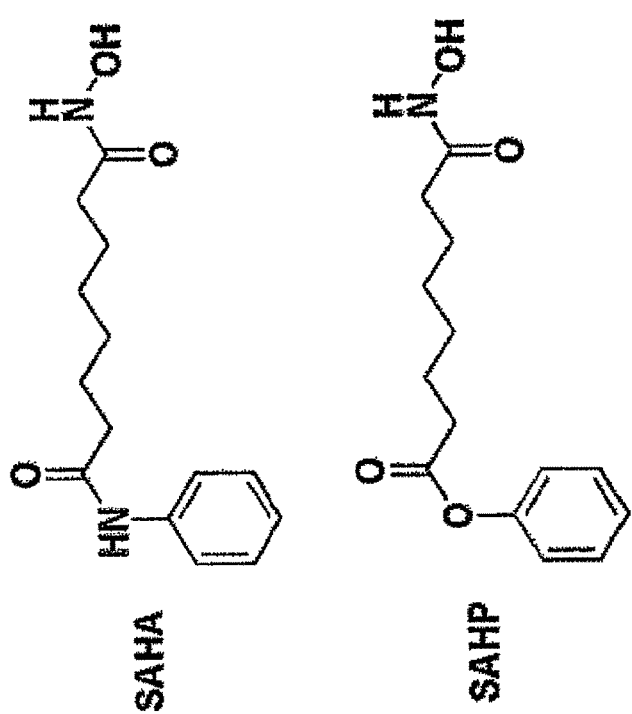
Figure 3:
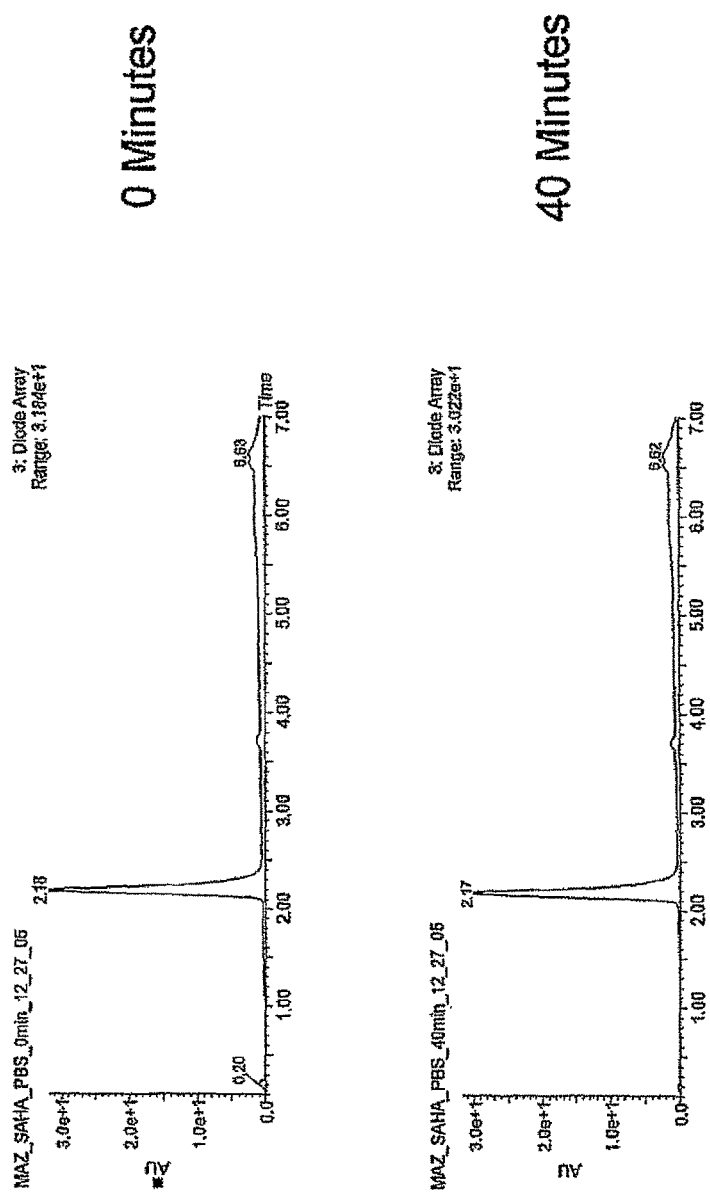
Figure 4:
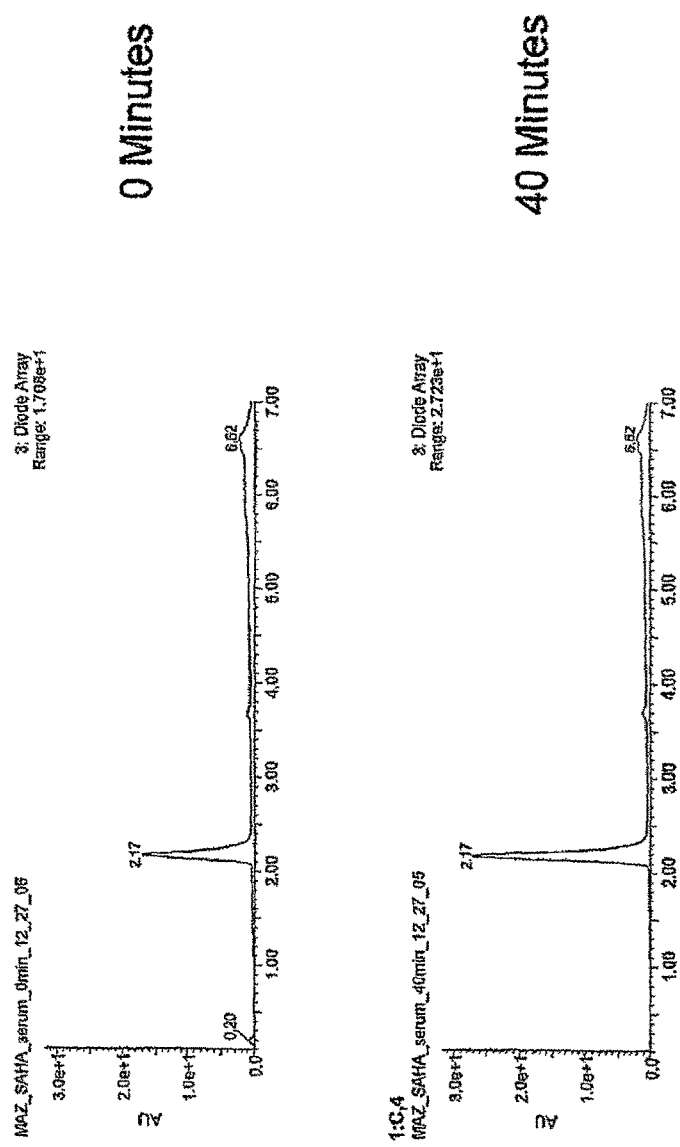
Figure 5:
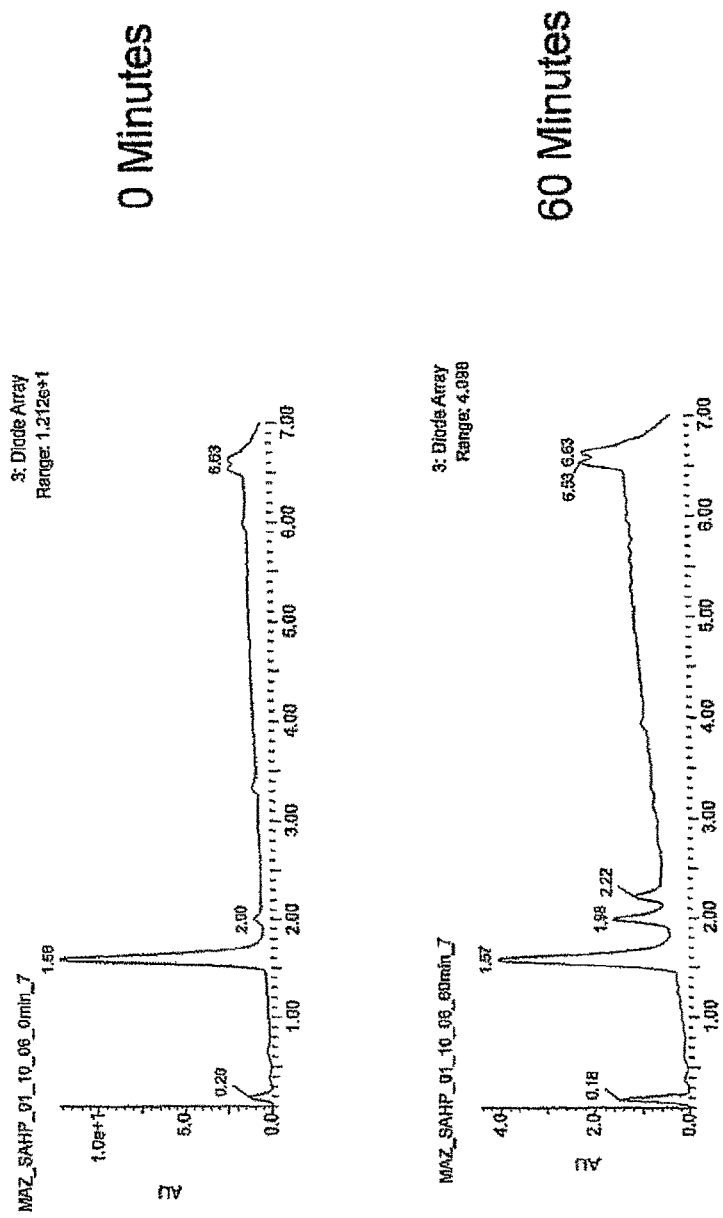
Figure 6:
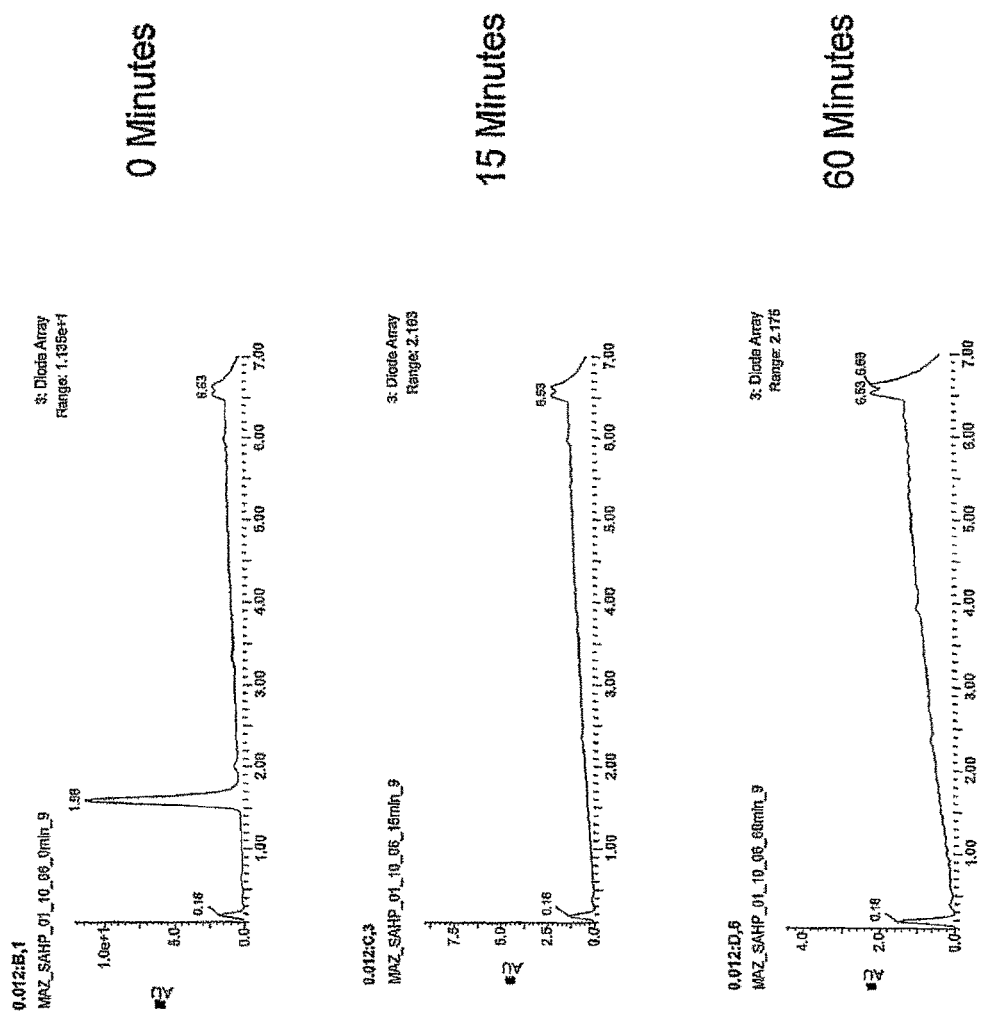
Figure 7:
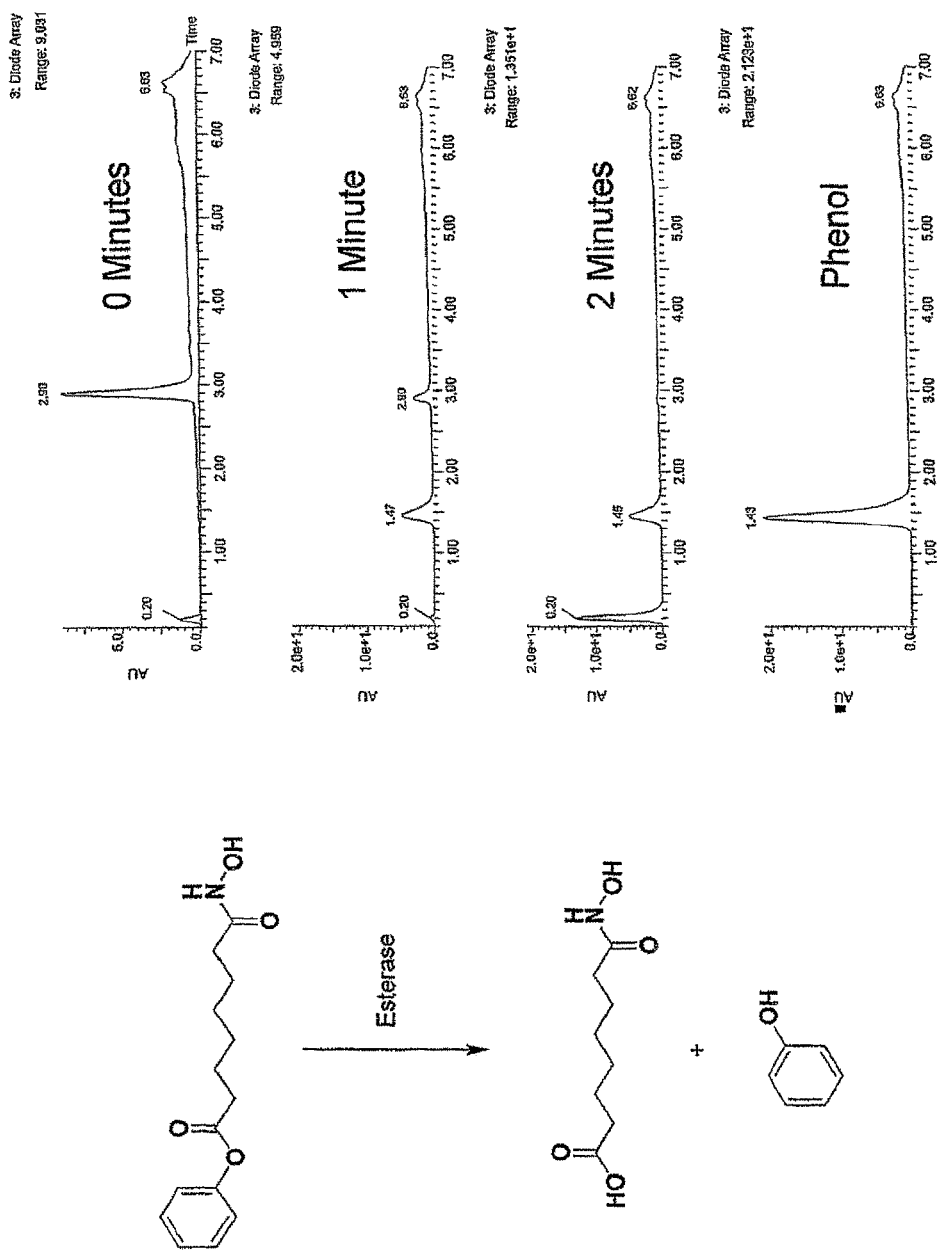
Figure 8:
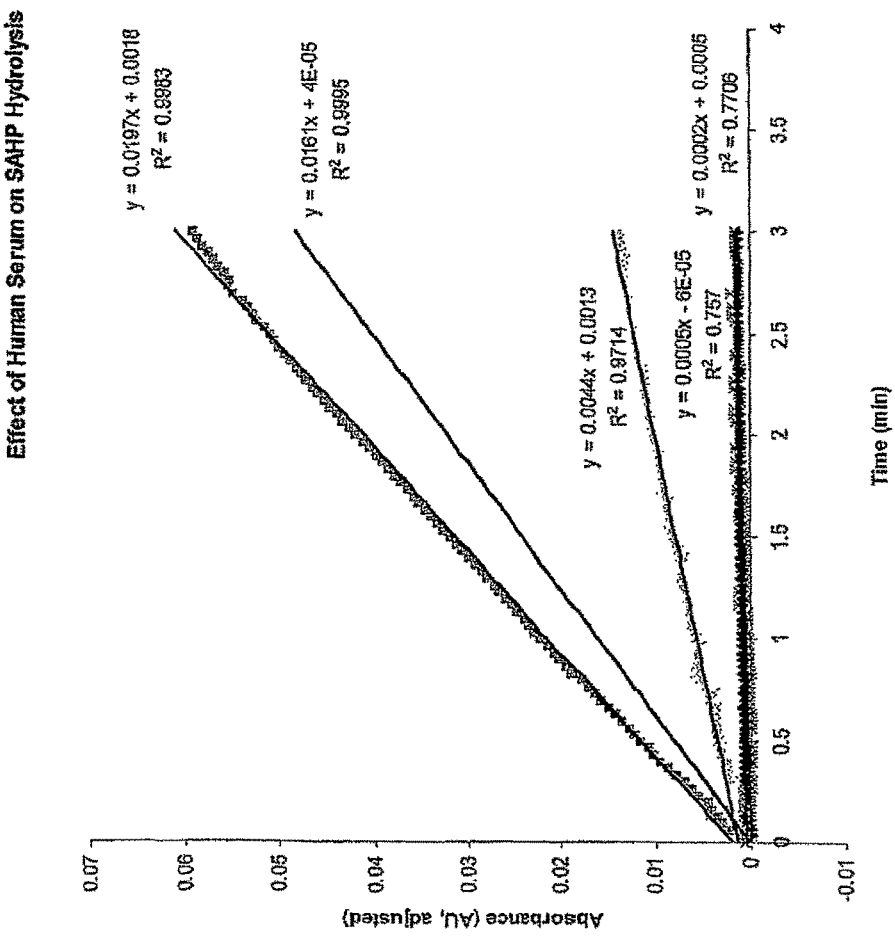
Figure 9:
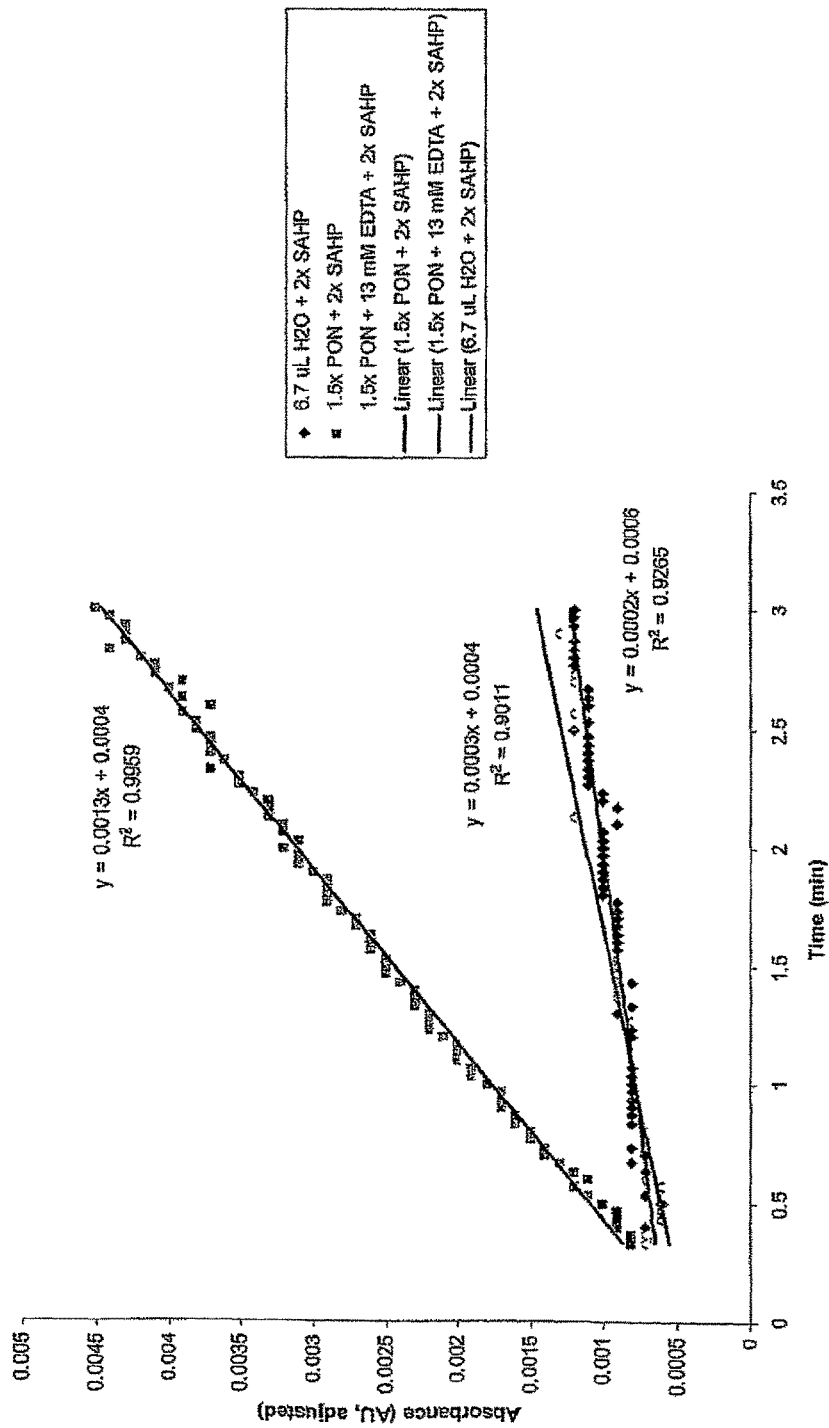
Figure 10:
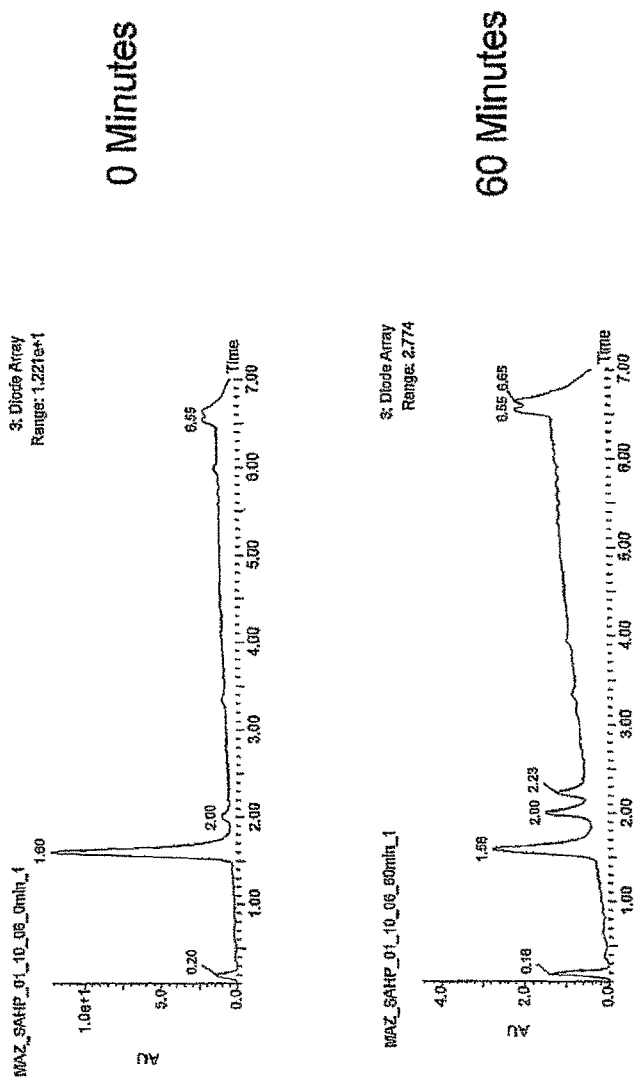
Figure 11:
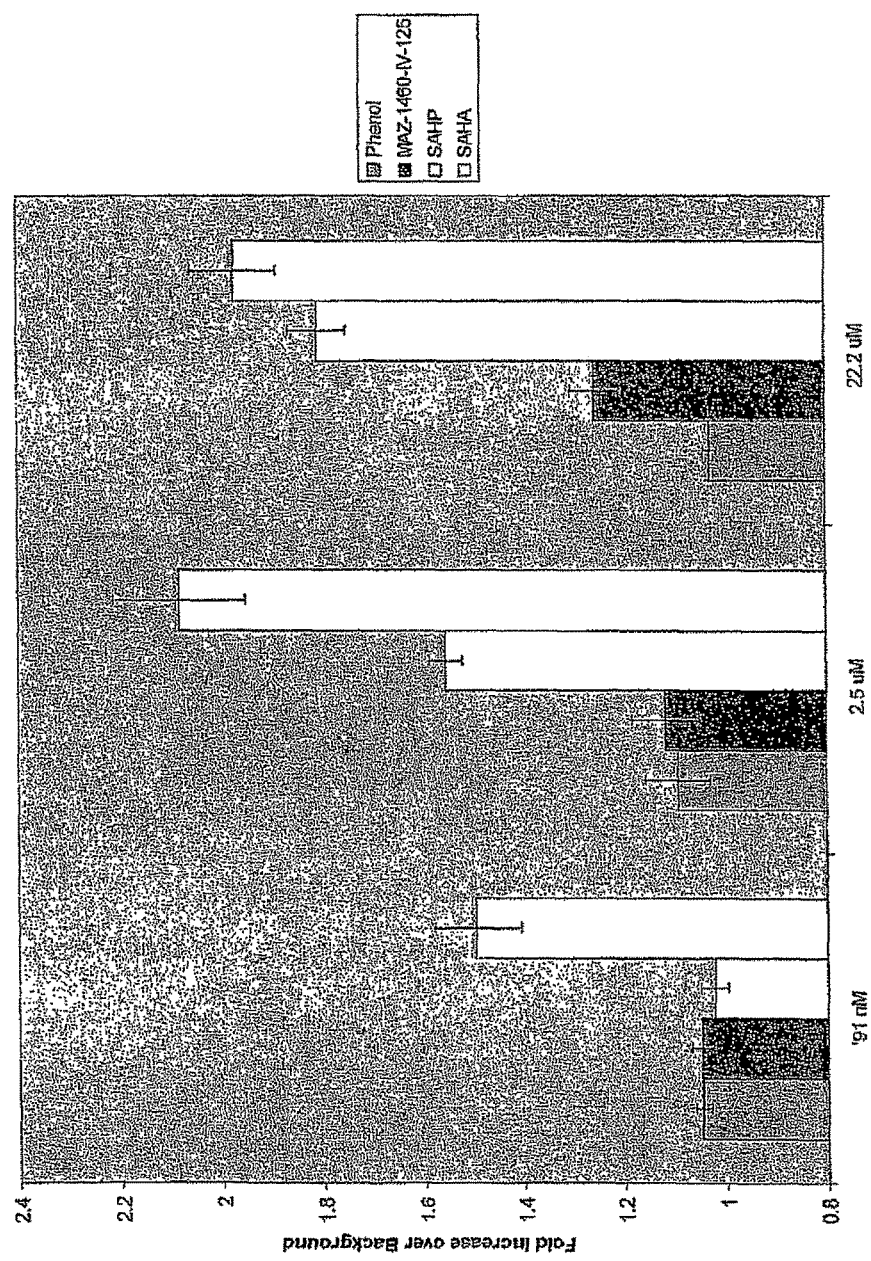

| | | | |
|---|---|---|---|
| 6,030,945 A | 2/2000 | Ashkenazi | |
| 6,068,987 A | 5/2000 | Dulski et al. | |
| 6,071,305 A | 6/2000 | Brown et al. | |
| 6,099,562 A | 8/2000 | Ding et al. | |
| 6,153,252 A | 11/2000 | Hossainy et al. | |
| 6,190,619 B1 | 2/2001 | Kilcoin et al. | |
| 6,195,612 B1 | 2/2001 | Pack-Harris | |
| 6,203,551 B1 | 3/2001 | Wu | |
| 6,231,600 B1 | 5/2001 | Zhong | |
| 6,248,127 B1 | 6/2001 | Shah et al. | |
| 6,251,136 B1 | 6/2001 | Guruwaiya et al. | |
| 6,258,121 B1 | 7/2001 | Yang et al. | |
| 6,273,913 B1 | 8/2001 | Wright et al. | |
| 6,428,960 B1 | 8/2002 | Clark et al. | |
| 6,495,719 B2 | 12/2002 | Lan-Hargest et al. | |
| 6,512,123 B2 | 1/2003 | Grossmann et al. | |
| 6,517,889 B1 | 2/2003 | Jayaraman | |
| 6,541,661 B1 | 4/2003 | Delorme et al. | |
| RE38,506 E | 4/2004 | Breslow et al. | |
| 6,777,217 B1 | 8/2004 | Schreiber et al. | |
| 6,897,220 B2 | 5/2005 | Delorme et al. | |
| 6,960,685 B2 | 11/2005 | Watkins et al. | |
| 7,244,853 B2 | 7/2007 | Schreiber et al. | |
| 7,250,504 B2 | 7/2007 | Grozinger et al. | |
| 7,737,172 B2 | 6/2010 | Halperin et al. | |
| 8,383,855 B2 | 2/2013 | Bradner et al. | |
| 9,199,923 B2 | 12/2015 | Bradner et al. | |
| 9,724,321 B2 * | 8/2017 | Bradner | A61K 31/231 |
| 2001/0027340 A1 | 10/2001 | Wright et al. | |
| 2003/0004209 A1 | 1/2003 | Hunter et al. | |
| 2003/0187027 A1 | 10/2003 | Schreiber et al. | |
| 2004/0072849 A1 | 4/2004 | Schreiber et al. | |
| 2004/0087631 A1 | 5/2004 | Bacopoulos et al. | |
| 2004/0092598 A1 | 5/2004 | Watkins et al. | |
| 2004/0127522 A1 | 7/2004 | Chiao et al. | |
| 2004/0138153 A1 | 7/2004 | Ramesh et al. | |
| 2005/0267037 A1 | 12/2005 | Anderson et al. | |
| 2005/0287629 A1 | 12/2005 | Grozinger et al. | |
| 2006/0020131 A1 | 1/2006 | Raeppel et al. | |
| 2006/0079528 A1 | 4/2006 | Finn et al. | |
| 2006/0239909 A1 | 10/2006 | Anderson et al. | |
| 2007/0093413 A1 | 4/2007 | Schreiber et al. | |
| 2008/0269245 A1 | 10/2008 | Schreiber et al. | |
| 2008/0300205 A1 | 12/2008 | Tsai et al. | |
| 2009/0036318 A1 | 2/2009 | Grozinger et al. | |
| 2009/0209590 A1 | 8/2009 | Mazitschek et al. | |
| 2009/0221474 A1 | 9/2009 | Schreiber et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |

FOREIGN PATENT DOCUMENTS

| | | |
|---|---|---|
| EP | 0331524 A2 | 9/1989 |
| EP | 0708112 A1 | 4/1996 |
| JP | 8311321 | 11/1996 |
| JP | 9124918 | 5/1997 |
| JP | 2003509343 A | 3/2003 |
| WO | 9107087 A1 | 5/1991 |
| WO | 9210092 A1 | 6/1992 |
| WO | 9307867 A1 | 4/1993 |
| WO | 9309668 A1 | 5/1993 |
| WO | 9320242 A1 | 10/1993 |
| WO | 9408051 A1 | 4/1994 |
| WO | 9711366 A1 | 3/1997 |
| WO | 9735990 A2 | 10/1997 |
| WO | 9816830 A2 | 4/1998 |
| WO | 9847869 A1 | 10/1998 |
| WO | 0020415 A1 | 4/2000 |
| WO | 0034313 A1 | 6/2000 |
| WO | 0035911 A1 | 6/2000 |
| WO | 0036132 A1 | 6/2000 |
| WO | 0044709 A2 | 8/2000 |
| WO | 0118171 A2 | 3/2001 |
| WO | 02089782 A2 | 11/2002 |
| WO | 04001059 A2 | 12/2003 |
| WO | 2004046104 A2 | 6/2004 |
| WO | 2004103369 A1 | 12/2004 |
| WO | 2005007091 A2 | 1/2005 |
| WO | 2005012247 A1 | 2/2005 |
| WO | 2005018578 A2 | 3/2005 |
| WO | 2005066151 A2 | 7/2005 |
| WO | 2005080335 A1 | 9/2005 |
| WO | 2006006080 A2 | 1/2006 |
| WO | 2006060676 A1 | 6/2006 |
| WO | 2006060809 A2 | 6/2006 |

OTHER PUBLICATIONS

Bradley et al., Formation of germ-line chimaeras from embryo-derived teratocarcinoma cell lines. Nature. May 17-23, 1984;309(5965):255-6.

Branden et al., Chapter 16. Prediction, Engineering, and Design of Protein Structures. In: Introduction to Protein Structure. Garland Publishing Inc., New York. 1991:247.

Braunstein et al., Transcriptional silencing in yeast is associated with reduced nucleosome acetylation. Genes Dev. Apr. 1993;7(4):592-604.

Braunstein et al., Efficient transcriptional silencing in *Saccharomyces cerevisiae* requires a heterochromatin histone acetylation pattern. Mol Cell Biol. Aug. 1996;16(8):4349-56.

Bray et al., Gas Phase Cleavage of Peptides from a Solid Support with Ammonia Vapour. Application in Simultaneous Multiple Peptide Synthesis. Tetrahedron Lett. 1991;32:6163-66.

Bray et al., The Simultaneous Multiple Production of Solution Phase Peptides; Assessment of the Geysen Method of Simultaneous Peptide Synthesis. Tetrahedron Lett 1990;31:5811-14.

Brenner et al., Encoded combinatorial chemistry. Proc Natl Acad Sci U S A. Jun. 15, 1992;89(12):5381-3.

Brinster et al., Factors affecting the efficiency of introducing foreign DNA into mice by microinjecting eggs. Proc Natl Acad Sci U S A. Jul. 1985;82(13):4438-42.

Brownell et al., Tetrahymena histone acetyltransferase A: a homolog to yeast Gcn5p linking histone acetylation to gene activation. Cell. Mar. 22, 1996;84(6):843-51.

Brunet et al., Nuclear translocation of p42/p44 mitogen-activated protein kinase is required for growth factor-induced gene expression and cell cycle entry. EMBO J. Feb. 1, 1999;18(3):664-74.

Burbaum et al., A paradigm for drug discovery employing encoded combinatorial libraries. Proc Natl Acad Sci U S A. Jun. 20, 1995;92(13):6027-31.

Burbelo et al., 14-3-3 proteins. Hot numbers in signal transduction. Curr Biol. Feb. 1, 1995;5(2):95-6.

Byrd et al., Depsipeptide (FR901228): a novel therapeutic agent with selective, in vitro activity against human B-cell chronic lymphocytic leukemia cells. Blood. Aug. 15, 1999;94(4):1401-8.

Cali et al., Nucleotide sequence of a cDNA encoding the human muscle-specific enolase (MSE). Nucleic Acids Res. Apr. 11, 1990;18(7):1893.

Cameron et al., Recent advances in transgenic technology. Mol Biotechnol. Jun. 1997;7(3):253-65.

Carmen et al., HDA1 and HDA3 are components of a yeast histone deacetylase (HDA) complex. J Biol Chem. Jun. 28, 1996;271(26):15837-44.

Cavenee et al., Expression of recessive alleles by chromosomal mechanisms in retinoblastoma. Nature. Oct. 27-Nov. 2, 1983;305(5937):779-84.

Chen et al., "Analogous" Organic Synthesis of Small-Compound Libraries: Validation of Combinatorial Chemistry in Small-Molecule Synthesis. JACS. 1994;116:2661-62.

Clipstone et al., Identification of calcineurin as a key signalling enzyme in T-lymphocyte activation. Nature. Jun. 25, 1992;357(6380):695-7.

Cockell et al., Nuclear compartments and gene regulation. Curr Opin Genet Dev. Apr. 1999;9(2):199-205.

Csordas, On the biological role of histone acetylation. Biochem J. Jan. 1, 1990;265(1):23-38.

(56) References Cited

OTHER PUBLICATIONS

Cuperus et al., Locus specificity determinants in the multifunctional yeast silencing protein Sir2. EMBO J. Jun. 1, 2000;19(11):2641-51.
Cwirla et al., Peptides on phage: a vast library of peptides for identifying ligands. Proc Natl Acad Sci U S A. Aug. 1990;87(16):6378-82.
Dangond et al., Differential display cloning of a novel human histone deacetylase (HDAC3) cDNA from PHA-activated immune cells. Biochem Biophys Res Commun. Jan. 26, 1998;242(3):648-52.
Dann et al., Human renin: a new class of inhibitors. Biochem Biophys Res Commun. Jan. 14, 1986;134(1):71-7.
David et al., Histone deacetylase associated with mSin3A mediates repression by the acute promyelocytic leukemia-associated PLZF protein. Oncogene. May 14, 1998;16(19):2549-56.
Davie et al., Multiple functions of dynamic histone acetylation. J Cell Biochem. May 1994;55(1):98-105.
Delgrave et al., Recursive ensemble mutagenesis. Protein Engineer. 1993;6(3):327-31.
Devlin et al., Random peptide libraries: a source of specific protein binding molecules. Science Jul. 27, 1990;249 (4967):404-6.
Dower et al., Chapter 28. The Search for Molecular Diversity (II): Recombinant and Synthetic Randomized Peptide Libraries. Annu Rep Med Chem. 1991;26:271-80.
Emiliani et al., Characterization of a human RPD3 ortholog, HDAC3. Proc Natl Acad Sci U S A. Mar. 17, 1998;95 (6):2795-800.
Evans et al., Establishment in culture of pluripotential cells from mouse embryos. Nature. Jul. 9, 1981;292(5819):154-6.
Ewenson et al., Ketomethylene pseudopeptide analogues of substance P: synthesis and biological activity. J Med Chem. Feb. 1986;29(2):295-9.
Felsenfeld, Chromatin as an essential part of the transcriptional mechanism. Nature. Jan. 16, 1992;355(6357):219-24.
Feng et al., Progressive sequence alignment as a prerequisite to correct phylogenetic trees. J Mol Evol. 1987;25 (4):351-60.
Finnin et al., Structures of a histone deacetylase homologue bound to the TSA and SAHA inhibitors. Nature. Sep. 9, 1999;401(6749):188-93.
Fischle et al., A new family of human histone deacetylases related to *Saccharomyces cerevisiae* HDA1p. J Biol Chem. Apr. 23, 1999;274(17):11713-20.
Fitch et al., Distinguishing Homologous from Analogous Proteins. Syst Zool. 1970;19:99-113.
Fleming et al., The total synthesis of ( )-trichostatin A: Some observations on the acylation and alkylation of silyl enol others, silyl dienol ethers and a silyl trienol ether. Tetrahedron. 1983;39:841-46.
Fodor et al., Light-directed, spatially addressable parallel chemical synthesis. Science. Feb. 15, 1991;251 (4995):767-73.
Friend et al., Deletions of a DNA sequence in retinoblastomas and mesenchymal tumors: organization of the sequence and its encoded protein. Proc Natl Acad Sci U S A. Dec. 1987;84(24):9059-63.
Frye, Phylogenetic classification of prokaryotic and eukaryotic Sir2-like proteins. Biochem Biophys Res Commun. Jul. 5, 2000;273(2):793-8.
Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79. cited byapplicant.
Furukawa et al., Isolation and mapping of a human gene (RPD3L1) that is homologous to RPD3, a transcription factor in *Saccharomyces cerevisiae*. Cytogenet Cell Genet 1996;73(1-2):130-3.
Furumai et al., Potent histone deacetylase inhibitors built from trichostatin A and cyclic tetrapeptide antibiotics including rapoxin. Proc Natl Acad Sci U S A. Jan. 2, 2001;98(1):87-92.
Gallop et al., Applications of combinatorial technologies to drug discovery. 1. Background and peptide combinatorial libraries. J Med Chem. Apr. 29, 1994;37(9):1233-51.
Garcia-Ramirez et al., Role of the histone "tails" in the folding of oligonucleosomes depleted of histone H1. J Biol Chem. Sep. 25, 1992;267(27):19587-95.
Gardlik et al., Vectors and delivery systems in gene therapy. Med Sci Monit. Apr. 2005;11(4):RA110-21. Epub Mar. 24, 2005.
Gartenberg, The Sir proteins of *Saccharomyces cerevisiae*: mediators of transcriptional silencing and much more. Curr Opin Microbiol. Apr. 2000;3(2):132-7.
Office Communication, dated Oct. 16, 2002, for U.S. Appl. No. 08/624,735.
Office Communication, dated Aug. 12, 2003, for U.S. Appl. No. 08/624,735.
Notice of Allowance, dated Apr. 13, 2004, for U.S. Appl. No. 08/624,735.
Office Communication, dated May 6, 2009, for U.S. Appl. No. 10/919,217.
Office Communication, dated Mar. 4, 2010, for U.S. Appl. No. 10/919,217.
Office Communication, dated Oct. 14, 2010, for U.S. Appl. No. 10/919,217.
Office Communication, dated Apr. 8, 2010, for U.S. Appl. No. 12/196,878.
Office Communication, dated Aug. 10, 2010, for U.S. Appl. No. 12/196,878.
Office Communication, dated Aug. 5, 2010, for U.S. Appl. No. 12/196,946.
Office Communication, dated Jun. 30, 2003, for U.S. Appl. No. 09/800,187.
Office Communication, dated Apr. 13, 2004, for U.S. Appl. No. 09/800,187.
Notice of Allowance, dated Apr. 13, 2007, for U.S. Appl. No. 10/964,313.
Office Communication, dated Sep. 17, 2009, for U.S. Appl. No. 11/831,303.
Office Communication, dated Apr. 2, 2010, for U.S. Appl. No. 12/370,390.
Office Communication, dated Oct. 8, 2010, for U.S. Appl. No. 12/370,390.
GenBank Submission: NIH/NCBI, Accession No. AAA68286; GI: 348052, Henkin et al., Jun. 1995.
GenBank Submission; NIH/NCBI, Accession No. AB006626; GI:6635126, Ohara et al.; Dec. 25, 1999.
GenBank Submission; NIH/NCBI, Accession No. AB006626; GI:2564323, Ohara et al.; Mar. 18, 1998.
GenBank Submission; NIH/NCBI, Accession No. AJ011972, Strom et al.; Oct. 19, 1998.
GenBank Submission; NIH/NCBI, Accession No. AF039241, Swensen.; Mar. 11, 2009.
GenBank Submission: NIH/NCBI, Accession No. BAA25526; GI: 3043724, Ohara et al., Apr. 10, 1998.
GenBank Submission; NIH/NCBI, Accession No. CAA09893.1, Strom et al.; Oct. 7, 2008.
GenBank Submission; NIH/NCBI, Accession No. NM.sub.-0060442, Dhakal et al.; Mar. 15, 2009.
GenBank Submission; NIH/NCBI, Accession No. NM.sub.-001015053.1, Seo et al.; Mar. 15, 2009.
GenBank Submission; NIH/NCBI, Accession No. NM.sub.-0060373, Chabane et al.; Mar. 29, 2009.
GenBank Submission: NIH/NCBI, Accession No. P56524; GI: 3024889, Ohara et al., Dec. 15, 1998.
GenBank Submission; NIH/NCBI, Accession No. R64669, Wilson; May 26, 1995.
GenBank Submission; NIH/NCBI, Accession No. U31814, Yang et al.; Nov. 14, 1996.
GenBank Submission: NIH/NCBI, Accession No. Q48935; GI: 3023317, Sakurada et al., Apr. 20, 2010.
GenBank Submission; NIH/NCBI, Accession No. Q9Z2V5, Verdel et al.; Mar. 2, 2010.
GenBank Submission; NIH/NCBI, Accession No. Q9Z2V6, Verdel et al.; Mar. 2, 2010.
NCBI annotation project, GenBank Accession No. XM.sub.-002252, Oct. 2001.

(56) References Cited

OTHER PUBLICATIONS

NCBI annotation project, GenBank Accession No. XM.sub.-004963, Feb. 2001.
NCBI annotation project, GenBank Accession No. XM.sub.-0049632, Oct. 2001.
NCBI annotation project, GenBank Accession No. XM.sub.-007047, Nov. 2000.
NCBI annotation project, GenBank Accession No. XM.sub.-008359, Oct. 2001.
NCBI annotation project, GenBank Accession No. XP.sub.-002252, Oct. 2001.
NCBI annotation project, GenBank Accession No. XP.sub.-008359.2, Feb. 2001.
Adams et al., Initial assessment of human gene diversity and expression patterns based upon 83 million nucleotides of cDNA sequence. Nature. Sep. 28, 1995;377(6547 Suppl):3-174.
Afshar et al., Characterization of a human gene with sequence homology to Saccharomyces cerevisiae SIR2. Gene. Jun. 24, 1999;234(1):161-8.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Aparicio et al., Modifiers of position effect are shared between telomeric and silent mating-type loci in S. cerevisiae. Cell. Sep. 20, 1991;66(6):1279-87.
Arkin et al., An algorithm for protein engineering: simulations of recursive ensemble mutagenesis. Proc Natl Acad Sci U S A. Aug. 15, 1992;89(16):7811-5.
Auffray et al., [Image: molecular integration of the analysis of the human genome and its expression.] C R Acad Sci III. Feb. 1995;318(2):263-72. French.
Baer et al., Eukaryotic RNA polymerase II binds to nucleosome cores from transcribed genes. Nature. Feb. 10, 1983;301(5900):482-8.
Ballestar et al., Methyl-CpG-binding proteins. Targeting specific gene repression. Eur J Biochem. Jan. 2001;268(1):1-6.
Bernstein et al., Genomewide studies of histone deacetylase function in yeast. Proc Natl Acad Sci U S A. Dec. 5, 2000;97(25):13708-13.
Blondelle et al., Soluble combinatorial libraries of organic, peptidomimetic and peptide diversities. Trends Anal Chem. 1995;14:83-92.
Bowdish et al., Analysis of RIM11, a yeast protein kinase that phosphorylates the meiotic activator IME1. Mol Cell Biol. Dec. 1994;14(12):7909-19.
Robertson et al., Germ-line transmission of genes introduced into cultured pluripotential cells by retroviral vector. Nature. Oct. 2-8, 1986;323(6087):445-8.
Rudinger, Characteristics of the amino acids as components of a peptide hormone sequence. In: Peptide Hormones. J. A. Parsons, ed. University Park Press, Baltimore, MD. 1976;1-7.
Rundlett et al., HDA1 and RPD3 are members of distinct yeast histone deacetylase complexes that regulate silencing and transcription. Proc Natl Acad Sci U S A. Dec. 10, 1996;93(25):14503-8.
Sanchez Del Pino et al., Properties of the yeast nuclear histone deacetylase. Biochem J. Nov. 1, 1994;303 ( Pt 3):723-9.
Sasaki et al., Ligand-induced recruitment of a histone deacetylase in the negative-feedback regulation of the thyrotropin beta gene. EMBO J. Oct. 1, 1999;18(19):5389-98.
Sato et al., Synthesis and Antibiotic Activity of a Gramicidin S Analogue containing Bicyclic .beta.-Turn Dipeptides. J Chem Soc Perkin Trans. 1986;1:1231-34.
Sawa et al., Histone deacetylase inhibitors such as sodium butyrate and trichostatin A induce apoptosis through an increase of the bcl-2-related protein Bad. Brain Tumor Pathol. 2001;18(2):109-14.
Schena, Quantitative Monitoring of Gene Expression Patterns with a Complementary DNA Microarray. Science. 1995;270:467-70.

Scott et al. Searching for peptide ligands with an epitope library. Science. Jul. 27, 1990;249(4967):386-90.
Seffernick et al., Melamine deaminase and atrazine chlorohydrolase: 98 percent identical but functionally different. J Bacteriol. Apr. 2001;183(8):2405-10.
Shpaer, GeneAssist. Smith-Waterman and other database similarity searches and identification of motifs. Methods Mol Biol. 1997;70:173-87.
Sikorski et al., A system of shuttle vectors and yeast host strains designed for efficient manipulation of DNA in Saccharomyces cerevisiae. Genetics. May 1989;122(1):19-27.
Smith et al., A phylogenetically conserved NAD+-dependent protein deacetylase activity in the Sir2 protein family. Proc Natl Acad Sci U S A. Jun. 6, 2000;97(12):6658-63.
Smith et al., Comparison of biosequences. Adv Appl Math. 1981;2:482-89.
Stewart et al., Expression of retroviral vectors in transgenic mice obtained by embryo infection. EMBO J. Feb. 1987;6 (2):383-8.
Stillman et al., Epistasis analysis of suppressor mutations that allow HO expression in the absence of the yeast SW15 transcriptional activator. Genetics. Mar. 1994;136(3):781-8.
Strebhardt et al., Additional member of the protein-tyrosine kinase family: the src- and lck-related protooncogene c-tkl. Proc Natl Acad Sci U S A. Dec. 1987;84(24):8778-82.
Suzuki et al., Synthesis and histone deacetylase inhibitory activity of new benzamide derivatives. J Med Chem. Jul. 29, 1999;42(15):3001-3.
Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.
Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.
Taunton et al., Deacetylation. The Scientist. 1999;13:13.
Thornton et al., Protein Engineering: Editorial Overview. Curr Opin Biotechnol. 1995;6(4):367-69.
Tissenbaum et al., Increased dosage of a sir-2 gene extends lifespan in Caenorhabditis elegans. Nature. Mar. 8, 2001;410(6825):227-30.
Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalaminbiosynthesis in Salmonella typhimurium LT2. J Biol Chem. Nov. 27, 1998;273(48):31788-94.
Turner, Decoding the nucleosome. Cell. Oct. 8, 1993;75(1):5-8.
Valerio et al., Synthesis of peptide analogues using the multipin peptide synthesis method. Anal Biochem. Aug. 15, 1991;197(1):168-77.
Van Der Putten et al., Efficient insertion of genes into the mouse germ line via retroviral vectors. Proc Natl Acad Sci U S A. Sep. 1985;82(18):6148-52.
Varga-Weisz et al., Chromatin-remodeling factors: machines that regulate? Curr Opin Cell Biol. Jun. 1998;10 (3):346-53.
Verdel et al., Identification of a new family of higher eukaryotic histone deacetylases. Coordinate expression of differentiation-dependent chromatin modifiers. J Biol Chem. Jan. 22, 1999;274(4):2440-5.
Vidal et al., RPD3 encodes a second factor required to achieve maximum positive and negative transcriptional states in Saccharomyces cerevisiae. Mol Cell Biol. Dec. 1991;11(12):6317-27.
Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J BiolChem. Apr. 5, 1990;265(10):5736-46.
Wallace et al., Understanding cytochrome c function: engineering protein structure by semisynthesis. FASEB J. Apr. 1, 1993;7(6):505-15.
Wang et al., HDAC4, a human histone deacetylase related to yeast HDA1, is a transcriptional corepressor. Mol Cell Biol. Nov. 1999;19(11):7816-27.

(56) References Cited

OTHER PUBLICATIONS

Wang et al., Isolation of high-affinity peptide antagonists of 14-3-3 proteins by phage display. Biochemistry. Sep. 21, 1999;38(38):12499-504.
Weinberg, Finding the anti-oncogene. Sci Am. Sep. 1988;259(3):44-51.
Witkowski et al., Conversion of a beta-ketoacyl synthase to a malonyl decarboxylase by replacement of the active-site cysteine with glutamine. Biochemistry. Sep. 7, 1999;38(36):11643-50.
Workman et al., Alteration of nucleosome structure as a mechanism of transcriptional regulation. Annu Rev Biochem. 1998;67:545-79.
Xie et al., Sum1 and Hst1 repress middle sporulation-specific gene expression during mitosis in Saccharomyces cerevisiae. EMBO J. Nov. 15, 1999;18(22):6448-54.
Xu et al., Coactivator and corepressor complexes in nuclear receptor function. Curr Opin Genet Dev. Apr. 1999;9 (2):140-7.
Xue et al., NURD, a novel complex with both ATP-dependent chromatin-remodeling and histone deacetylase activities. Mol Cell. Dec. 1998;2(6):851-61.
Yaffe et al., The structural basis for 14-3-3:phosphopeptide binding specificity. Cell. Dec. 26, 1997;91(7):961-71.
Yang et al., Cloning and characterization of two mouse genes with homology to the yeast Sir2 gene. Genomics. Nov. 1, 2000;69(3):355-69.
Yang et al., Maintenance of G2 arrest in the Xenopus oocyte: a role for 14-3-3-mediated inhibition of Cdc25 nuclear import. EMBO J. Apr. 15, 1999;18(8):2174-83.
Yang et al., Transcriptional repression by YY1 is mediated by interaction with a mammalian homolog of the yeast global regulator RPD3. Proc Natl Acad Sci U S A. Nov. 12, 1996;93(23):12845-50.
Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.
Yoshida et al., Potent and specific inhibition of mammalian histone deacetylase both in vivo and in vitro by trichostatin A. J Biol Chem. Oct. 5, 1990;265(28):17174-9.
Yoshida et al., Trichostatin A and trapoxin: novel chemical probes for the role of histone acetylation in chromatin structure and function. Bioessays. May 1995;17(5):423-28.
Zhang et al., The dermatomyositis-specific autoantigen Mi2 is a component of a complex containing histone 1-deacetylase and nucleosome remodeling activities. Cell. Oct. 16, 1998;95(2):279-89.
Goy et al., Phase II study of proteasome inhibitor bortezomib in relapsed or refractory B-cell non-Hodgkin's lymphoma. J Clin Oncol. Feb. 1, 2005;23(4):667-75. Epub Dec. 21, 2004.
Kagaku Daijiten 1 (Chemistry Unabridged Dictionary 1), 377 (1960).
Singh et al, DN 140:232, RN 276703-84-5 (2003).
U.S. Appl. No. 60/289,850, filed May 9, 2001, Schreiber et al.
U.S. Appl. No. 60/664,470, filed Mar. 22, 2005, Bradner et al.
U.S. Appl. No. 60/773,172, filed Feb. 14, 2006, Bradner et al.
U.S. Appl. No. 60/773,510, filed Feb. 14, 2006, Bradner et al.
International Search Report and Written Opinion for PCT/US2007/062145 dated Jun. 24, 2008.
International Preliminary Report on Patentability for PCT/US2007/062145 dated Aug. 28, 2008.
International Search Report and Written Opinion for PCT/US2007/062152 dated Oct. 7, 2008.
International Search Report and Written Opinion for PCT/US2007/062152 dated Oct. 14, 2008.
International Preliminary Report on Patentability for PCT/US2007/062152 dated Mar. 19, 2009.
International Search Report and Written Opinion for PCT/US2006/010676 dated Jul. 14, 2008.
International Preliminary Report on Patentability for PCT/US2006/010676 dated Mar. 19, 2009.
Supplementary European Search Report for 06748614.2 dated Oct. 16, 2009.
International Search Report and Written Opinion for PCT/US2007/010587 dated Jan. 29, 2008.
International Preliminary Report on Patentability for PCT/US2007/010587 dated Nov. 13, 2008.
International Search Report for PCT/US2002/014835 dated Dec. 20, 2002.
Written Opinion for PCT/US2002/014835 dated Aug. 8, 2003.
International Preliminary Exam Report for PCT/US2002/014835 dated Jun. 4, 2004.
[No Author Listed] Targeting the aggresome with an HDAC6 inhibitor in combination with velcade for myeloma therapy. Cancer Biology and Therapy. 2005;4(7):i-iv.
Adams, The proteasome: a suitable antineoplastic target. Nat Rev Cancer. May 2004;4(5):349-60.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Anderson et al., Analytical Techniques in Combinatorial Chemistry: MAS CH Correlation in Solvent-Swollen Resin. J Org Chem. 1995;60:2650-51.
Anton et al., Intracellular localization of proteasomal degradation of a viral antigen. J Cell Biol. Jul. 12, 1999;146 (1):113-24.
Antonjuk et al., Asymmetric Induction in the Additions of Anions of Allylic Sulfoxides to Benzaldehyde. Aust J Chem. 1980;33:2635-51.
Attal et al., Single versus double autologous stem-cell transplantation for multiple myeloma. N Engl J Med. Dec. 25, 2003;349(26):2495-502.
Bennett et al., Global impairment of the ubiquitin-proteasome system by nuclear or cytoplasmic protein aggregates precedes inclusion body formation. Mol Cell. Feb. 4, 2005;17(3):351-65.
Berenbaum et al. What is synergy? Pharmacol Rev. Jun. 1989;41(2):93-141.
Berge et al., Pharmaceutical salts. J Pharm Sci. Jan. 1977;66(1):1-19.
Blackwell et al., A one-bead, one-stock solution approach to chemical genetics: part 1. Chem Biol. Dec. 2001;8 (12)1167-82.
Bolden et al., Anticancer activities of histone deacetylase inhibitorsNat Rev Drug Discov. Sep. 2006;5(9):769-84.
Bolger et al., Intracellular trafficking of histone deacetylase 4 regulates neuronal cell death. J Neurosci. Oct. 12, 2005;25(41):9544-53.
Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.
Bowers et al., Synthesis and Conformation-Activity Relationships of the Peptide Isosteres of FK228 and Largazole. J Am Chem Soc. 2009;131:2900-05.
Bowers et al., Total synthesis and biological mode of action of largazole: a potent class I histone deacetylase inhibitor. J Am Chem Soc. Aug. 20, 2008;130(33):11219-22. Epub Jul. 19, 2008.
Brummel et al., A mass spectrometric solution to the address problem of combinatorial libraries. Science. Apr. 15, 1994;264(5157):399-402.
Catley et al., NVP-LAQ824 is a potent novel histone deacetylase inhibitor with significant activity against multiple myeloma. Blood. Oct. 1, 2003;102(7):2615-22. Epub Jun. 19, 2003.
Chauhan et al., Blockade of Hsp27 overcomes Bortezomib/proteasome inhibitor PS-341 resistance in lymphoma cells. Cancer Res. Oct. 1, 2003;63(19):6174-7.
Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.
Chu et al., Free Solution Identification of Candidate Peptides from Combinatorial Libraries by Affinity Capillary Electrophoresis/Mass Spectrometry. J Am Chem Soc. 1995;117:5419-20.
Clemons et al., A one-bead, one-stock solution approach to chemical genetics: part 2. Chem Biol. Dec. 2001;8 (12):1183-95.
Cohen et al., The histone deacetylase HDAC4 connects neural activity to muscle transcriptional reprogramming. J Biol Chem. Nov. 16, 2007;282(46):33752-9. Epub Sep. 16, 2007.

(56) References Cited

OTHER PUBLICATIONS

Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
De Ruijter et al., Histone deacetylases (HDACs): characterization of the classical HDAC family. Biochem J. Mar. 15, 2003;370(Pt 3):737-49.
Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.
Dul et al., Hsp70 and antifibrillogenic peptides promote degradation and inhibit intracellular aggregation of amyloidogenic light chains. J Cell Biol. Feb. 19, 2001;152(4):705-15.
Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.
Fabian et al., A small molecule-kinase interaction map for clinical kinase inhibitors. Nat Biotechnol. Mar. 2005;23 (3):329-36. Epub Feb. 13, 2005.
Fabunmi et al., Activity and regulation of the centrosome-associated proteasome. J Biol Chem. Jan. 7, 2000;275 (1):409-13.
Kouzarides, Acetylation: a regulatory modification to rival phosphorylation? EMBO J. Mar. 15, 2000;19(6):1176-9.
Kozbar et al., The production of monoclonal antibodies from human lymphocytes. Immunology Today. 1983;4:72-79.
Krieger et al., Chemical studies of histone acetylation. Substrate specificity of a histone deacetylase from calf thymus nuclei. J Biol Chem. Jan. 10, 1974;249(1):332-4.
Kwon et al., Depudecin induces morphological reversion of transformed fibroblasts via the inhibition of histone deacetylase. Proc Natl Acad Sci U S A. Mar. 31, 1998;95(7):3356-61.
Landry et al., The silencing protein SIR2 and its homologs are NAD-dependent protein deacetylases. Proc Natl Acad Sci U S A. May 23, 2000;97(11):5807-11.
Lee et al., A positive role for histone acetylation in transcription factor access to nucleosomal DNA. Cell. Jan. 15, 1993;72(1):73-84.
Lee et al., A Strategy for Macrocyclic Ring Closure and Functionalization Aimed toward Split-Pool Syntheses. J Am Chem Soc. 1999;121(45):10648-49.
Lizcano et al., Cell type-specific roles of histone deacetylase in TR ligand-independent transcriptional repression. Mol Cell Endocrinol. Feb. 14, 2001;172(1-2):13-20.
Lopez-Girona et al., Nuclear localization of Cdc25 is regulated by DNA damage and a 14-3-3 protein. Nature. Jan. 14, 1999;397(6715):172-5.
Luger et al., Crystal structure of the nucleosome core particle at 2.8 A resolution. Nature. Sep. 18, 1997;389 (6648):251-60.
Lutterbach et al., ETO, a target of t(8;21) in acute leukemia, interacts with the N-CoR and mSin3 corepressors. Mol Cell Biol. Dec. 1998;18(12):7176-84.
MacBeath et al., Printing proteins as microarrays for high-throughput function determination. Science. Sep. 8, 2000;289(5485):1760-3.
Marcand et al., Silencing of genes at nontelomeric sites in yeast is controlled by sequestration of silencing factors at telomeres by Rap 1 protein. Genes Dev. Jun. 1, 1996;10(11):1297-309.
Martinelli et al., Molecular therapy for multiple myeloma. Haematologica. Sep. 2001;86(9):908-17.
Marushige et al., Template properties of liver chromatin. J Mol Biol. Jan. 1966;15(1):160-74.
Massa et al., Synthesis and antimicrobial and cytotoxic activities of pyrrole-containing analogues of trichostatin A. J Med Chem. Oct. 1990;33(10):2845-9.
McKenzie et al., The centromere and promoter factor, 1, CPF1, of Saccharomyces cerevisiae modulates gene activity through a family of factors including SPT21, RPD1 (SIN3), RPD3 and CCR4. Mol Gen Genet Sep. 1993;240 (3):374-86.
Megee et al., Genetic analysis of histone H4: essential role of lysines subject to reversible acetylation. Science. Feb. 16, 1990;247(4944):841-5.
Miska et al., HDAC4 deacetylase associates with and represses the MEF2 transcription factor. EMBO J. Sep. 15, 1999;18(18):5099-107.
Moazed, Enzymatic activities of Sir2 and chromatin silencing. Curr Opin Cell Biol. Apr. 2001;13(2):232-8.
Mori et al., Synthesis of trichostatin A, a potent differentiation inducer of friend leukemic cells, and its antipode. Tetrahedron. 1988;44:6013-20.
Mowat et al., Rearrangements of the cellular p53 gene in erythroleukaemic cells transformed by Friend virus. Nature. Apr. 18-24, 1985;314(6012):633-6.
Mullins et al., Transgenesis in nonmurine species. Hypertension. Oct. 1993;22(4):630-3.
Munshi et al., Acetylation of HMG I(Y) by CBP turns off IFN beta expression by disrupting the enhanceosome. Mol Cell. Oct. 1998;2(4):457-67.
Nagai et al., Synthesis of a Bicyclic Dipeptide with the Shape of .beta.-Turn Central Part. Tetrahedron Lett. 1985;26:647-50.
Nagy et al., Nuclear receptor repression mediated by a complex containing SMRT, mSin3A, and histone deacetylase. Cell. May 2, 1997;89(3):373-80.
Narang, DNA Synthesis. Tetrahedron. 1983;39:3-22.
Nasmyth et al., Both positive and negative regulators of HO transcription are required for mother-cell-specific mating-type switching in yeast. Cell. Feb. 27, 1987;48(4):579-87.
Needleman et al., A general method applicable to the search for similarities in the amino acid sequence of two proteins. J Mol Biol. Mar. 1970;48(3):443-53.
Needles et al., Generation and screening of an oligonucleotide-encoded synthetic peptide library. Proc Natl Acad Sci. 1993;90:10700-04.
Neer et al., The ancient regulatory-protein family of WD-repeat proteins. Nature. Sep. 22, 1994;371(6495):297-300.
Nestler et al., A General Method for Molecular Tagging of Encoded Combinatorial Chemistry Libraries. J Org Chem. 1994;59:4723-24.
Ng et al., Histone deacetylases: silencers for hire. Trends Biochem Sci. Mar. 2000;25(3):121-6.
Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.
Nikolaiev et al., Peptide-encoding for structure determination of nonsequenceable polymers within libraries synthesized and tested on solid-phase supports. Pept Res. May-Jun. 1993;6(3):161-70.
Noll, Characterization of macromolecules by constant velocity sedimentation. Nature. Jul. 22, 1967;215(5099):360-3.
Oliva et al., Histone hyperacetylation can induce unfolding of the nucleosome core particle. Nucleic Acids Res. May 11, 1990;18(9):2739-47.
Park et al., Point mutations in the yeast histone H4 gene prevent silencing of the silent mating type locus HML. Mol Cell Biol. Sep. 1990;10(9):4932-4.
Patek et al., Safety-catch anchoring linkage for synthesis of peptide amides by Boc/Fmoc strategu. Tetrahedron Lett. 1991;32:3891-94.
Perrod et al., A cytosolic NAD-dependent deacetylase, Hst2p, can modulate nucleolar and telomeric silencing in yeast. EMBO J. Jan. 15, 2001;20(1-2):197-209.
Peterson et al., Small molecule developmental screens reveal the logic and timing of vertebrate development. Proc Natl Acad Sci U S A. Nov. 21, 2000;97(24):12965-9.
Phillips, The challenge of gene therapy and DNA delivery. J Pharm Pharmacol. Sep. 2001;53(9):1169-74.
Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

(56) References Cited

OTHER PUBLICATIONS

Qian et al., A retinoblastoma-binding protein related to a negative regulator of Ras in yeast. Nature. Aug. 12, 1993;364 (6438):648-52.
Richon et al., A class of hybrid polar inducers of transformed cell differentiation inhibits histone deacetylases. Proc Natl Acad Sci U S A. Mar. 17, 1998;95(6):3003-7.
Richon et al., Histone deacetylase inhibitor selectively induces p21WAF1 expression and gene-associated histone acetylation. Proc Natl Acad Sci U S A. Aug. 29, 2000;97(18):10014-9.
Richon et al., Second generation hybrid polar compounds are potent inducers of transformed cell differentiation. Proc Natl Acad Sci U S A. Jun. 11, 1996;93(12):5705-8.
Rine et al., Four genes responsible for a position effect on expression from HML and HMR in *Saccharomyces cerevisiae*. Genetics. May 1987;116(1):9-22.
Rittinger et al., Structural analysis of 14-3-3 phosphopeptide complexes identifies a dual role for the nuclear export signal of 14-3-3 in ligand binding. Mol Cell. Aug. 1999;4(2):153-66.
Roberts et al., Directed evolution of a protein: selection of potent neutrophil elastase inhibitors displayed on M13 fusion phage. Proc Natl Acad Sci U S A. Mar. 15, 1992;89(6):2429-33.
Gelmetti et al., Aberrant recruitment of the nuclear receptor corepressor-histone deacetylase complex by the acute myeloid leukemia fusion partner ETO. Mol Cell Biol. Dec. 1998;18(12):7185-91.
Geysen et al., Use of peptide synthesis to probe viral antigens for epitopes to a resolution of a single amino acid. Proc Natl Acad Sci U S A. Jul. 1984;81(13):3998-4002.
Gordon et al., Design of peptide derived amino alcohols as transition-state analog inhibitors of angiotensin converting enzyme. Biochem Biophys Res Commun. Jan. 16, 1985;126(1):419-26.
Gorlich, Nuclear protein import. Curr Opin Cell Biol. Jun. 1997;9(3):412-9.
Gassier et al., Transgenesis by means of blastocyst-derived embryonic stem cell lines. Proc Natl Acad Sci U S A. Dec. 1986;83(23):9065-9.
Gray et al., The human histone deacetylase family. Exp Cell Res. Jan. 15, 2001;262(2):75-83.
Green et al., When the products of oncogenes and anti-oncogenes meet Cell. Jan. 13, 1989;56(1):1-3.
Grignani et al., Fusion proteins of the retinoic acid receptor-alpha recruit histone deacetylase in promyelocytic leukaemia. Nature. Feb. 19, 1998;391(6669):815-8.
Grozinger et al., Regulation of histone deacetylase 4 and 5 and transcriptional activity by 14-3-3-dependent cellular localization. Proc Natl Acad Sci U S A. Jul. 5, 2000;97(14):7835-40.
Grunstein, Histone acetylation in chromatin structure and transcription. Nature. Sep. 25, 1997;389(6649):349-52.
Grunstein, Molecular model for telomeric heterochromatin in yeast. Curr Opin Cell Biol. Jun. 1997;9(3):383-7.
Gu et al., Activation of p53 sequence-specific DNA binding by acetylation of the p53 C-terminal domain. Cell. Aug. 22, 1997;90(4):595-606.
Guarente, Sir2 links chromatin silencing, metabolism, and aging. Genes Dev. May 1, 2000;14(9):1021-6.
Haggarty et al., Dissecting cellular processes using small molecules: identification of colchicine-like, taxol-like and other small molecules that perturb mitosis. Chem Biol. Apr. 2000;7(4):275-86.
Hansen et al., Retinoblastoma and the progression of tumor genetics. Trends Genet. May 1988;4(5):125-8.
Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.
Hassig et al., A role for histone deacetylase activity in HDAC1-mediated transcriptional repression. Proc Natl Acad Sci U S A. Mar. 31, 1998;95(7):3519-24.
Hassig et al., Histone deacetylase activity is required for full transcriptional repression by mSin3A. Cell. May 2, 1997;89(3):341-7.
Hay et al., Histone deacetylase. Association with a nuclease resistant, high molecular weight fraction of HeLa cell chromatin. J Biol Chem. Mar. 25, 1983;258(6):3726-34.
Hayes et al., Histones H2A/H2B inhibit the interaction of transcription factor IIIA with the Xenopus borealis somatic 5S RNA gene in a nucleosome. Proc Natl Acad Sci U S A. Feb. 15, 1992;89(4):1229-33.
He et al., Distinct interactions of PML-RARalpha and PLZF-RARalpha with co-repressors determine differential responses to RA in APL. Nat Genet. Feb. 1998;18(2):126-35.
Hecht et al., Histone H3 and H4 N-termini interact with SIR3 and SIR4 proteins: a molecular model for the formation of heterochromatin in yeast Cell. Feb. 24, 1995;80(4):583-92.
Hicks et al., Protein import into the nucleus: an integrated view. Annu Rev Cell Dev Biol. 1995;11:155-88.
Houdebine, The methods to generate transgenic animals and to control transgene expression. J Biotechnol. Sep. 25, 2002;98(2-3):145-60.
Houghten, General method for the rapid solid-phase synthesis of large numbers of peptides: specificity of antigen-antibody interaction at the level of individual amino acids. Proc Natl Acad Sci U S A. Aug. 1985;82(15):5131-5.
Huang et al., Nuclear receptor corepressors partner with class II histone deacetylases in a Sin3-independent repression pathway. Genes Dev. Jan. 1, 2000;14(1):45-54.
Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.
Imai et al., Transcriptional silencing and longevity protein Sir2 is an NAD-dependent histone deacetylase. Nature. Feb. 17, 2000;403(6771):795-800.
Imhof et al., Acetylation of general transcription factors by histone acetyltransferases. Curr Biol. Sep. 1, 1997;7 (9):689-92.
Itakura et al., Expression in *Escherichia coli* of a Chemically Synthesized Gene for the Hormone Somatostatin. Science. 1984;198:1056-63.
Itakura et al., Synthesis and use of synthetic oligonucleotides. Annu Rev Biochem. 1984;53:323-56.
Jacobs et al., Combinatorial chemistry—applications of light-directed chemical synthesis. Trends Biotechnol. Jan. 1994;12(1):19-26.
Jaenisch, Germ line integration and Mendelian transmission of the exogenous Moloney leukemia virus. Proc Natl Acad Sci U S A. Apr. 1976;73(4):1260-4.
Jaenisch, Transgenic animals. Science. Jun. 10, 1988;240(4858):1468-74.
Jahner et al., De novo methylation and expression of retroviral genomes during mouse embryogenesis. Nature. Aug. 12, 1982;298(5875):623-8.
Jahner et al., Insertion of the bacterial gpt gene into the germ line of mice by retroviral infection. Proc Natl Acad Sci U S A. Oct. 1985;82(20):6927-31.
Jin et al., Transcriptional regulation of the MDR1 gene by histone acetyltransferase and deacetylase is mediated by NF-Y. Mol Cell Biol. Jul. 1998;18(7):4377-84.
Johnson et al., Deacetylase activity associates with topoisomerase II and is necessary for etoposide-induced apoptosis. J Biol Chem. Feb. 16, 2001;276(7):4539-42. Epub Jan. 2, 2001.
Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.
Johnson et al., Molecular cloning of *Drosophila melanogaster* cDNAs that encode a novel histone deacetylase dHDAC3. Gene. Oct. 9, 1998;221(1):127-34.
Jung et al. Amide analogues of trichostatin A as inhibitors of histone deacetylase and inducers of terminal cell differentiation. J Med Chem. Nov. 4, 1999;42(22):4669-79.
Kappel et al., Regulating gene expression in transgenic animals. Curr Opin Biotechnol. Oct. 1992;3(5):548-53.
Kennedy et al., Redistribution of silencing proteins from telomeres to the nucleolus is associated with extension of life span in *S. cerevisiae*. Cell. May 2, 1997;89(3):381-91.

(56) References Cited

OTHER PUBLICATIONS

Kerr et al., Encoded Combinatorial Peptide Libraries Containing Non-Natural Amino Acids. J Am Chem, Soc. 1993;115:2529-31.
Khockbin et al., Functional significance of histone deacetylase diversity. Curr Opin Genet Dev. Apr. 2001;11(2):162-6.
Kijima et al., Trapoxin, an antitumor cyclic tetrapeptide, is an irreversible inhibitor of mammalian histone deacetylase. J Biol Chem. Oct. 25, 1993;268(30):22429-35.
Kikuchi et al., Multiplicity of histone deacetylase from calf thymus. FEBS Lett. Feb. 1, 1973;29(3):280-282.
Kleff et al., Identification of a gene encoding a yeast histone H4 acetyltransferase. J Biol Chem. Oct. 20, 1995;270 (42):24674-7.
Koeller et al., Chemical genetic modifier screens: small molecule trichostatin suppressors as probes of intracellular histone and tubulin acetylation. Chem Biol. May 2003;10(5):397-410.
Kohler et al., Continuous cultures of fused cells secreting antibody of predefined specificity. Nature. Aug. 7, 1975;256 (5517):495-7.
Feling et al., Salinosporamide A: a highly cytotoxic proteasome inhibitor from a novel microbial source, a marine bacterium of the new genus *Salinospora*. Angew Chem Int Ed Engl. Jan. 20, 2003;42(3):355-7.
Fitch et al., High-Resolution .sup.1H NMR in Solid-Phase Organic Synthesis. J Org Chem. 1994;59:7955-56.
Garcia-Mata et al., Characterization and dynamics of aggresome formation by a cytosolic GFP-chimera. J Cell Biol. Sep. 20, 1999;146(6):1239-54.
Garcia-Mata et al., Hassles with taking out the garbage: aggravating aggresomes. Traffic. Jun. 2002;3(6):388-96.
Gregoretti et al., Molecular evolution of the histone deacetylase family: functional implications of phylogenetic analysisJ Mol Biol. Apr. 16, 2004;338(1):17-31.
Gregory et al., Combination chemotherapy versus melphalan and prednisolone in the treatment of multiple myeloma: an overview of published trials. J Clin Oncol. Feb. 1992;10(2):334-42.
Grozinger et al., Deacetylase enzymes: biological functions and the use of small-molecule inhibitors. Chem Biol. Jan. 2002;9(1):3-16.
Grozinger et al., Three proteins define a class of human histone deacetylases related to yeast Hadlp. Proc Natl Acad Sci U S A. Apr. 27, 1999;96(9):4868-73.
Haggarty et al., Domain-selective small-molecule inhibitor of histone deacetylase 6 (HDAC6)-mediated tubulin deacetylation. Proc Natl. Acad Sci U S A. Apr. 15, 2003;100(8):4389-94. Epub Apr. 3, 2003.
Haggarty et al., Mapping chemical space using molecular descriptors and chemical genetics: deacetylase inhibitors. Comb Chem High Throughput Screen. Nov. 2004;7(7):669-76.
Haggarty et al., Multidimensional chemical genetic analysis of diversity-oriented synthesis-derived deacetylase inhibitors using cell-based assays. Chem Biol. May 2003;10(5):383-96.
Hassig et al., Nuclear histone acetylases and deacetylases and transcriptional regulation: HATs off to HDACs. Curr Opin Chem Biol. Oct. 1997;1(3):300-8.
Hathaway et al., Dissecting cell biology with chemical scalpels. Curr Opin Cell Biol. Feb. 2005;17(1):12-9.
Hideshima et al., Antitumor activity of lysophosphatidic acid acyltransferase-beta inhibitors, a novel class of agents, in multiple myeloma. Cancer Res. Dec. 1, 2003;63(23):8428-36.
Hideshima et al., Molecular mechanisms mediating antimyeloma activity of proteasome inhibitor PS-341. Blood. Feb. 15, 2003;101(4):1530-4. Epub Sep. 26, 2002.
Hideshima et al., Molecular mechanisms of novel therapeutic approaches for multiple myeloma. Nat Rev Cancer. Dec. 2002;2(12):927-37.
Hideshima et al., NF-.kappa.B as a therapeutic target in multiple myeloma. J Biol Chem. May 10, 2002;277 (19):16639-47. Epub Feb. 28, 2002.
Hideshima et al. Novel therapeutic approaches for multiple myeloma. Immunol Rev. Aug. 2003;194:164-76.
Hideshima et al., p38 MAPK inhibition enhances PS-341 (bortezomib)-induced cytotoxicity against multiple myeloma cells. Oncogene. Nov. 18, 2004;23(54):8766-76.
Hideshima et al., Proteasome inhibitor PS-341 abrogates IL-6 triggered signaling cascades via caspase-dependent downregulation of gp130 in multiple myeloma. Oncogene. Nov. 20, 2003;22(52):83 86-93.
Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.
Hideshima et al., The proteasome inhibitor PS-341 inhibits growth, induces apoptosis, and overcomes drug resistance in human multiple myeloma cells. Cancer Res. Apr. 1, 2001;61(7):3071-6.
Hideshima et al., The role of tumor necrosis factor alpha in the pathophysiology of human multiple myeloma: herapeutic applications. Oncogene. Jul. 27, 2001;20(33):4519-27.
Hu et al., Cloning and characterization of a novel human class I histone deacetylase that functions as a transcription repressor. J Biol Chem. May 19, 2000;275(20):15254-64.
Hubbert et al., HDAC6 is a microtubule-associated deacetylase. Nature. May 23, 2002;417(6887):455-8.
Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.
Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.
Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.
Johnston et al., Aggresomes: a cellular response to misfolded proteins. J Cell Biol. Dec. 28, 1998;143(7):1883-98.
Johnstone, Histone-deacetylase inhibitors: novel drugs for the treatment of cancer. Nat Rev Drug Discov. Apr. 2002;1 (4):287-99.
Jones et al., Probing the elusive catalytic activity of vertebrate class IIa histone deacetylases. Bioorg Med Chem Lett. Mar. 15, 2008;18(6):1814-9. Epub Feb. 14, 2008.
Junn et al., Parkin accumulation in aggresomes due to proteasome impairment. J Biol Chem. Dec. 6, 2002;277 (49):47870-7. Epub Oct. 2, 2002.
Kao et al., Isolation of a novel histone deacetylase reveals that class I and class II deacetylases promote SMRT-mediated repression. Genes Dev. Jan. 1, 2000;14(1):55-66.
Katoh et al., MAFFT: a novel method for rapid multiple sequence alignment based on fast Fourier transform. Nucleic Acids Res. Jul. 15, 2002;30(14):3059-66.
Kawaguchi et al., The deacetylase HDAC6 regulates aggresome formation and cell viability in response to misfolded protein stress. Cell. Dec. 12, 2003;115(6):727-38.
Kopito et al., Aggresomes and Russell bodies. Symptoms of cellular indigestion? EMBO Rep. Sep. 2000;1(3):225-31.
Kopito, Aggresomes, inclusion bodies and protein aggregation. Trends Cell Biol. Dec. 2000;10(12):524-30.
Kumar et al., MEGA: a biologist-centric software for evolutionary analysis of DNA and protein sequences. Brief Bioinform. Jul. 2008;9(4):299-306. Epub Apr. 16, 2008.
Kuruvilla et al., Dissecting glucose signaling with diversity-oriented synthesis and small-molecule microarrays. Nature. Apr. 11, 2002;416(6881):653-7.
Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.
Lam et al., The "One-Bead-One-Compound" Combinatorial Library Method. Chem Rev. Apr. 1, 1997;97(2):411-448.
Lee et al., Histone acetyltransferase complexes: one size doesn't fit all. Nat Rev Mol Cell Biol. Apr. 2007;8(4):284-95.
Lee et al., Proteasome inhibitors disrupt the unfolded protein response in myeloma cells. Proc Natl Acad Sci U S A. Aug. 19, 2003;100(17):9946-51. Epub Aug. 5, 2003.
Lin et al., Generation and Aldol Reaction of Endlate Anion Adjacnet to a .eta.3-Allyl-Mo(Co).sup.2Cp Moiety. A New Approach to the Stereoselctive Synthesis of 1,3,5-Triol and 2-Vinyl-3-Hydroxyl-Tetrahydrofuran. TetrahedronLetters.1990;31(52):7645-48.

(56) References Cited

OTHER PUBLICATIONS

Lin et al., Role of the histone deacetylase complex in acute promyelocytic leukaemia. Nature. Feb. 19, 1998;391 (6669):811-4.
Look et al., Methods for Combinatorial Organic Synthesis: The Use of Fast .sup.13C NMR Analysis for Gel Phase Reaction Monitoring. J Org Chem. 1994;59:7588-90.
Macherla et al., Structure-activity relationship studies of salinosporamide A (NPI-0052), a novel marine derived proteasome inhibitor. J Med Chem. Jun. 2, 2005;48(11):3684-7.
Maddry et al., Inhibition of the Her2 Tyrosine Kinase and Characterization of a Hydrophobic Site Near the Nucleotide Binding Domain. Bioorganic Med Chem Letter. 1997;7(16):2109-14.
Magnaghi-Jaulin et al., Retinoblastoma protein represses transcription by recruiting a histone deacetylase. Nature. Feb. 5, 1998;391(6667):601-4.
Manetto et al., Selective presence of ubiquitin in intracellular inclusions. Am J Pathol. Mar. 1989;134(3):505-13.
Tallarico et al., An alkylsilyl-tethered, high-capacity solid support amenable to diversity-oriented synthesis for one-bead, one-stock solution chemical genetics. J Comb Chem. May-Jun. 2001;3(3):312-8.
Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.
Tao et al., Deacetylase inhibition promotes the generation and function of regulatory T cells. Nat Med. Nov. 2007;13 (11):1299-307. Epub Oct. 7, 2007.
Taunton et al., A mammalian histone deacetylase related to the yeast transcriptional regulator Rpd3p. Science. Apr. 19, 1996;272(5260):408-11.
Taunton et al., Synthesis of Natural and Modified Trapoxins, Useful Reagents for Exploring Histone Deacetylase Function. J Am Chem Soc. 1996;118:10412-22.
Tong et al., Chromatin deacetylation by an ATP-dependent nucleosome remodeling complex. Nature. 1997;395:917-21.
Tsankova et al., Sustained hippocampal chromatin regulation in a mouse model of depression and antidepressant action. Nat Neurosci. Apr. 2006;9(4):519-25. Epub Feb. 26, 2006.
Uchiyama et al., Adhesion of human myeloma-derived cell lines to bone marrow stromal cells stimulates interleukin-6 secretion. Blood. Dec. 15, 1993;82(12):3712-20.
Uong et al., Stereocontrolled Functionalization of Acyclic Molybdenum-.eta..sup.3-Allyl Complexes: A New Approach to the Stereoselective Synthesis of 1,3-Dials. J Chem Soc Chem Commun. 1990:1285-87.
Urnov et al., Targeting of N-CoR and histone deacetylase 3 by the oncoprotein v-erbA yields a chromatin Infrastructure-dependent transcriptional repression pathway. EMBO J. Aug. 1, 2000;19(15):4074-90.
Vannini et al., Crystal structure of a eukaryotic zinc-dependent histone deacetylase, human HDAC8, complexed with a hydroxamic acid inhibitor. Proc Natl Arad Sci U S A. Oct. 19, 2004;101(42):15064-9. Epub Oct. 11, 2004.
Vegas et al., Fluorous-based small-molecule microarrays for the discovery of histone deacetylase inhibitors. Angew Chem Int Ed Engl. 2007;46(42):7960-4.
Venter et al., The sequence of the human genome. Science. Feb. 16, 2001;291(5507):1304-51.
Vong et al., Regio-and Stereocontrolled Functionalization of Acyclic Molybdenum-.eta..sup.3-Allyl Complexes.J Am Chem Soc. 1991;113:573-82.
Wang et al., Zinc binding in HDAC inhibitors: a DFT study. J Org Chem. Jul. 6, 2007;72(14):5446-9. Epub Jun. 19, 2007.
Warrell et al., Therapeutic targeting of transcription in acute promyelocytic leukemia by use of an inhibitor of histone deacetylase. J Natl Cancer Inst. Nov. 4, 1998;90(21):1621-5.
Wegener et al., A fluorogenic histone deacetylase assay well suited for high-throughput activity screening. Chem Biol. Jan. 2003;10(1):61-8.
Whelan et al., A general empirical model of protein evolution derived from multiple protein families using a maximum-likelihood approach. Mol Biol Evol. May 2001;18(5):691-9.
Wilen et al., Strategies in Optical Resolution. Tetrahedron. 1977;33:2725-36.
Wong et al., Modular synthesis and preliminary biological evaluation of stereochemically diverse 1,3-dioxanes. Chem Biol. Sep. 2004;11(9):1279-91.
Wong et al., Structural biasing elements for in-cell histone deacetylase paralog selectivity. J Am Chem Soc. May 14, 2003;125(19):5586-7.
Yang et al., Isolation and characterization of cDNAs corresponding to an additional member of the human histone deacetylase gene family. J Biol Chem. Oct. 31, 1997;272(44):28001-7.
Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.
Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003. cited byapplicant.
Zhou et al., Cloning and characterization of a histone deacetylase, HDAC9. Proc Natl Arad Sci U S A. Sep. 11, 2001;98(19):10572-7. Epub Sep. 4, 2001.
Zhou et al., Identification of a transcriptional repressor related to the noncatalytic domain of histone deacetylases 4 and 5. Proc Natl Acad Sci U S A. Feb. 1, 2000;97(3):1056-61.
International Search Report and Written Opinion for PCT/US2009/004235 dated Mar. 4, 2010.
Extended European Search Report for EP 07757000.0 dated May 3, 2011.
Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.
Dankwardt et al., Solid-phase synthesis of di- and tripeptidic hydroxamic acids as inhibitors of procollagen C-proteinase. Bioorg Med Chem Lett. Nov. 20, 2000;10(22):2513-6.
Giacomelli et al., Simple one-flask method for the preparation of hydroxamic acids. Org Lett. Jul. 24, 2003;5 (15):2715-7.
Khomutov et al., Directed synthesis of inhibitors of enzymic changes of glutamic acid. Doklady Akademii Nauk SSSR. 1965;161(5):1227-30. Russian.
Menger et al., Chemical Reaction between Colliding Vesicles This research was supported by the National Institutes of Health, Grant 21457. Angew Chem Int Ed Engl. Oct. 15, 2001;40(20):3905-3907.
Munegumi et al., Amidation of carboxyl group involved in N-protected amino acids using O-benzylhydroxylamine. Peptide Chemistry. 1993;31:49-52.
Singh et al., Chemistry and structure-activity relationship of HIV-1 integrase inhibitor integracide B and related natural products. J Nat Prod. Oct. 2003;66(10):1338-44.
Stowell et al., The synthesis of N-hydroxy-N'-phenyloctanediamide and its inhibitory effect on proliferation of AXC rat prostate cancer cells. J Med Chem. Apr. 14, 1995;38(8):1411-3.
Invitation to Pay Additional Fees for PCT/US1997/005275 dated Nov. 21, 1997.
International Search Report for PCT/US1997/005275 dated Feb. 16, 1998.
Written Opinion for PCT/US1997/005275 dated Mar. 5, 1998.
International Preliminary Examination Report for PCT/US1997/005275 dated Jul. 3, 1998.
Office Communication, dated Oct. 15, 2008, for U.S. Appl. No. 11/386,959.
Office Communication, dated Jul. 21, 2009, for U.S. Appl. No. 11/386,959.
Office Communication, dated Nov. 28, 2005, for U.S. Appl. No. 10/621,276.
Office Communication, dated Aug. 8, 2006, for U.S. Appl. No. 10/621,276.
Notice of Allowance, dated Mar. 6, 2007, for U.S. Appl. No. 10/621,276.
Office Communication, dated Sep. 16, 2009, for U.S. Appl. No. 11/879,466.

(56) References Cited

OTHER PUBLICATIONS

Notice of Allowance, dated Feb. 4, 2010, for U.S. Appl. No. 11/879,466.
Office Communication, dated Jan. 21, 1998, for U.S. Appl. No. 08/624,735.
Office Communication, dated Jan. 17, 2001, for U.S. Appl. No. 08/624,735.
Office Communication, dated Oct. 10, 2001, for U.S. Appl. No. 08/624,735.
Marks et al., Histone deacetylases and cancer: causes and therapies. Nat Rev Cancer. Dec. 2001;1(3):194-202.
Marks et al., Histone deacetylases. Curr Opin Pharmacol. Aug. 2003;3(4):344-51.
Marmuse et al., "Click chemistry"en route to pseudo-starch. Org Biomol Chem. Jun. 21, 2005;3(12):2225-7. Epub May 11, 2005.
Marx et al., Bench to bedside: the development of rapamycin and its application to stent restenosis. Circulation. Aug. 21, 2001;104(8):852-5.
Meinke et al., Histone deacetylase: a target for antiproliferative and antiprotozoal agents. Curr Med Chem. Feb. 2001;8 (2):211-35.
Meinke et al., Synthesis of apicidin-derived quinolone derivatives: parasite-selective histone deacetylase inhibitors and antiproliferative agents. J Med Chem Dec. 14, 2000;43(25):4919-22.
Metzger et al., Ion-Spray Mass Spectrometry and High-Performance Liquid Chromatography-Mass Spectrometry of Synthetic Peptide Libraries. Angew Chem Int Ed Engl. 1993;32:894-96.
Miano et al., HDAC7 supports vascular integrity. Nat Med. Sep. 2006;12(9):997-8.
Minucci et al., Histone deacetylase inhibitors and the promise of epigenetic (and more) treatments for cancer. Nat Rev Cancer. Jan. 2006;6(1):38-51.
Mitchison, Towards a pharmacological genetics. Chem Biol. Sep. 1994;1(1):3-6.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30. cited byapplicant.
Mitsiades et al., Molecular sequelae of histone deacetylase inhibition in human malignant B cells. Blood. May 15, 2003;101(10):4055-62. Epub Jan. 16, 2003.
Mitsiades et al., Molecular sequelae of proteasome inhibition in human multiple myeloma cells. Proc Natl Acad Sci U S A. Oct. 29, 2002;99(22):14374-9. Epub Oct. 21, 2002.
Mitsiades et al., Novel biologically based therapies for Waldenstrom's macroglobulinemia. Semin Oncol. Apr. 2003;30 (2):309-12.
Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.
Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.
Mottet et al., Histone deacetylase 7 silencing alters endothelial cell migration, a key step in angiogenesis. Circ Res. Dec. 7, 2007;101(12):1237-46. Epub Oct. 18, 2007.
Myers et al., Preparation of the Chiral, C-Protected .alpha.-Amino Aldehydes of High Optical Purity and Their Use as Condensation Components in a Linear Synthesis Strategy. J Am Chem Soc. 1999;121:8401-02.
Nakatsuka et al., Total Synthesis of FK506 and an FKBP Probe Reagent, (C.sub.8, C.sub.9-.sup.13C.sub.2)-FK506. J. Am. Chem. Soc. 1990; 112: 5583-5601.
Nefzi et al., The Current Status of Heterocyclic Combinatorial Libraries. Chem Rev. Apr. 1, 1997;97(2):449-472.
Newman et al., The influence of natural products upon drug discovery. Nat Prod Rep. Jun. 2000;17(3):215-34.
Nielsen et al., Crystal structure of a bacterial class 2 histone deacetylase homologue. J Mol Biol. Nov. 18, 2005;354 (1):107-20. Epub Oct. 7, 2005.
Notterpek et al., PMP22 accumulation in aggresomes: implications for CMT1A pathology. Neurobiol Dis. Oct. 1999;6 (5):450-60.
O'Connor et al., Developing new drugs for the treatment of lymphoma. European Journal of Haematology. 2005;75:150-58.
Ohlmeyer et al., Complex synthetic chemical libraries indexed with molecular tags. Proc Natl Acad Sci U S A. Dec. 1, 1993;90(23):10922-6.
Parra et al., Protein kinase D1 phosphorylates HDAC7 and induces its nuclear export after T-cell receptor activation J Biol Chem. Apr. 8, 2005;280(14):13762-70. Epub Dec. 28, 2004.
Patel et al., Identification and characterization of small molecule inhibitors of a class I histone deacetylase from Plasmodium falciparum. J Med Chem. Apr. 23, 2009;52(8):2185-7.
Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.
Presbitero et al., Drug-eluting stents do they make the difference? Minerva Cardioangiol. Oct. 2002;50(5):431-42. Italian.
Pyne et al., Reactions of Lithiated N-Tosyl S-Phenyl S-2-Propenyl Sulfoximine with Aldehydes. Sulfur Letters. 1997;20 (6):255-60.
Raje et al., Combination of the mTOR inhibitor rapamycin and CC-5013 has synergistic activity in multiple myeloma. Blood. Dec. 15, 2004;104(13):4188-93. Epub Aug. 19, 2004.
Renthal et al., Histone deacetylase 5 epigenetically controls behavioral adaptations to chronic emotional stimuli. Neuron. Nov. 8, 2007;56(3):517-29.
Richardson et al., A phase 2 study of bortezomib in relapsed, refractory myeloma. N Engl J Med. Jun. 26, 2003;348 (26):2609-17.
Riester et al., Members of the histone deacetylase superfamily differ in substrate specificity towards small synthetic substrates. Biochem Biophys Res Commun. Nov. 19, 2004;324(3):1116-23.
Rosato et al., Histone deacetylase inhibitors in clinical development. Expert Opin Investig Drugs. Jan. 2004;13 (1):21-38.
Ruygrok et al., Rapamycin in cardiovascular medicine. Intern Med J. Mar. 2003;33(3):103-9.
Saitou et al., The neighbor-joining method: a new method for reconstructing phylogenetic trees. Mol Biol Evol. Jul. 1987;4(4):406-25.
Schreiber, Chemical genetics resulting from a passion for synthetic organic chemistry. Bioorg Med Chem. Aug. 1998;6 (8):1127-52.
Schreiber, Target-oriented and diversity-oriented organic synthesis in drug discovery. Science. Mar. 17, 2000;287 (5460):1964-9.
Schreiber, Using the Principles of Organic Chemistry to Explore Cell Biology. Chem and Eng News. 1992; 70(43): 22-32.
Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.
Secrist et al., HDAC inhibitors for the treatment of cancer. Curr Opin Investig Drugs Dec. 2003;4(12):1422-7.
Serrador et al., HDAC6 deacetylase activity links the tubulin cytoskeleton with immune synapse organization. Immunity. Apr. 2004;20(4):417-28.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7):1325-34.
Stamatakis et al., A rapid bootstrap algorithm for the RAxML Web servers. Syst Biol. Oct. 2008;57(5):758-71.
Sternson et al., Split-pool synthesis of 1,3-dioxanes leading to arrayed stock solutions of single compounds sufficient for multiple phenotypic and protein-binding assays. J Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett Dec. 27, 2001;3(26):4239-42.
Stevanovic et al., Natural and Synthetic Peptide Pools: Characterization by Sequencing and Electrospray Mass Spectrometry. Bioorg Med Chem Lett 1993;3(3):431-36.

(56) References Cited

OTHER PUBLICATIONS

Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.

* cited by examiner

Esterases in human and mouse plasma

| Esterase | Human plasma (mg/l) | Mouse plasma (mg/l) |
| --- | --- | --- |
| BChE (EC 3.1.1.8) | 5 | 2.6 |
| AChE (EC 3.1.1.7) | 0.008 | 0.2 |
| PON1 (EC 3.1.8.1) | 50 | 25 |
| Albumin | 50000–60000 | 50000–60000 |
| Carboxylesterase (EC 3.1.1.1) | 0 | 80 |

FIG. 1

HISTONE DEACETYLASE INHIBITORS

RELATED APPLICATIONS

This application is a continuation of U.S. patent application Ser. No. 14/862,679, filed on Sep. 23, 2015, which is a continuation of U.S. patent application Ser. No. 14/198,764, filed on Mar. 6, 2014, which is a continuation of U.S. patent application Ser. No. 13/944,320, filed on Jul. 17, 2013, which is a continuation of Ser. No. 13/678,983, filed Nov. 16, 2012, which is a continuation of U.S. patent application Ser. No. 12/279,398, filed on Oct. 19, 2009, now U.S. Pat. No. 8,383,855, issued on Feb. 26, 2013, which is a national phase application under 35 U.S.C. § 371 of PCT International Application No. PCT/US2007/062152, filed on Feb. 14, 2007, which claims priority under 35 U.S.C. § 119(e) to U.S. provisional patent application, U.S. Ser. No. 60/773,172, filed Feb. 14, 2006. Each of these prior applications is incorporated herein by reference.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules can be used to alter the function of biological molecules to which they bind, these molecules have been useful at elucidating signal transduction pathways by acting as chemical protein knockouts, thereby causing a loss of protein function (Schreiber et al., *J. Am. Chem. Soc.*, 1990, 112, 5583; Mitchison, *Chem. and Biol.*, 1994, 1, 3). Additionally, due to the interaction of these small molecules with particular biological targets and their ability to affect specific biological function, they may also serve as candidates for the development of therapeutics. One important class of small molecules, natural products, which are small molecules obtained from nature, clearly have played an important role in the development of biology and medicine, serving as pharmaceutical leads, drugs (Newman et al., *Nat. Prod. Rep.* 2000, 17, 215-234), and powerful reagents for studying cell biology (Schreiber, S. L. *Chem. and Eng. News* 1992 (October 26), 22-32).

Because it is difficult to predict which small molecules will interact with a biological target, and it is oftent difficult to obtain and synthesize efficiently small molecules found in nature, intense efforts have been directed towards the generation of large numbers, or libraries, of small organic compounds, often "natural product-like" libraries. These libraries can then be linked to sensitive screens for a particular biological target of interest to identify the active molecules.

One biological target of recent interest is histone deacetylase (see, for example, a discussion of the use of inhibitors of histone deacetylases for the treatment of cancer: Marks et al. *Nature Reviews Cancer* 2001, 1, 194; Johnstone et al. *Nature Reviews Drug Discovery* 2002, 1, 287). Post-translational modification of proteins through acetylation and deacetylation of lysine residues has a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621-1625). Eleven human HDACs, which use Zn as a cofactor, have been characterized (Taunton et al. *Science* 1996, 272, 408-411; Yang et al. *J. Biol. Chem.* 1997, 272, 28001-28007; Grozinger et al. *Proc. Natl. Acad. Sci. U.S.A.* 1999, 96, 4868-4873; Kao et al. *Genes Dev.* 2000, 14, 55-66; Hu et al. *J. Biol. Chem.* 2000, 275, 15254-15264; Zhou et al. *Proc. Natl. Acad. Sci. U.S.A.* 2001, 98, 10572-10577; Venter et al. *Science* 2001, 291, 1304-1351). These members fall into three related classes (class I, II, and III). An additional seven HDACs have been identified which use NAD as a confactor. To date, no small molecules are known that selectively target either the two classes or individual members of this family ((for example ortholog-selective HDAC inhibitors have been reported: (a) Meinke et al. *J. Med. Chem.* 2000, 14, 4919-4922; (b) Meinke, et al. *Curr. Med. Chem.* 2001, 8, 211-235).

SUMMARY OF THE INVENTION

The present invention provides novel histone deacetylase inhibitors and methods of preparing and using these compounds. The inventive HDAC inhibitors comprise an esterase-sensitive ester linkage, thereby when the compound is exposed to an esterase such as in the bloodstream the compound is inactivated. The compounds are particularly useful in the treatment of skin disorders such as cutaneous T-cell lymphoma, neurofibromatosis, psoriasis, hair loss, dermatitis, baldness, and skin pigmentation. The inventive compound is administered topically to the skin of the patient where it is clinically active. Once the compound is absorbed into the body, it is quickly inactivated by esterases which cleave the compound into two or more biologically inactive fragments. Thus, allowing for high local concentrations (e.g., in the skin) and reduced systemic toxicity. In certain embodiments, the compound is fully cleaved upon exposure to serum in less than 5 min., preferably less than 1 min.

The present invention provides novel compounds of general formula (I),

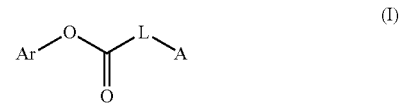

and pharmaceutical compositions thereof, as described generally and in subclasses herein, which compounds are useful as inhibitors of histone deacetylases or other deacetylases, and thus are useful for the treatment of proliferative diseases. The inventive compounds are additionally useful as tools to probe biological function. In certain embodiments, the compounds of the invention are particularly useful in the treatment of skin disorders. The ester linkage is susceptible to esterase cleavage, particularly esterases found in the blood. Therefore, these compounds may be administered topically to treat skin disorders, such as cutaneous T-cell lymphoma, psoriasis, hair loss, dermatitis, etc., without the risk of systemic effects. Once the compound enters the bloodstream it is quickly degraded by serum esterases. Preferably, the compound is degraded into non-toxic, biologically inactive by-products.

In another aspect, the present invention provides methods for inhibiting histone deacetylase activity or other deacetylase activity in a patient or a biological sample, comprising administering to said patient, or contacting said biological sample with an effective inhibitory amount of a compound of the invention. In certain embodiments, the compounds specifically inhibit a particular HDAC (e.g., HDAC1, HDAC2, HDAC3, HDAC4, HDAC4, HDAC5, HDAC6, HDAC7, HDAC8, HDAC9, HDAC10, HDAC11) or class of HDACs (e.g., Class I, II, or III). In certain embodiments, the compounds specifically inhibit HDAC6. In still another aspect, the present invention provides methods for treating skin disorders involving histone deacetylase activity, comprising administering to a subject in need thereof a therapeutically effective amount of a compound of the invention. The compounds may be administered by any method known in the art. In certain embodiments, the compounds are administered topically (e.g., in a cream, lotion, ointment, spray, gel, powder, etc.). In certain embodiments, the compound is administered to skin. In other certain embodiments, the compound is administered to hair. The compounds may also be administered intravenously or orally. The invention also provides pharmaceutical compositions of the compounds wherein the compound is combined with a pharmaceutically acceptable excipient.

In yet another aspect, the present invention provides methods for preparing compounds of the invention and intermediates thereof.

Definitions

Certain compounds of the present invention, and definitions of specific functional groups are also described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group," has used herein, it is meant that a particular functional moiety, e.g., C, O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401-8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "acyl", as used herein, refers to a carbonyl-containing functionality, e.g., —C(=O)R', wherein R' is an aliphatic, alycyclic, heteroaliphatic, heterocyclic, aryl, heteroaryl, (aliphatic)aryl, (heteroaliphatic)aryl, heteroaliphatic (aryl) or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$— cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least on heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl) aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6-, or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein. The terms "halo" and "halogen" as used herein refer to an atom selected from fluorine, chlorine, bromine and iodine.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical consisting solely of carbon and hydrogen atoms, having from one to n carbon atoms, having a free valence "-" at both ends of the radical.

The term "alkenylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as double bonds and wherein a double bond can exist between the first carbon of the chain and the rest of the molecule.

The term "alkynylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as triple bonds and wherein a triple bond can exist between the first carbon of the chain and the rest of the molecule.

Unless otherwise indicated, as used herein, the terms "alkyl", "alkenyl", "alkynyl", "heteroalkyl", "heteroalkenyl", "heteroalkynyl", "alkylidene", alkenylidene", -(alkyl)aryl, -(heteroalkyl)aryl, -(heteroalkyl)aryl, -(heteroalkyl)heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic, "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Pharmaceutically acceptable derivatives also include "reverse pro-drugs." Reverse pro-drugs, rather than being activated, are inactivated upon absorption. For example, as discussed herein, many of the ester-containing compounds of the invention are biologically active but are inactivated upon exposure to certain physiological environments such as a blood, lymph, serum, extracellular fluid, etc. which contain esterase activity. The biological activity of reverse pro-drugs and pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives will be discussed in more detail herein below.

The term "linker," as used herein, refers to a chemical moiety utilized to attach one part of a compound of interest to another part of the compound. Exemplary linkers are described herein.

Unless indicated otherwise, the terms defined below have the following meanings:

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other preferred embodiments, natural-product-like small molecules are utilized.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Metal chelator": As used herein, the term "metal chelator" refers to any molecule or moiety that is is capable of forming a complex (i.e., "chelates") with a metal ion. In certain exemplary embodiments, a metal chelator refers to to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, $Ca^{2+}$, $Fe^{3+}$, $Zn^{2+}$, $Na^{+}$, etc. In certain embodiments, the metal chelator binds $Zn^{2+}$. In certain embodiments, molecules of moieties that precipitate metal ions are not considered to be metal chelators.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

BRIEF DESCRIPTION OF THE DRAWING

FIG. 1 includes a table of esterases found in human and mouse plasma.

FIG. 2 shows the design of a reverse pro-drug version of SAHA-SAHP.

FIG. 3 illustrates the stability of SAHA (with an amide) in PBS.

FIG. 4 illustrates the stability of SAHA in serum.

FIG. 5 shows the stability of SAHP (ester instead of amdie) in PBS.

FIG. 6 shows the degradation of SAHP in serum. In less than 15 minutes, SAHP is completely degraded.

FIG. 7 shows a more detailed study of the degradation of SAHP in serum. In less than 2 minutes, SAHP is completely degraded into phenol and the corresponding carboxylic acid.

FIG. 8 shows the degradation of SAHP by human serum under various conditions.

FIG. 9 shows the degradation of SAHP by recombinant paraoxonase.

FIG. 10 shows the degradation of SAHP in RPMI media with 10% FBS.

FIG. 11 shows the effect of SAHA v. SAHP on lysine acetylation.

FIG. 12 shows the stability of SAHP in an olive oil/acetone formulation for murine model.

FIG. 13 is an exemplary synthetic scheme for preparing SAHP.

Figure 14:
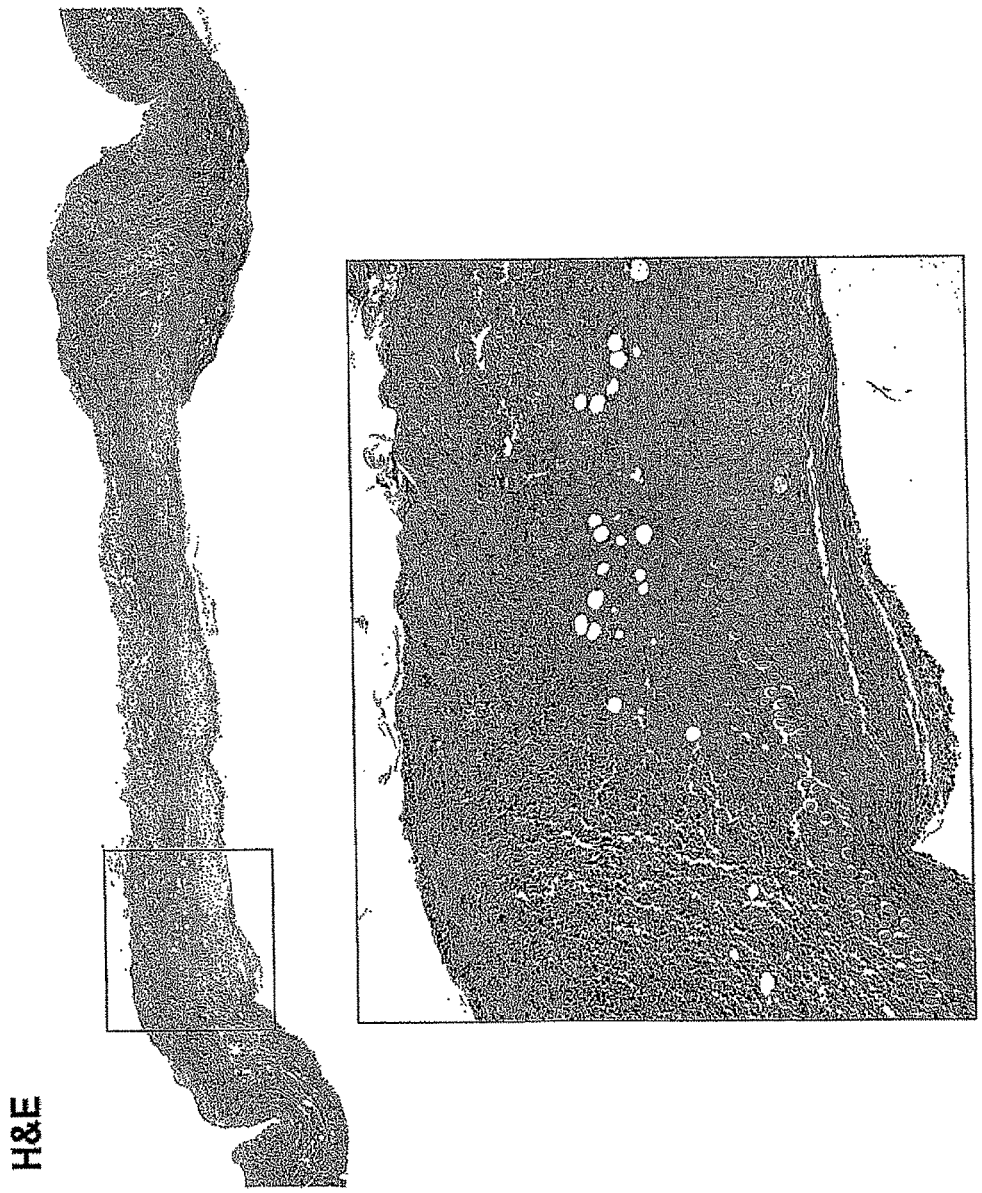

FIG. 14. Interleukin-7 is a growth factor for T-cell development, in particular the gamma-delta subset. Transgenic mice overexpressing IL-7 in keratinocytes were developed by the laboratories of Thomas Kupper and Benjamin Rich, using a tissue-specific keratin-14 promoter element. These mice have been reported to develop a characteristic lymphoproliferative skin disease grossly and histologically similar to human cutaneous T-cell lymphoma (CTCL). Transformed lymphocytes derived from involved skin were passaged ex vivo and injected into syngeneic (non-transgenic) mice. After fourteen days, these mice develop a homogeneous lymphoproliferative disease. Two cohorts of five mice were included in a prospective study of topical, daily suberoyl hydroxamic acid phenyl ester (SAHP, also known as SHAPE) versus vehicle control. After fourteen days of therapy, mice were sacrificed and the treated region was dissected for histopathologic examination. In SHAPE-treated mice, hematoxylin-eosin staining demonstrates a marked reduction in lymphomatous infiltration within the treated window. Vehicle control mice failed to demonstrate a cytotoxic response.

Figure 15:
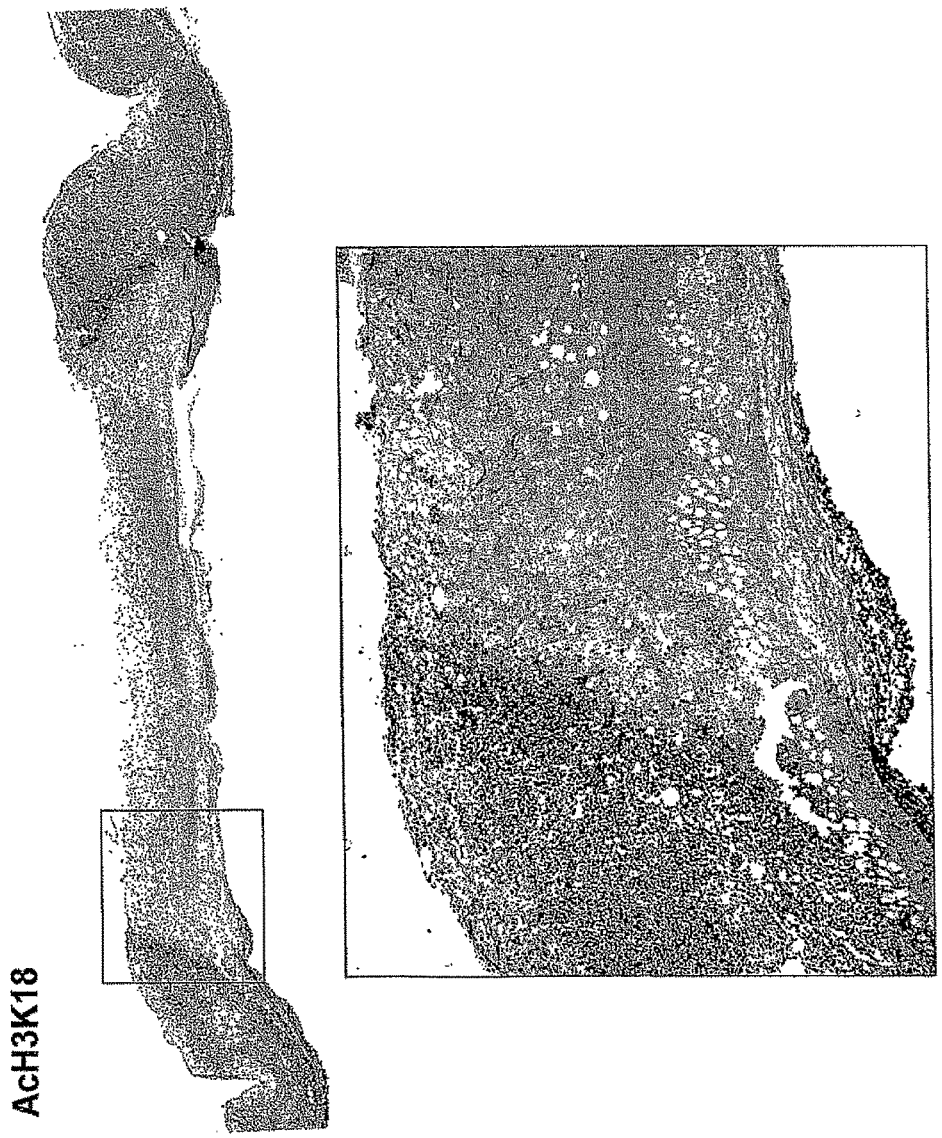

FIG. 15 shows the pharmacodynamic effect of SAHP treatment as assessed using immunohistochemical staining for acetylated histones compared to vehicle treated controls. In SAHP-treated mice, AcH3K18 staining demonstrates hyperacetylated histone staining at the margin of compound treatment, with absent nuclear staining in the region of drug response. Vehicle control mice failed to demonstrate an increase in histone hyperacetylation.

DETAILED DESCRIPTION OF THE INVENTION

As discussed above, there remains a need for the development of novel histone deacetylase inhibitors. The present invention provides novel compounds of general formula (I), and methods for the synthesis thereof, which compounds are useful as inhibitors of histone deacetylases, and thus are useful for the treatment of proliferative diseases, particularly proliferative or other disorders associated with the skin and/or hair. In particular, the inventive compounds comprise an ester linkage. The ester linkage is preferably sensitive to esterase cleavage; therefore, when the compound is contacted with an esterase it is deactivated.

Compounds of the Invention

As discussed above, the present invention provides a novel class of compounds useful for the treatment of cancer and other proliferative conditions related thereto. In certain embodiments, the compounds of the present invention are useful as inhibitors of histone deacetylases and thus are useful as anticancer agents, and thus may be useful in the treatment of cancer, by effecting tumor cell death or inhibiting the growth of tumor cells. In certain exemplary embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the inventive compounds are active against cutaneous T-cell lymphoma. Additionally, as described above and in the exemplification, the inventive compounds may also be useful in the treatment of protozoal infections. In certain exemplary embodiments, the compounds of the invention are useful for disorders resulting from histone deacetylation activity. In certain embodiments, the compounds are useful for skin disorders. Exemplary skin disorders that may be treated using the inventive compounds include cutaneous T-cell lymphoma (CTCL), skin cancers (e.g., squamous cell carcinoma, basal cell carcinoma, malignant melanoma, etc.), psoriasis, hair loss, dermatitis, neurofibromatosis, disorders associated with skin hyperpigmentation, etc.

Compounds of this invention comprise those, as set forth above and described herein, and are illustrated in part by the various classes, subgenera and species disclosed elsewhere herein.

In general, the present invention provides compounds having the general structure (I):

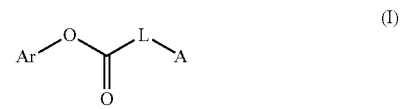

and pharmaceutically acceptable salts and derivatives thereof;
wherein
A comprises a functional group that inhibits histone deacetylase;
L is a linker moiety; and
Ar is a substituted or unsubstituted aryl or heteroaryl moiety; substituted or unsubstituted, branched or unbranched arylaliphatic or heteroarylaliphatic moiety; a substituted or unsubstituted cyclic or heterocyclic moiety; substituted or unsubstituted, branched or unbranched cyclicaliphatic or heterocyclicaliphatic moiety.

In certain embodiments, A comprises a metal chelating functional group. For example, A comprises a $Zn^{2+}$ chelating group. In certain embodiments, A comprises a functional group selected group consisting of:

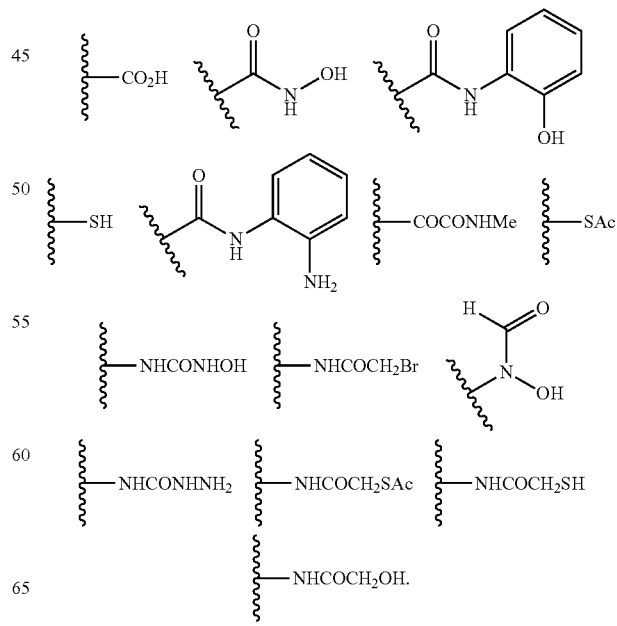

In certain embodiments, A comprises hydroxamic acid

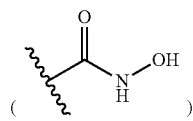

or a salt thereof. In other embodiments, A comprises the formula:

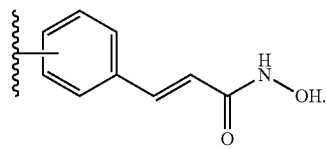

In certain particular embodiments, A comprises the formula:

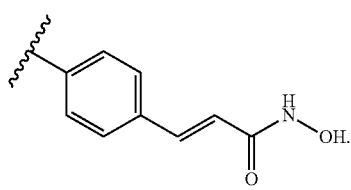 [SMILES: *c1ccc(/C=C/C(=O)NO)cc1]

In other embodiments, A comprises a carboxylic acid (—CO$_2$H). In other embodiments, A comprises an o-aminoanilide

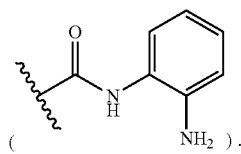

In other embodiments, A comprises an o-hydroxyanilide

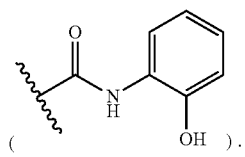 [SMILES: *C(=O)Nc1ccccc1O]

In yet other embodiments, A comprises a thiol (—SH).

In certain embodiments, Ar is arylaliphatic. In other embodiments, Ar is heteroarylaliphatic. In certain embodiments, Ar is a substituted or unsubstituted aryl moiety. In certain embodiments, Ar is a monocyclic, substituted or unsubstituted aryl moiety, preferably a five- or six-membered aryl moiety. In other embodiments, Ar is a bicyclic, substituted or unsubstituted aryl moiety. In still other embodiments, Ar is a tricyclic, substituted or unsubstituted aryl moiety. In certain embodiments, Ar is a substituted or unsubstituted phenyl moiety. In certain embodiments, Ar is an unsubstituted phenyl moiety. In other embodiments, Ar is a substituted phenyl moiety. In certain embodiments, Ar is a monosubstituted phenyl moiety. In certain particular embodiments, Ar is an ortho-substituted Ar moiety. In certain particular embodiments, Ar is an meta-substituted Ar moiety. In certain particular embodiments, Ar is an para-substituted Ar moiety. In certain embodiments, Ar is a disubstituted phenyl moiety. In certain embodiments, Ar is a trisubstituted phenyl moiety. In certain embodiments, Ar is a tetrasubstituted phenyl moiety. In certain embodiments, Ar is a substituted or unsubstituted cyclic or heterocyclic.

In certain embodiments, Ar is a substituted or unsubstituted heteroaryl moiety. In certain embodiments, Ar is a monocyclic, substituted or unsubstituted heteroaryl moiety, preferably a five- or six-membered heteroaryl moiety. In other embodiments, Ar is a bicyclic, substituted or unsubstituted heteroaryl moiety. In still other embodiments, Ar is a tricyclic, substituted or unsubstituted heteroaryl moiety. In certain embodiments, Ar comprises N, S, or O. In certain embodiments, Ar comprises at least one N. In certain embodiments, Ar comprises at least two N.

In certain embodiments, Ar is:

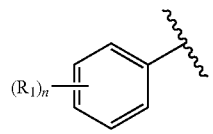

wherein n is an integer between 1 and 5, inclusive; preferably, between 1 and 3, inclusive; more preferably, 1 or 2;

$R_1$ is is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHR$_A$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, Ar is

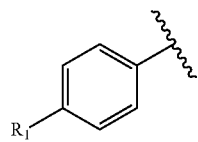

In other embodiments, Ar is

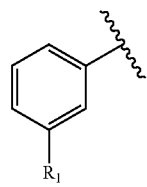

In yet other embodiments, Ar is

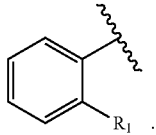

In certain embodiments, $R_1$ is —$N(R_A)_2$, wherein $R_A$ is hydrogen or $C_1$-$C_6$ alkyl. In certain embodiments, $R_1$ is —$OR_A$, wherein $R_A$ is hydrogen or $C_1$-$C_6$ alkyl. In certain particular embodiments, $R_1$ is —OMe. In certain embodiments, $R_1$ is branched or unbranched acyl. In certain embodiments, $R_1$ is —O(=O)$OR_A$. In certain embodiments, $R_1$ is —C(=O)$OR_A$, wherein $R_A$ is hydrogen or $C_1$-$C_6$ alkyl. In certain embodiments, $R_1$ is —C(=O)$NH_2$. In certain embodiments, $R_1$ is —NHC(=O)$R_A$. In certain embodiments, $R_1$ is —NHC(=O)$R_A$, wherein $R_A$ is hydrogen or $C_1$-$C_6$ alkyl. In certain embodiments, $R_1$ is halogen. In certain embodiments, $R_1$ is $C_1$-$C_6$ alkyl.

In certain particular embodiments, Ar is a substituted phenyl moiety of formula:

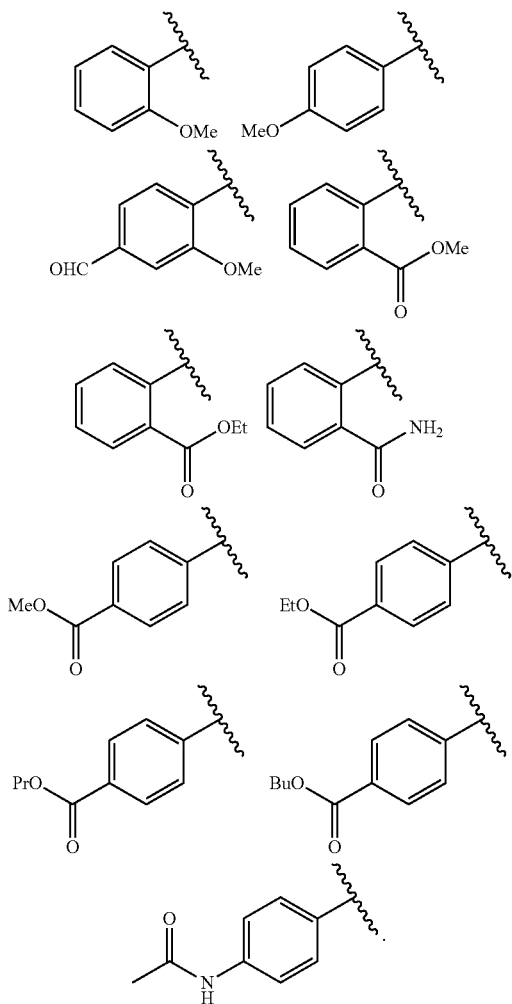

In certain embodiments, Ar is chosen from one of the following:

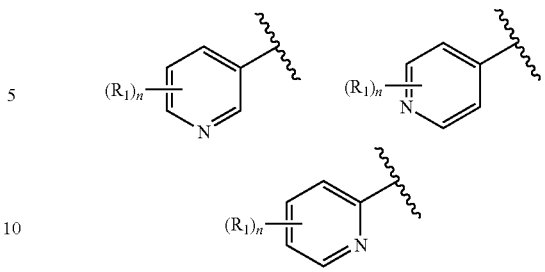

wherein n is an integer between 1 and 4, inclusive; preferably, between 1 and 3, inclusive; more preferably, 1 or 2;

$R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N(R_A)_2$; —$NHR_A$; —NHC(O)$R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, Ar is chosen from one of the following:

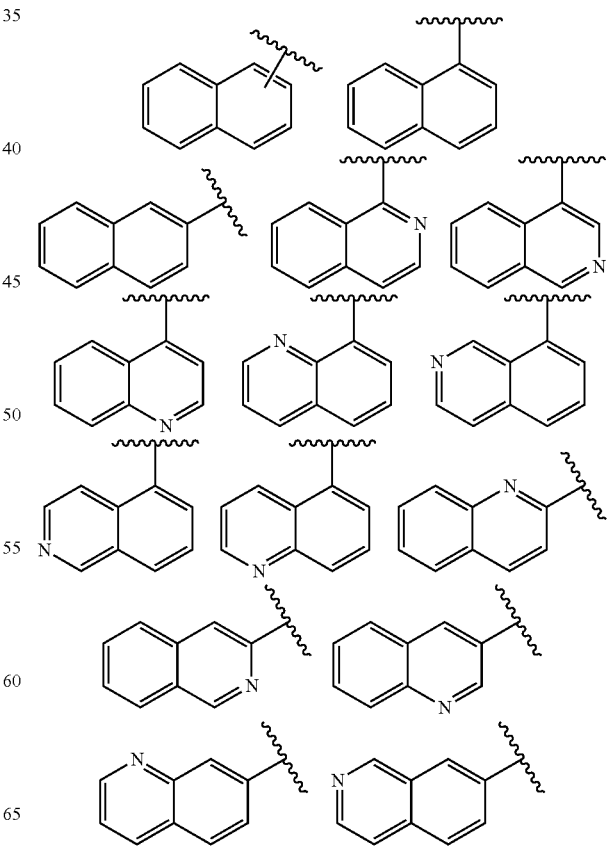

-continued

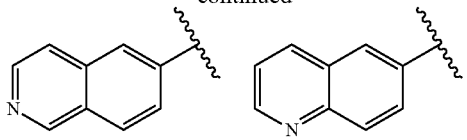

Any of the above bicyclic ring system may be substituted with up to seven $R_1$ substituents as defined above.

In certain embodiments, L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety. In certain embodiments, L is a substituted or unsubstituted, cyclic or acyclic, branched or unbranched aliphatic moiety. In certain embodiments, L is $C_1$-$C_{20}$ alkylidene, preferably $C_1$ to $C_{12}$ alkylidene, more preferably $C_4$-$C_7$ alkylidene. In certain embodiments, L is $C_1$-$C_{20}$ alkenylidene, preferably $C_1$ to $C_{12}$ alkenylidene, more preferably $C_4$-$C_7$ alkenylidene. In certain embodiments, L is $C_1$-$C_{20}$ alkynylidene, preferably $C_1$ to $C_{12}$ alkynylidene, more preferably $C_4$-$C_7$ alkynylidene. In certain embodiments, L is a a substituted or unsubstituted, cyclic or acyclic, branched or unbranched heteroaliphatic moiety. In certain embodiments, L comprises a cyclic ring system, wherein the rings may be aryl, heteroaryl, non-aromatic carbocyclic, or non-aromatic heterocyclic. In still other embodiments, L comprises a substituted or unsubstituted heteroaryl moiety. In certain particular embodiments, L comprises a phenyl ring. In certain embodiments, L comprises multiple phenyl rings (e.g., one, two, three, or four phenyl rings).

In certain embodiments, L is

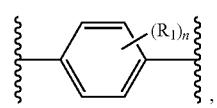

wherein n is an integer between 1 and 4, inclusive; preferably, between 1 and 3, inclusive; more preferably, 1 or 2; and $R_1$ is is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —N($R_A$)$_2$; —NH$R_A$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, L is

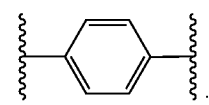

In certain embodiments, L is

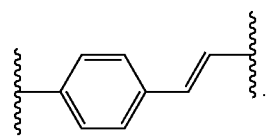 [SMILES: */C=C/c1ccc(*)cc1]

In certain embodiments, L is an unbranched, unsubstituted, acyclic alkyl chain. In certain embodiments, L is

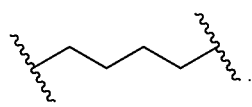 [SMILES: *CCCC*]

In other embodiments, L is

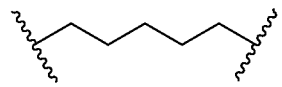

In certain other embodiments, L is

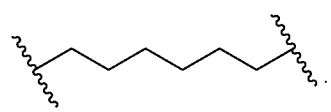 [SMILES: *CCCCCC*]

In other embodiments, L is

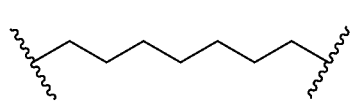

In yet other embodiments, L is

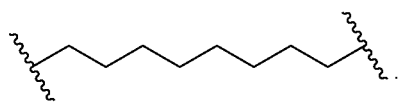 [SMILES: *CCCCCCCC*]

In certain embodiments, L is a substituted, acyclic aliphatic chain. In certain embodiments, L is

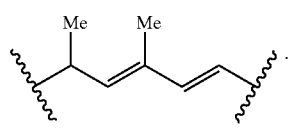 [SMILES: */C=C/C(C)=C/C(*)C]

In certain embodiments, L is an unbranched, unsubstituted, acyclic heteroaliphatic chain. In certain particular embodiments, L is

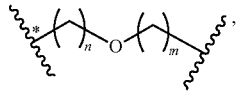

wherein n is an integer between 0 and 10, inclusive; preferably, between 0 and 5, inclusive; and m is an integer between 0 and 10, inclusive; preferably, between 0 and 5, inclusive. In certain particular embodiments, L is

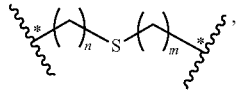

wherein n is an integer between 0 and 10, inclusive; preferably, between 0 and 5, inclusive; and m is an integer between 0 and 10, inclusive; preferably, between 0 and 5, inclusive. In certain particular embodiments, L is

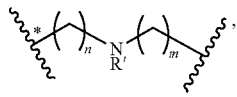

wherein n is an integer between 0 and 10, inclusive; preferably, between 0 and 5, inclusive; m is an integer between 0 and 10, inclusive; preferably, between 0 and 5, inclusive; and R' is hydrogen, $C_1$-$C_6$ aliphatic, heteroaliphatic, aryl, heteroaryl, or acyl. In certain particular embodiments, L is

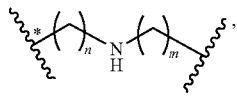

wherein n is an integer between 0 and 10, inclusive; preferably, between 0 and 5, inclusive; and m is an integer between 0 and 10, inclusive; preferably, between 0 and 5, inclusive.

In certain embodiments of the invention, compounds of formula (I) have the following structure as shown in formula (Ia):

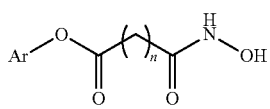

wherein n is an integer between 0 and 15, inclusive; preferably, between 0 and 10, inclusive; more preferably, between 1 and 8, inclusive; even more preferably, 4, 5, 6, 7, or 8; and Ar is defined as above. In certain embodiments, n is 5. In other embodiments, n is 6. In still other embodiments, n is 7.

In certain embodiments of the invention, compounds of formula (I) have the following structure as shown in formula (Ib):

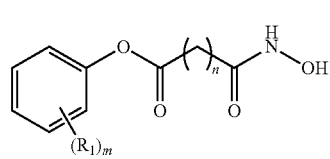

wherein n is an integer between 0 and 15, inclusive; preferably, between 0 and 10, inclusive; more preferably, between 1 and 8, inclusive; even more preferably, 4, 5, 6, 7, or 8;

m is an integer between 1 and 5, inclusive; preferably, m is 1, 2, or 3; and $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_1$ is hydrogen, halogen, hydroxy, amino, alkylamino, dialkylamino, nitroso, acyl, or $C_1$-$C_6$ alkyl. In certain embodiments, $R_1$ is aryl. In certain embodiments, $R_1$ is a multicyclic aryl moiety. In other embodiments, $R_1$ is heteroaryl. In certain embodiments, $R_1$ is carbocyclic. In other embodiments, $R_1$ is heterocyclic. In certain embodiments $R_1$ comprises a 1,3-dioxane ring optionally substituted. In certain embodiments, n is 5. In other embodiments, n is 6. In still other embodiments, n is 7. In certain embodiments, m is 0. In other embodiments, m is 1. In still other embodiments, m is 2.

In certain embodiments of the invention, compounds of formula (I) are of the formula (Ic):

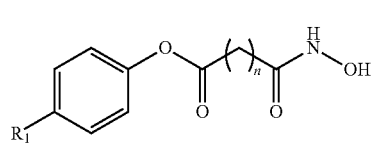

wherein n is an integer between 0 and 15, inclusive; preferably, between 0 and 10, inclusive; more preferably, between 1 and 8, inclusive; even more preferably, 4, 5, 6, 7, or 8; and $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_1$ is hydrogen, halogen, hydroxy, amino, alkylamino, dialkylamino, nitroso, acyl, or $C_1$-$C_6$ alkyl. In certain embodiments, $R_1$ is aryl. In other embodiments, $R_1$ is heteroaryl. In certain embodiments, $R_1$ is carbocyclic. In other embodiments, $R_1$ is heterocyclic. In certain embodiments, n is 5. In other embodiments, n is 6. In still other embodiments, n is 7.

In certain embodiments of the invention, compounds of formula (I) are of the formula (Id):

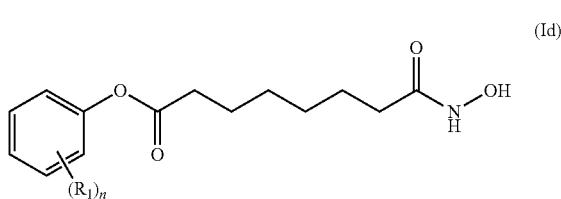

(Id)

wherein n is an integer between 1 and 5, inclusive; preferably, between 1 and 3; more preferably, 1 or 2; and $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_1$ is hydrogen, halogen, hydroxy, amino, alkylamino, dialkylamino, nitroso, acyl, or $C_1$-$C_6$ alkyl. In certain embodiments, $R_1$ is aryl. In other embodiments, $R_1$ is heteroaryl. In certain embodiments, $R_1$ is carbocyclic. In other embodiments, $R_1$ is heterocyclic. In certain embodiments, n is 1. In other embodiments, n is 2.

In certain embodiments of the invention, compounds of formula (I) are of the formula (Ie):

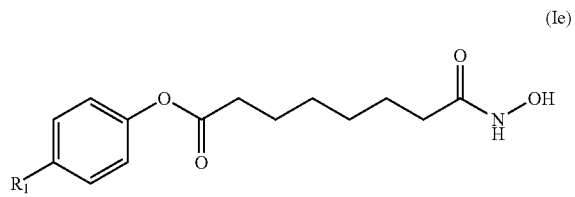

(Ie)

wherein R1 is defined as above.

In certain embodiments of the invention, compounds of formula (I) have the following stereochemistry and structure as shown in formula (If):

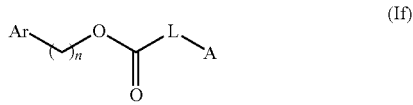

(If)

wherein A, L and Ar are defined as above; and n is an integer between 0 and 10, inclusive; preferably, between 0 and 5, inclusive; even more preferably, 0, 1, 2, or 3. In certain embodiments, Ar is phenyl.

In certain embodiments, compounds of formula (I) are of the formula (Ig):

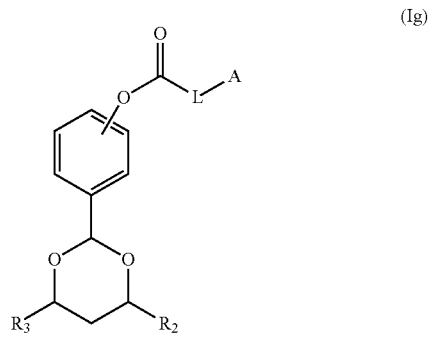

(Ig)

wherein

A and L are defined as above;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_2$ is —$CH_2$—$X(R_B)_n$, wherein X is O, S, N, or C, preferably O, S, or N; and n is 1, 2, or 3. In certain embodiments, $R_2$ is —$CH_2$—$OR_B$. In other embodiments, $R_2$ is —$CH_2$—$SR_B$. In yet other embodiments, $R_2$ is —$CH_2$—$R_B$. In other embodiments, $R_2$ is —$CH_2$—$N(R_B)_2$. In still other embodiments, $R_2$ is —$CH_2$—$NHR_B$. In certain embodiments of the invention, $R_B$ is one of:

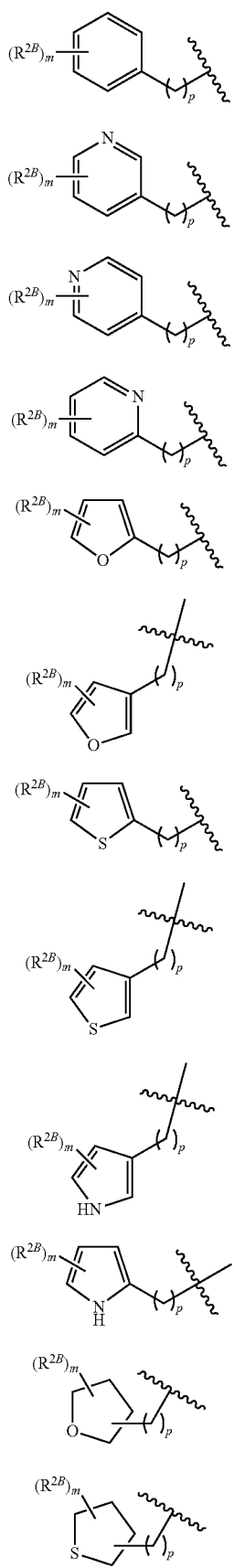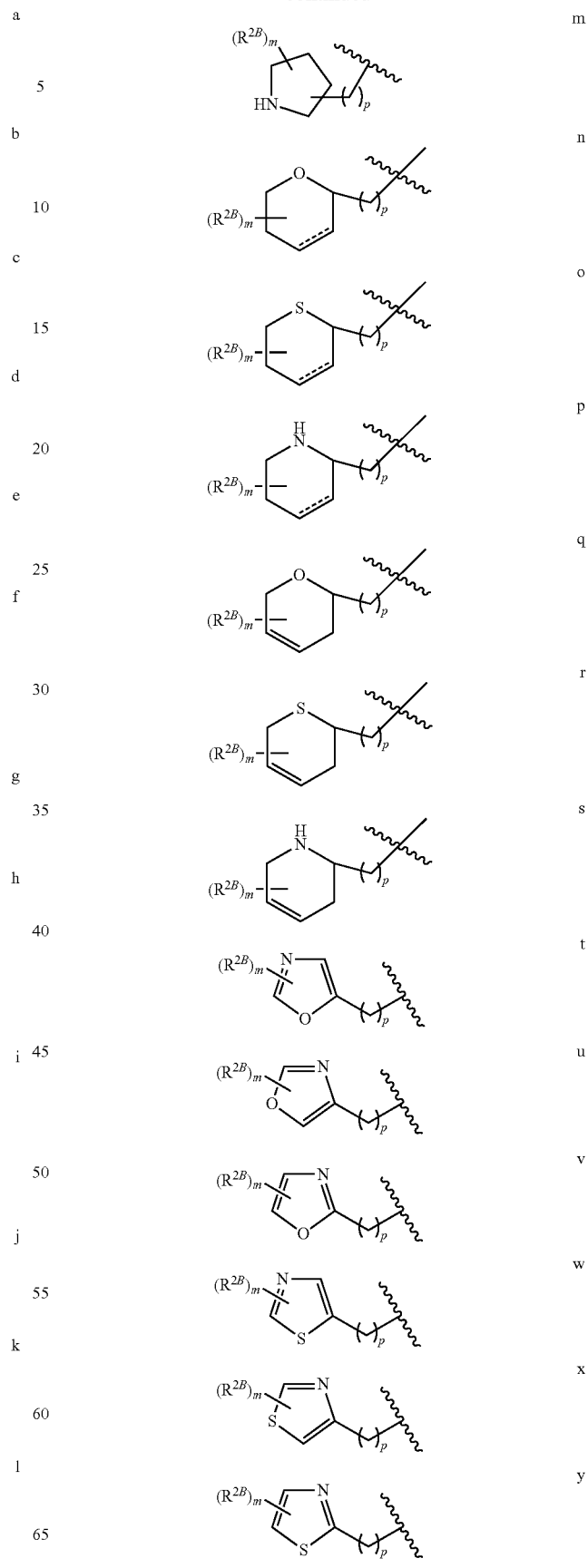

z

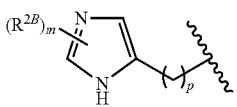

aa

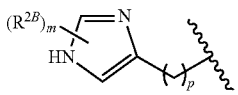

bb

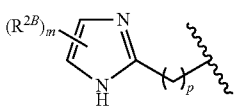

cc

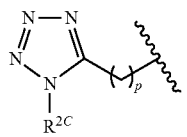

dd

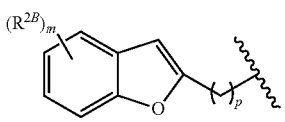

ee

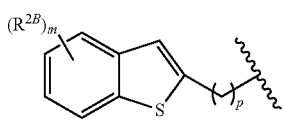

ff

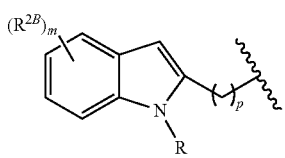
R = H, Alkyl gg

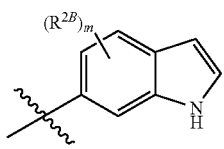

hh

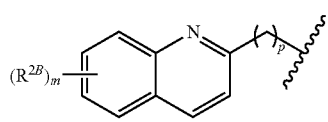

ii

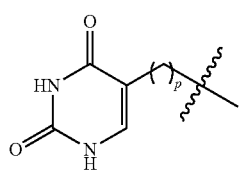

jj

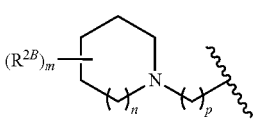
n = 0 or 1 kk

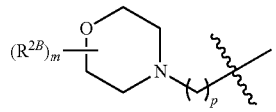

ll

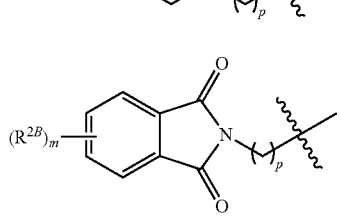

mm

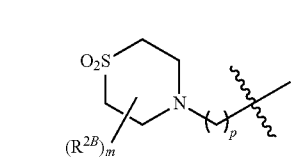

nn

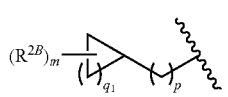

oo

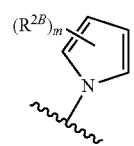

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O)—, —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

pp

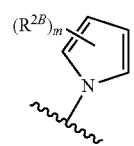

qq

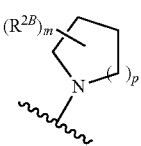

-continued

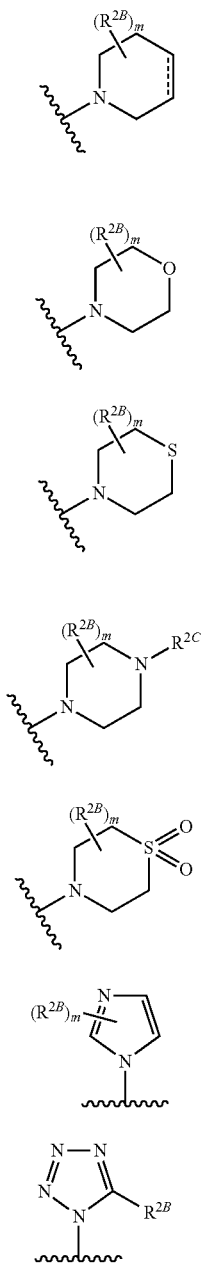

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X(R$_B$)$_n$ has one of the structures:

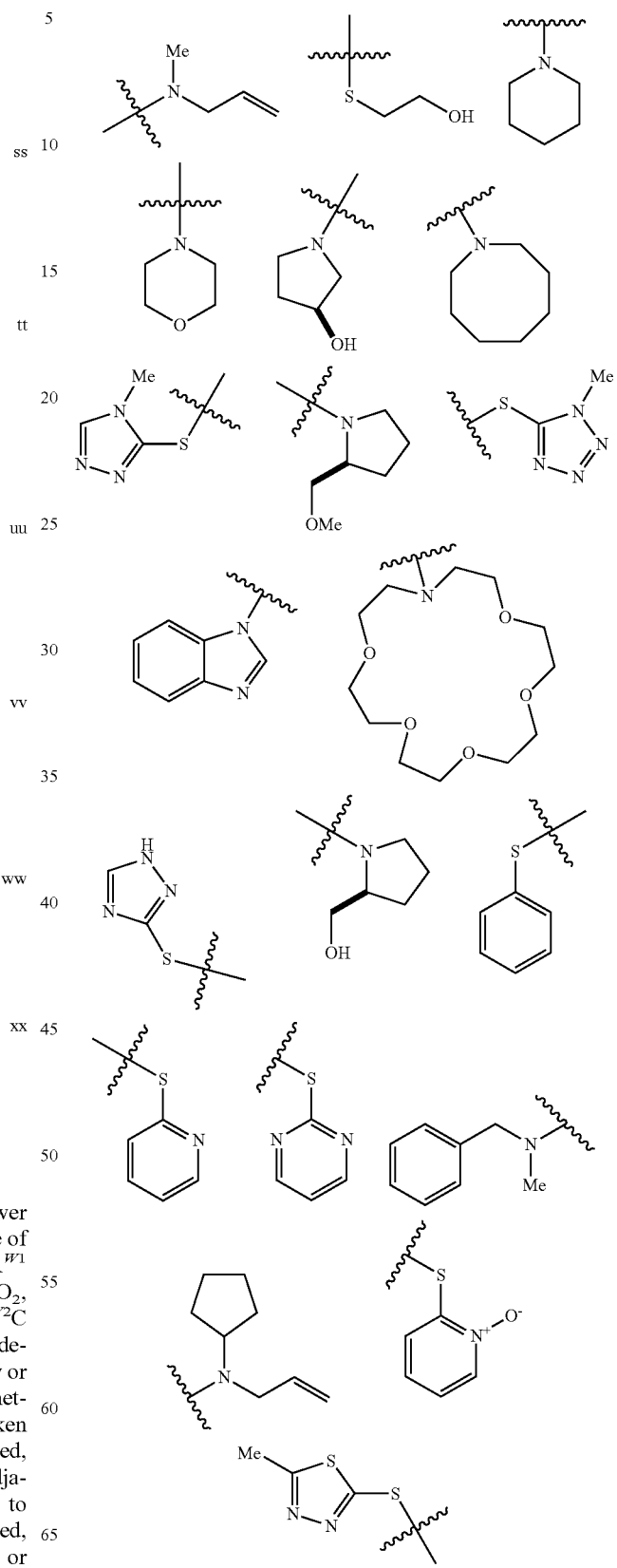

-continued
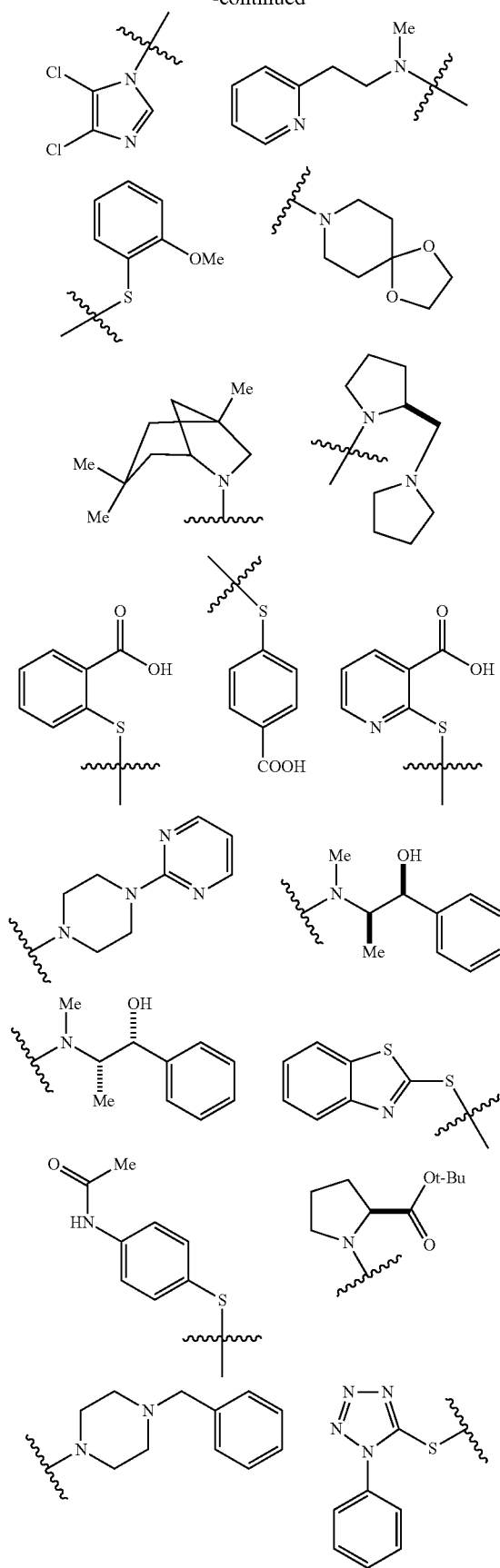
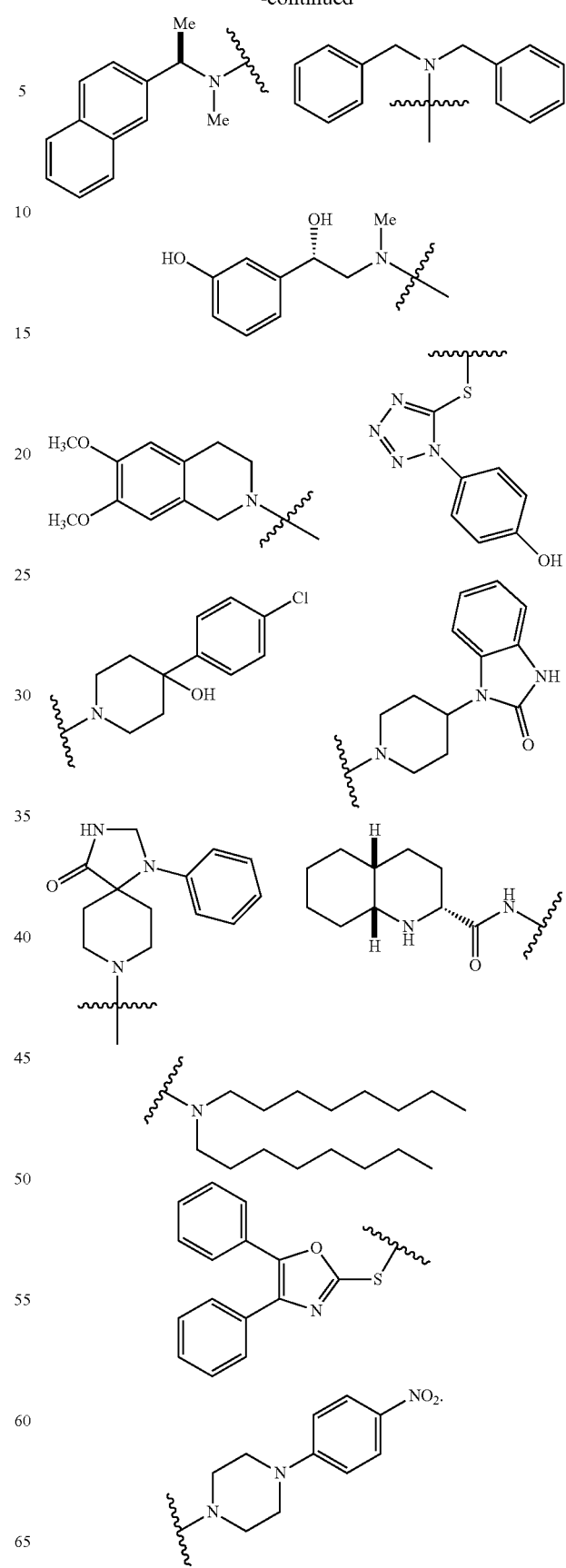

In certain embodiments, R₂ is

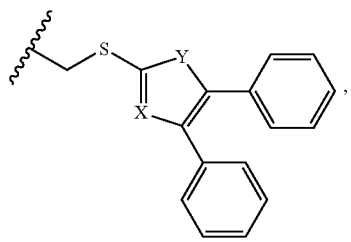

wherein X is N and Y is NH, S, or O. In other embodiments, R₂ is

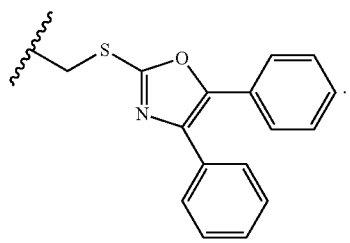 [SMILES: *CSc1nc(-c2ccccc2)c(-c2ccccc2)o1]

In certain embodiments, R₃ is substituted or unsubstituted aryl. In certain embodiments, R₃ is substituted or unsubstituted phenyl. In certain particular embodiments, R₃ is monosubstituted phenyl. In certain embodiments, R₃ is para-substituted phenyl. In certain embodiments, R₃ is

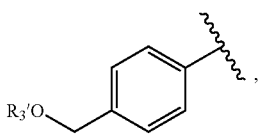

wherein R₃' is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, R₃ is

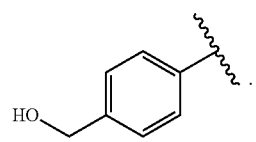

In other embodiments, R₃ is substituted or unsubstituted heteroaryl.

In certain embodiments, the stereochemistry of formula (Ig) is defined as follows:

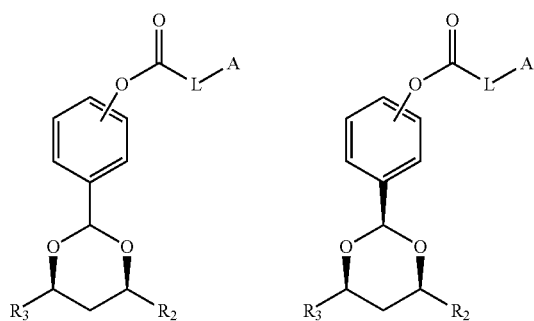

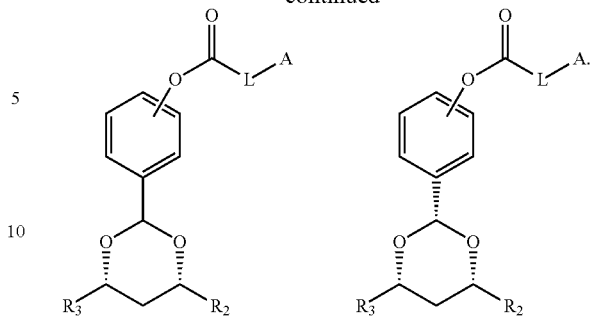

In certain embodiments of the invention, compounds of formula (I) are of the formula (Ih):

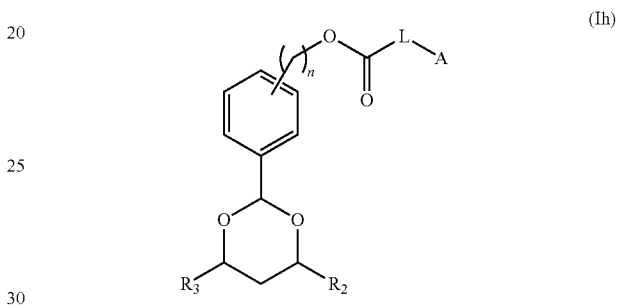

(Ih)

wherein
A and L are defined as above;
n is an integer between 0 and 10, inclusive; preferably, between 1 and 6, inclusive; more preferably, between 1 and 3, inclusive; and even more preferably, 0, 1, 2, or 3;
R₂ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO₂R$_B$; —CN; —SCN; —SR$_B$; —SOR$_B$; —SO₂R$_B$; —NO₂; —N(R$_B$)₂; —NHC(O)R$_B$; or —C(R$_B$)₃; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and
R₃ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO₂R$_C$; —CN; —SCN; —SR$_C$; —SOR$_C$; —SO₂R$_C$; —NO₂; —N(R$_C$)₂; —NHC(O)R$_C$; or —C(R$_C$)₃; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, R₂ is hydrogen. In other embodiments, R₂ is hydroxyl or a protected hydroxyl group. In certain embodiments, R₂ is alkoxy. In yet other embodiments, $R_2$ is a lower alkyl, alkenyl, or alkynyl group. In certain embodiments, $R_2$ is —CH$_2$—X(R$_B$)$_n$; wherein X is O, S, N, or C, preferably O, S, or N; and n is 1, 2, or 3. In certain embodiments, $R_2$ is —CH$_2$—OR$_B$. In other embodiments, $R_2$ is —CH$_2$—SR$_B$. In yet other embodiments, $R_2$ is —CH$_2$—R$_B$. In other embodiments, $R_2$ is —CH$_2$—N(R$_B$)$_2$. In still other embodiments, $R_2$ is —CH$_2$—NHR$_B$. In certain embodiments of the invention, R$_B$ is one of:

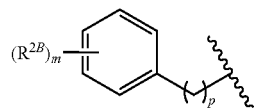
a

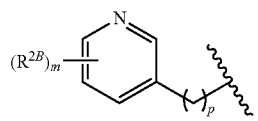
b

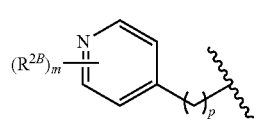
c

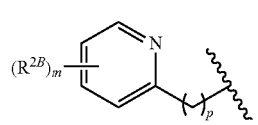
d

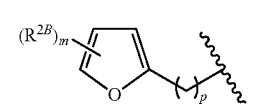
e

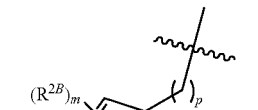
f

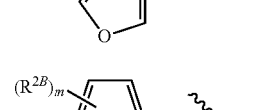
g

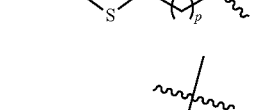
h

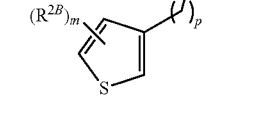
i

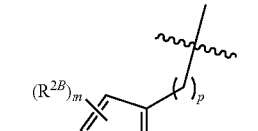
j

-continued

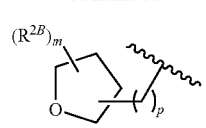
k

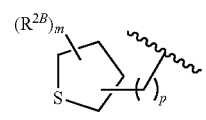
l

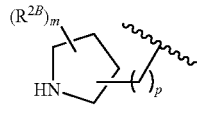
m

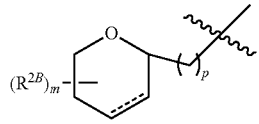
n

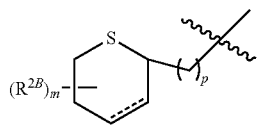
o

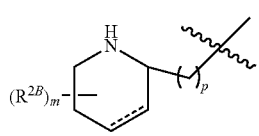
p

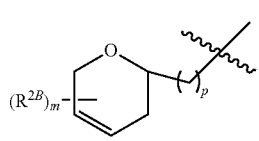
q

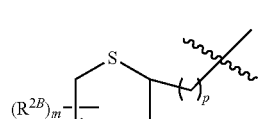
r

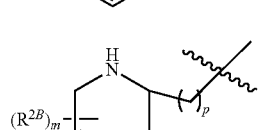
s

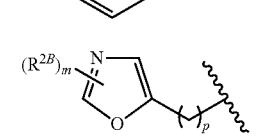
t

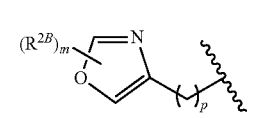
u

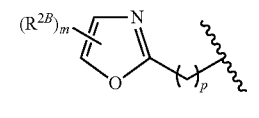
v

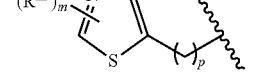
w

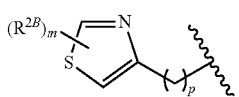 x

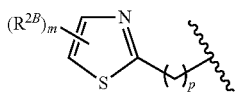 y

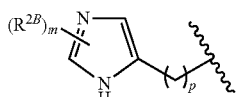 z

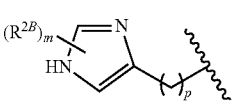 aa

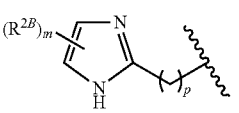 bb

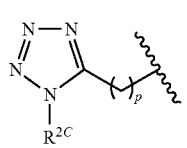 cc

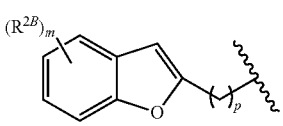 dd

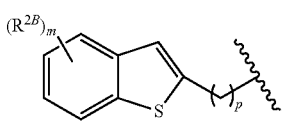 ee

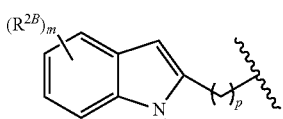 ff
R = H, Alkyl

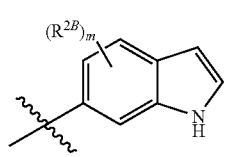 gg

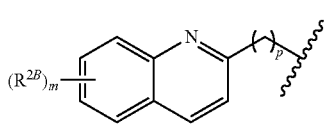 hh

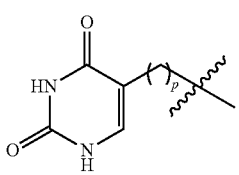 ii

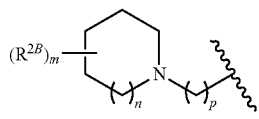 jj
n = 0 or 1

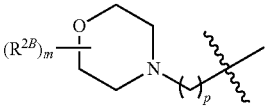 kk

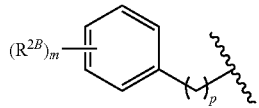 ll

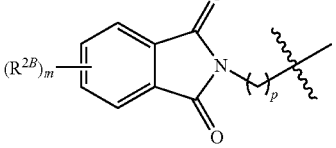 mm

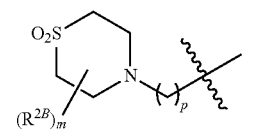 nn

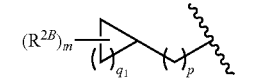 oo wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(═O), —S(═O), —SO₂, —C(═O)O—, —OC(═O), —C(═O)$NR^{W2}$, —$NR^{W2}$C(═O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

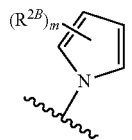 pp

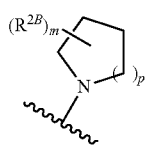 qq

39

-continued

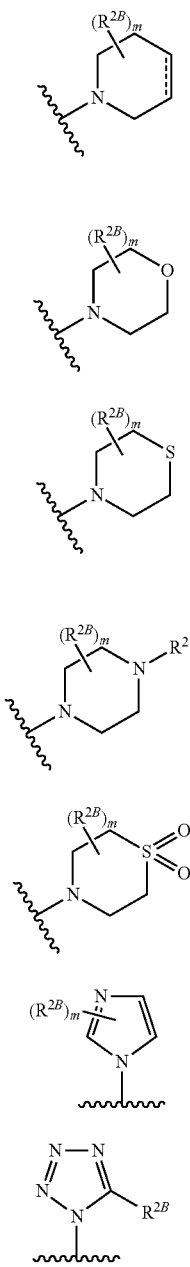

40

In certain embodiments, —X(R$_B$)$_n$ has one of the structures:

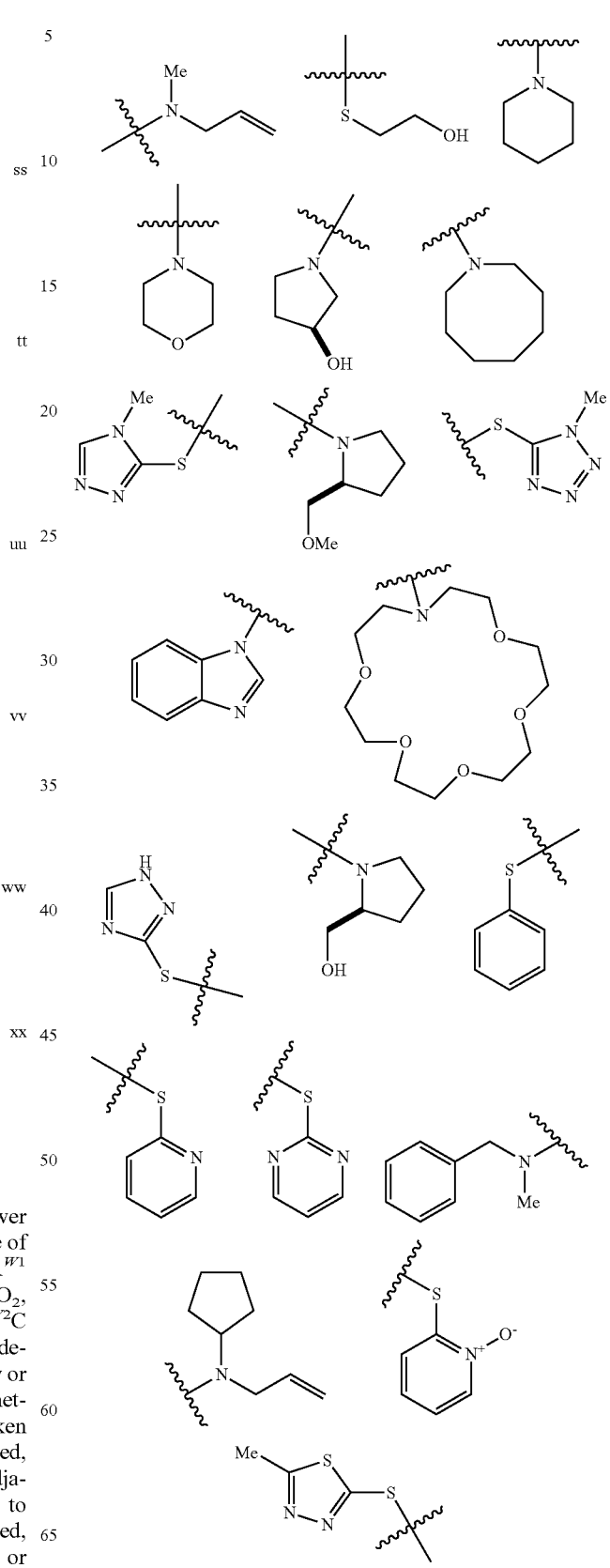

wherein m is an integer from 1 to 4; R is hydrogen, lower alkyl or a nitrogen protecting group; and each occurrence of R$^{2B}$ is independently hydrogen, halogen, —CN, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety.

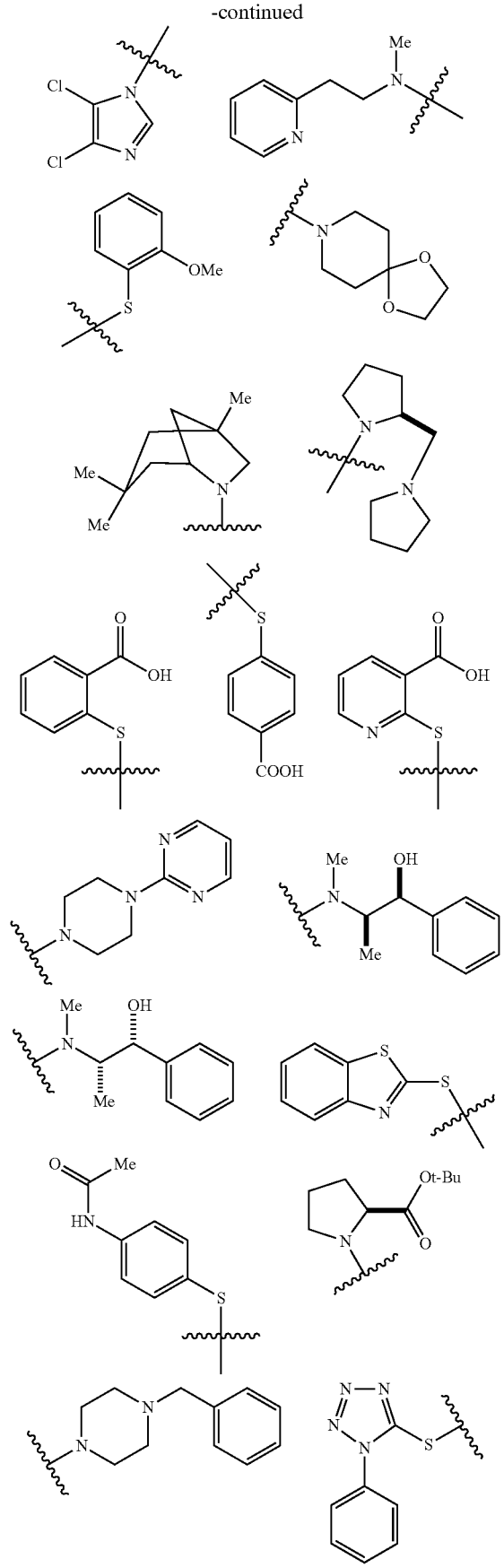
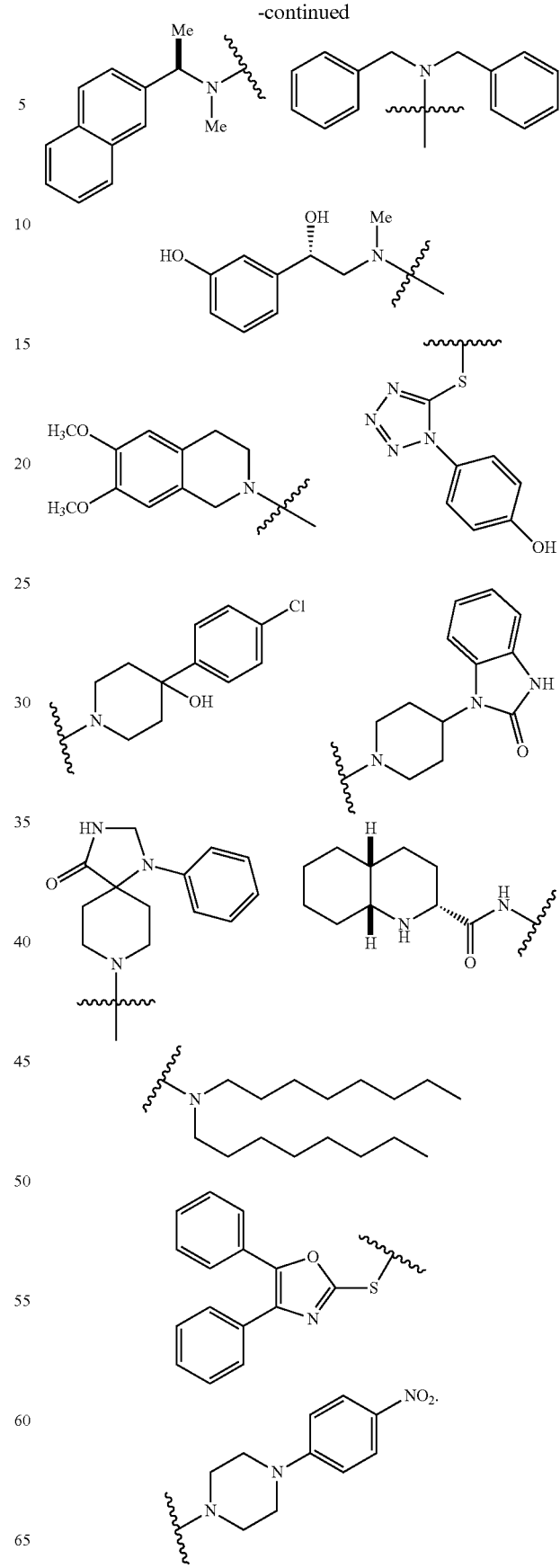

In certain embodiments, R₂ is

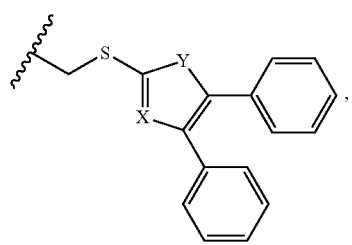

wherein X is N and Y is NH, S, or O. In other embodiments, R₂ is

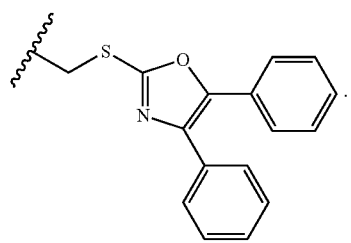

In certain embodiments, R₃ is substituted or unsubstituted aryl. In certain embodiments, R₃ is substituted or unsubstituted phenyl. In certain particular embodiments, R₃ is monosubstituted phenyl. In certain embodiments, R₃ is para-substituted phenyl. In certain embodiments, R₃ is

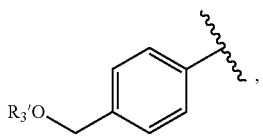

wherein R₃' is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, R₃ is

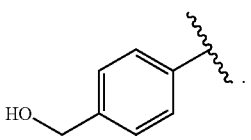

In other embodiments, R₃ is substituted or unsubstituted heteroaryl.

In certain embodiments, the stereochemistry of formula (Ih) is defined as follows:

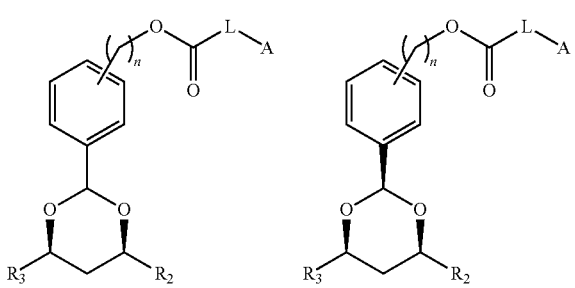

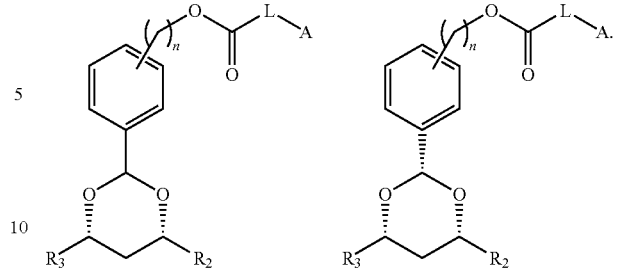

In certain embodiments of the invention, compounds of formula (I) have structure as shown in formula (Ii):

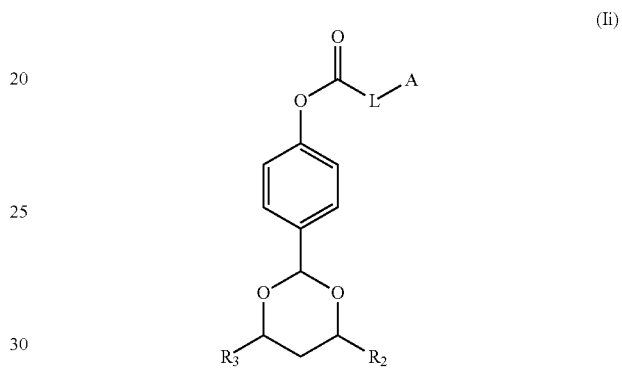

(Ii)

wherein
A and L are defined as above;
R₂ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO₂R$_B$; —CN; —SCN; —SR$_B$; —SOR$_B$; —SO₂R$_B$; —NO₂; —N(R$_B$)₂; —NHC(O)R$_B$; or —C(R$_B$)₃; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and
R₃ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO₂R$_C$; —CN; —SCN; —SR$_C$; —SOR$_C$; —SO₂R$_C$; —NO₂; —N(R$_C$)₂; —NHC(O)R$_C$; or —C(R$_C$)₃; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, R₂ is hydrogen. In other embodiments, R₂ is hydroxyl or a protected hydroxyl group. In certain embodiments, R₂ is alkoxy. In yet other embodiments, R₂ is a lower alkyl, alkenyl, or alkynyl group. In certain embodiments, R₂ is —CH₂—X(R$_B$)$_n$, wherein X is O, S, N, or C, preferably O, S, or N; and n is 1, 2, or 3. In certain embodiments, R₂ is —CH₂—OR_B. In other embodiments, R₂ is —CH₂—SR_B. In yet other embodiments, R₂ is —CH₂—R_B. In other embodiments, R₂ is —CH₂—N(R_B)₂. In still other embodiments, R₂ is —CH₂—NHR_B. In certain embodiments of the invention, R_B is one of:
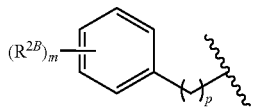
a
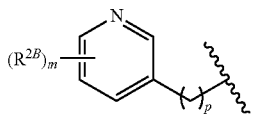
b
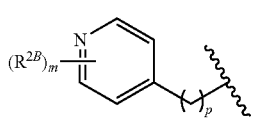
c
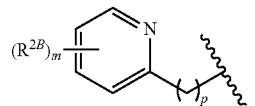
d
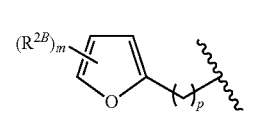
e
f
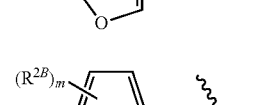
g
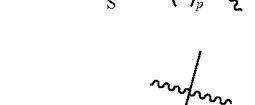
h
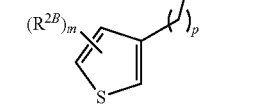
i
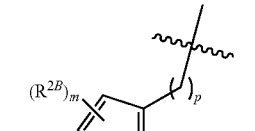
j
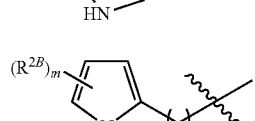
-continued
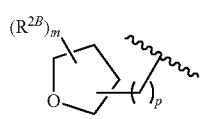
k
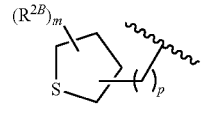
l
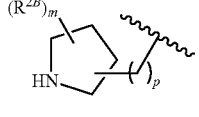
m
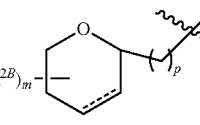
n
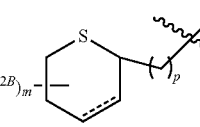
o
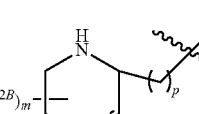
p
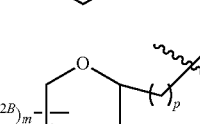
q
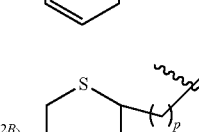
r
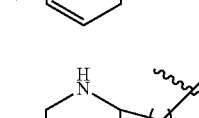
s
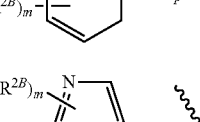
t
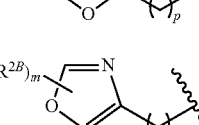
u
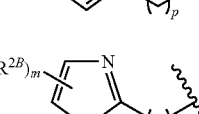
v
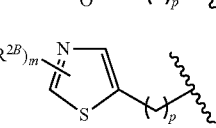
w

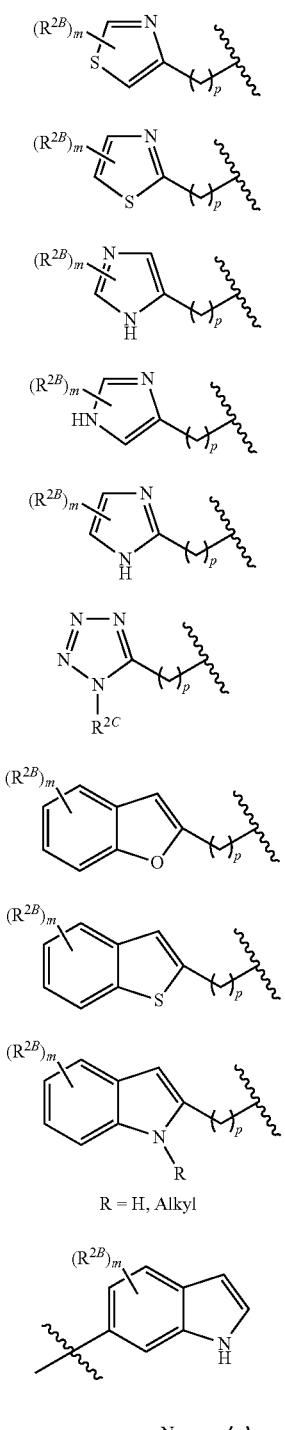
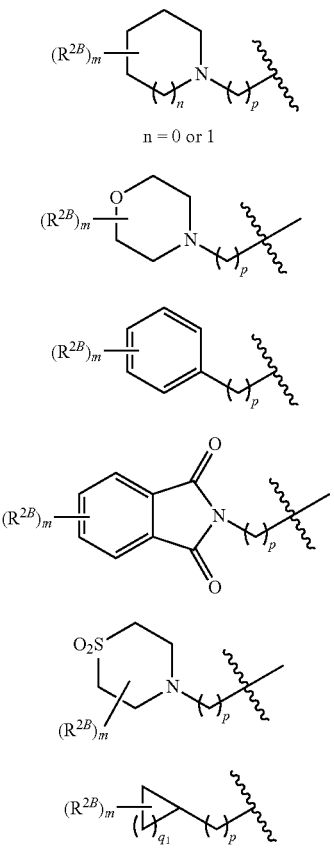

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

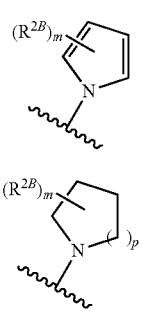

-continued

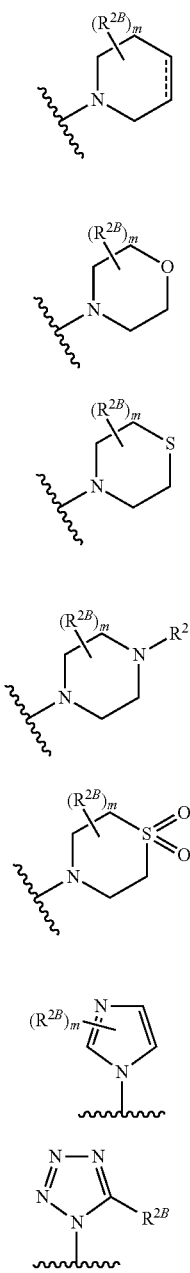

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —X(R$_B$)$_n$ has one of the structures:

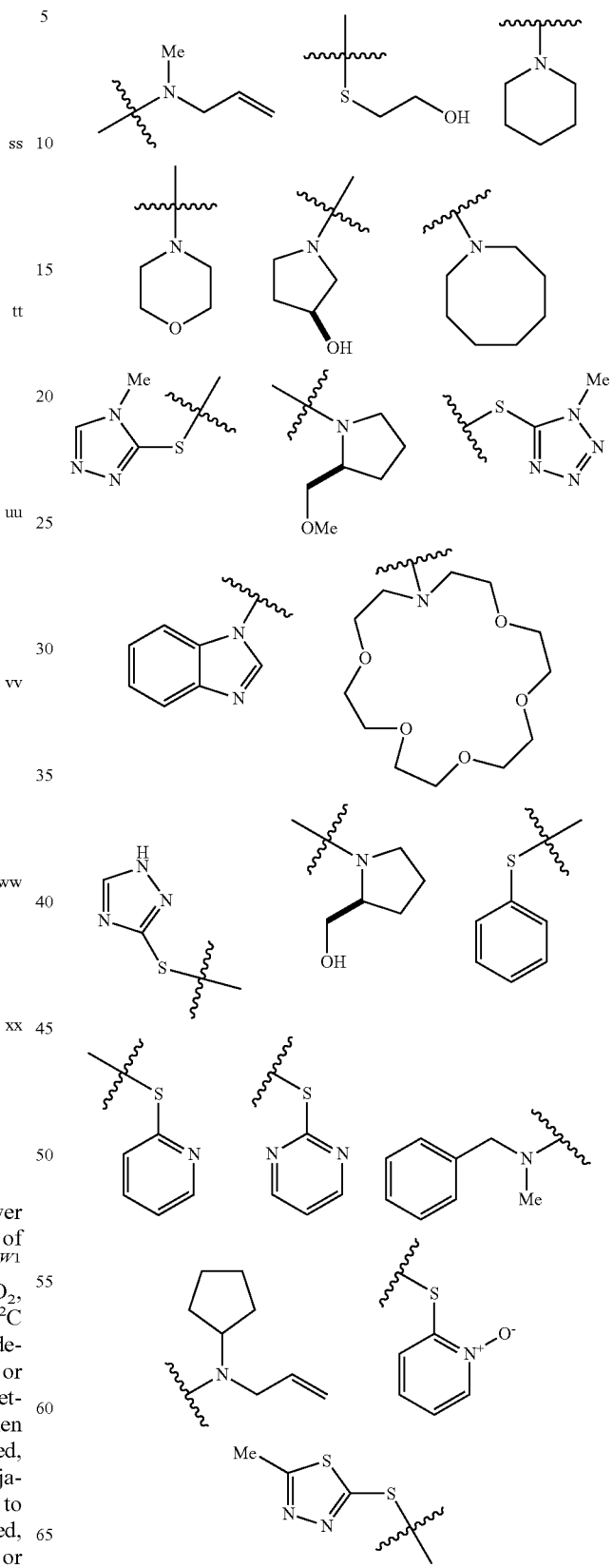

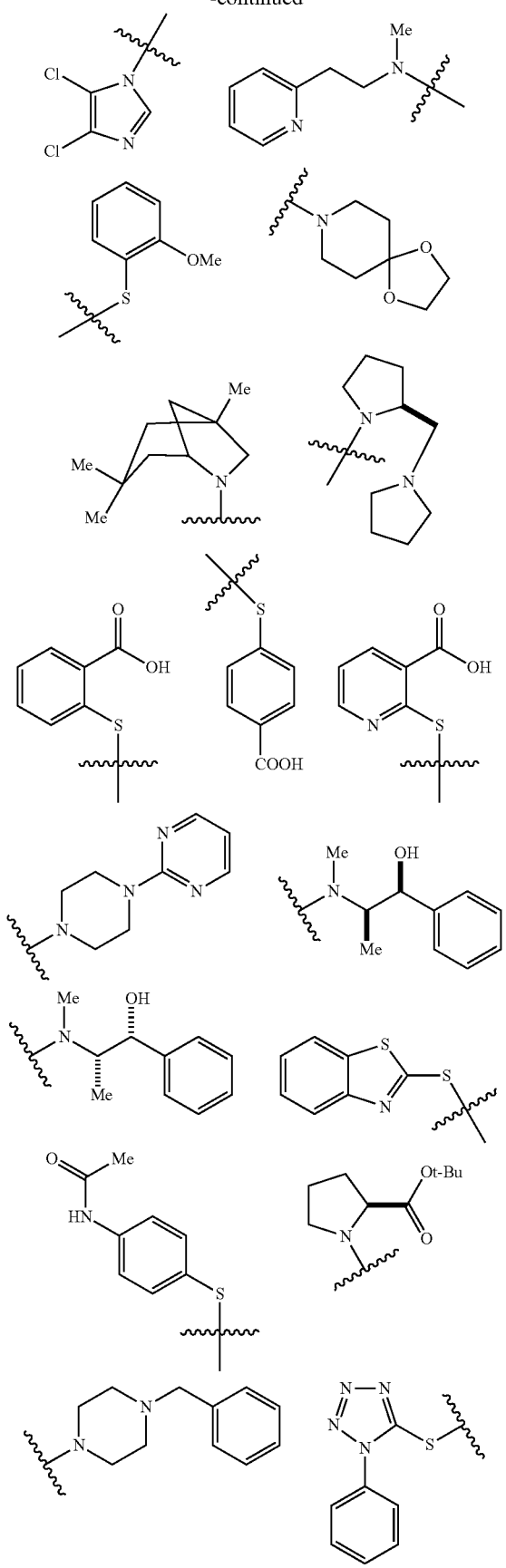
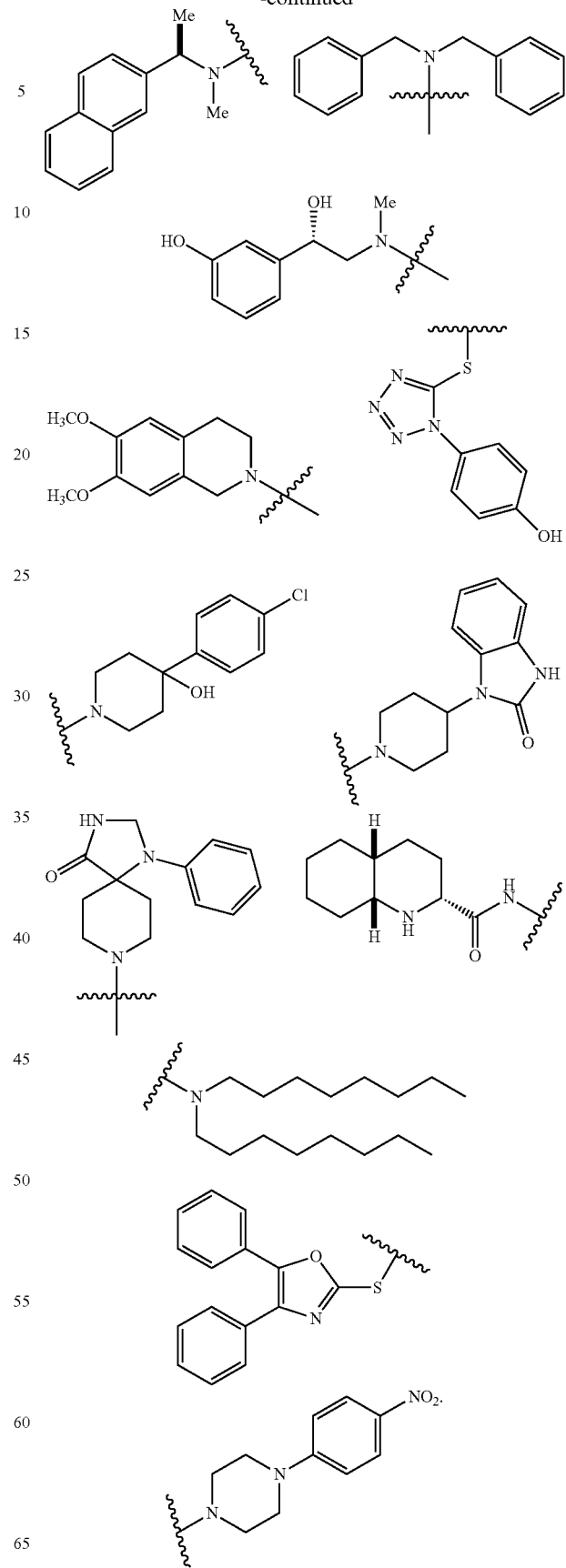

In certain embodiments, R$_2$ is

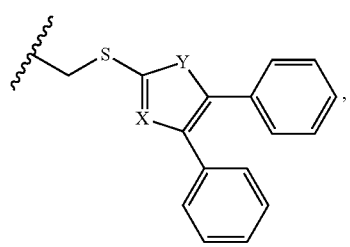

wherein X is N and Y is NH, S, or O. In other embodiments, R$_2$ is

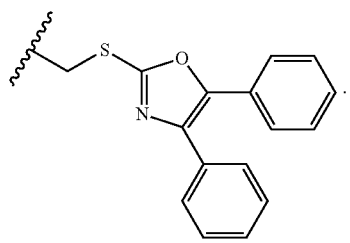 [SMILES: *CSc1nc(-c2ccccc2)c(-c2ccccc2)o1]

In certain embodiments, R$_3$ is substituted or unsubstituted aryl. In certain embodiments, R$_3$ is substituted or unsubstituted phenyl. In certain particular embodiments, R$_3$ is monosubstituted phenyl. In certain embodiments, R$_3$ is para-substituted phenyl. In certain embodiments, R$_3$ is

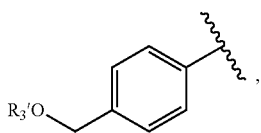

wherein R$_{3'}$ is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, R$_3$ is

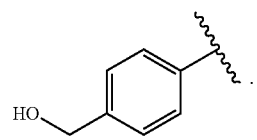

In other embodiments, R$_3$ is substituted or unsubstituted heteroaryl.

In certain embodiments, the stereochemistry of formula (Ii) is defined as follows:

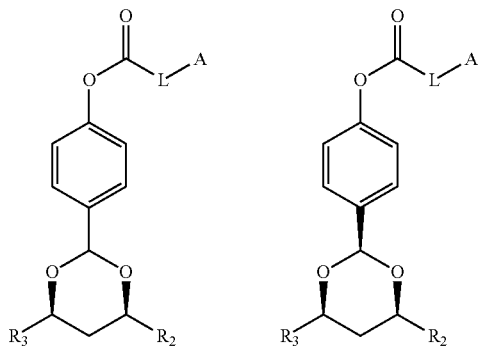

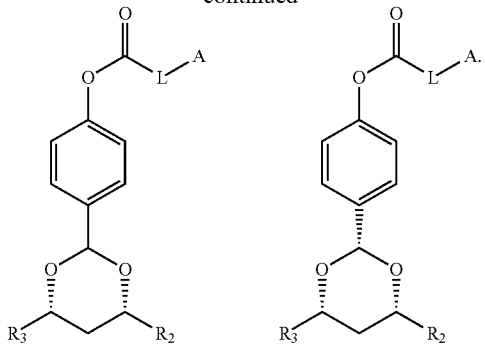

In certain embodiments of the invention, compounds of formula (I) have the following stereochemistry and structure as shown in formula (Ij):

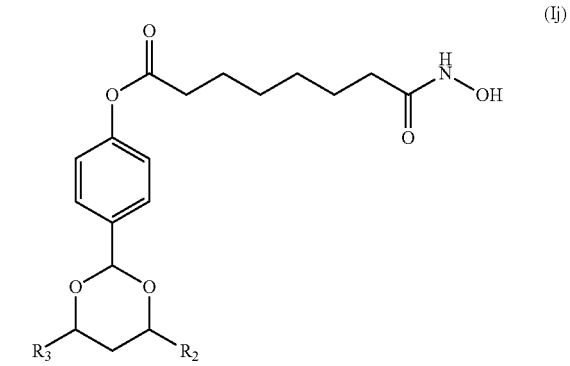

wherein

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, R$_2$ is hydrogen. In other embodiments, R$_2$ is hydroxyl or a protected hydroxyl group. In certain embodiments, R$_2$ is alkoxy. In yet other embodiments, R$_2$ is a lower alkyl, alkenyl, or alkynyl group. In certain embodiments, R$_2$ is —CH$_2$—X(R$_B$)$_n$; wherein X is O, S, N, or C, preferably O, S, or N; and n is 1, 2, or 3. In certain embodiments, R$_2$ is —CH$_2$—OR$_B$. In other embodiments, R$_2$ is —CH$_2$—SR$_B$. In yet other embodiments, R$_2$ is —CH$_2$—R$_B$. In other embodiments, R$_2$ is —CH$_2$—N(R$_B$)$_2$. In still other embodiments, R$_2$ is —CH$_2$—NHR$_B$. In certain embodiments of the invention, R$_B$ is one of:

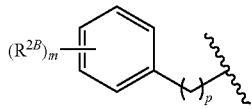
a

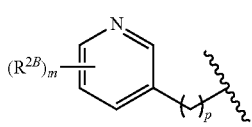
b

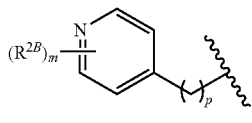
c

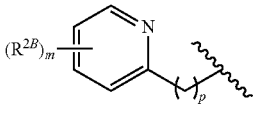
d

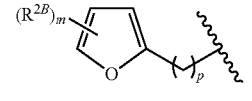
e

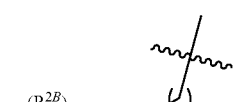
f

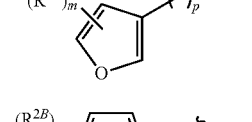
g

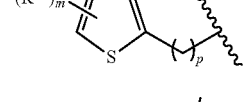
h

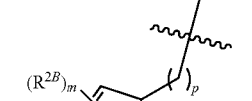
i

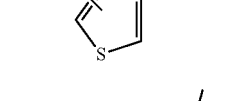
j

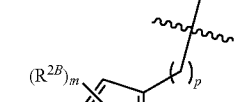

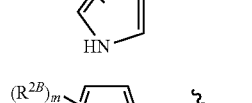

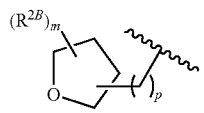
k

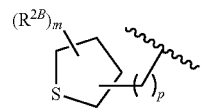
l

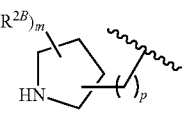
m

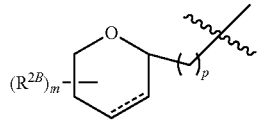
n

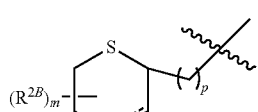
o

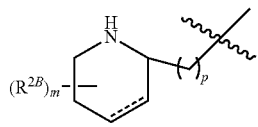
p

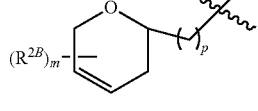
q

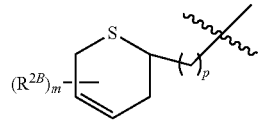
r

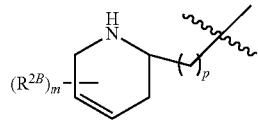
s

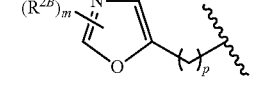
t

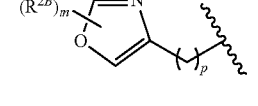
u

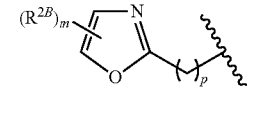
v

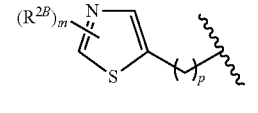
w

-continued x 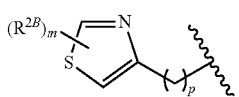

y 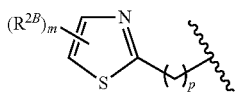

z 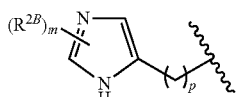

aa 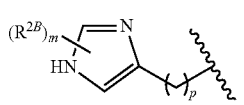

bb 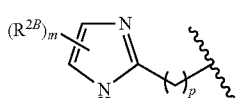

cc 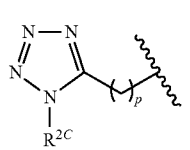

dd 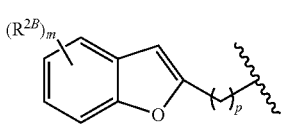

ee 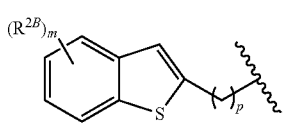

ff 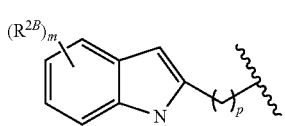

gg 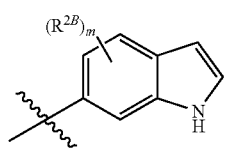
R = H, Alkyl hh 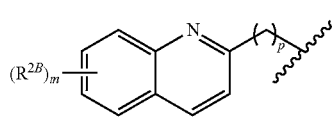

ii 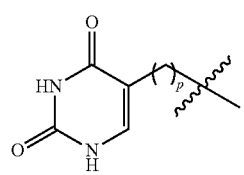

-continued jj 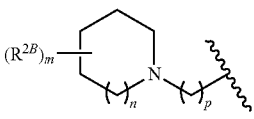
n = 0 or 1 kk 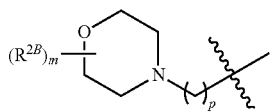

ll 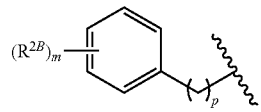

mm 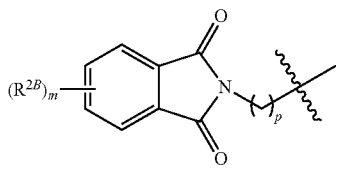

nn 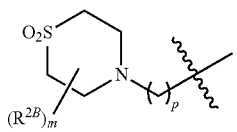

oo 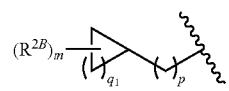

wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety. In certain embodiments of the invention, $R_B$ is one of the structures:

pp 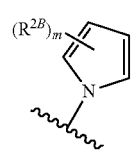

-continued

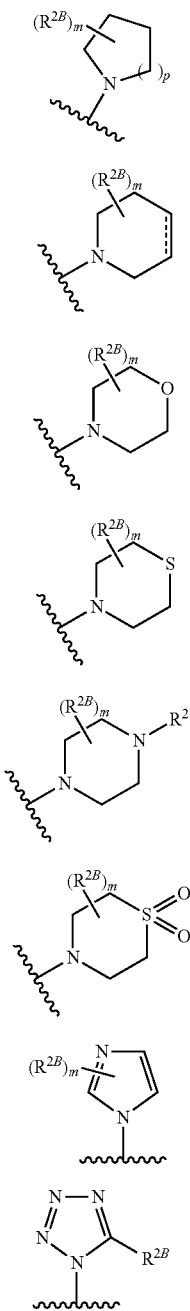

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —$SO_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain embodiments, —$X(R_B)_n$ has one of the structures:

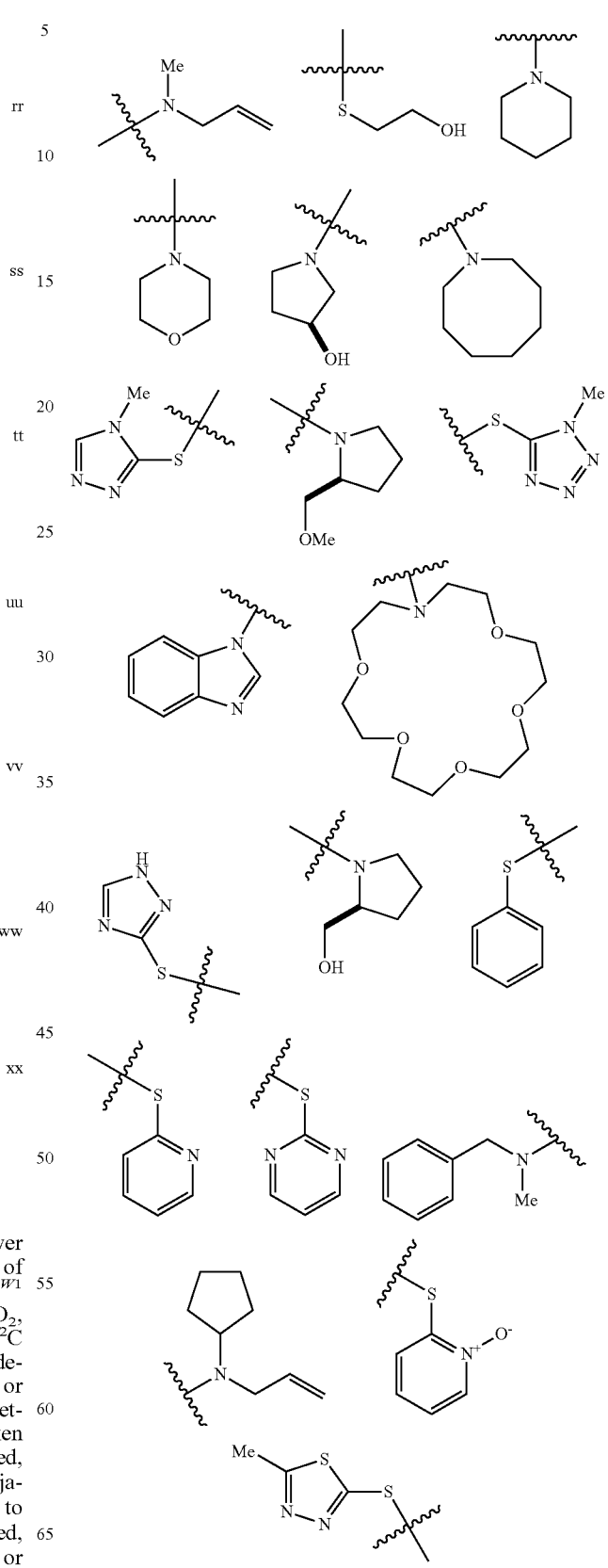

61
-continued
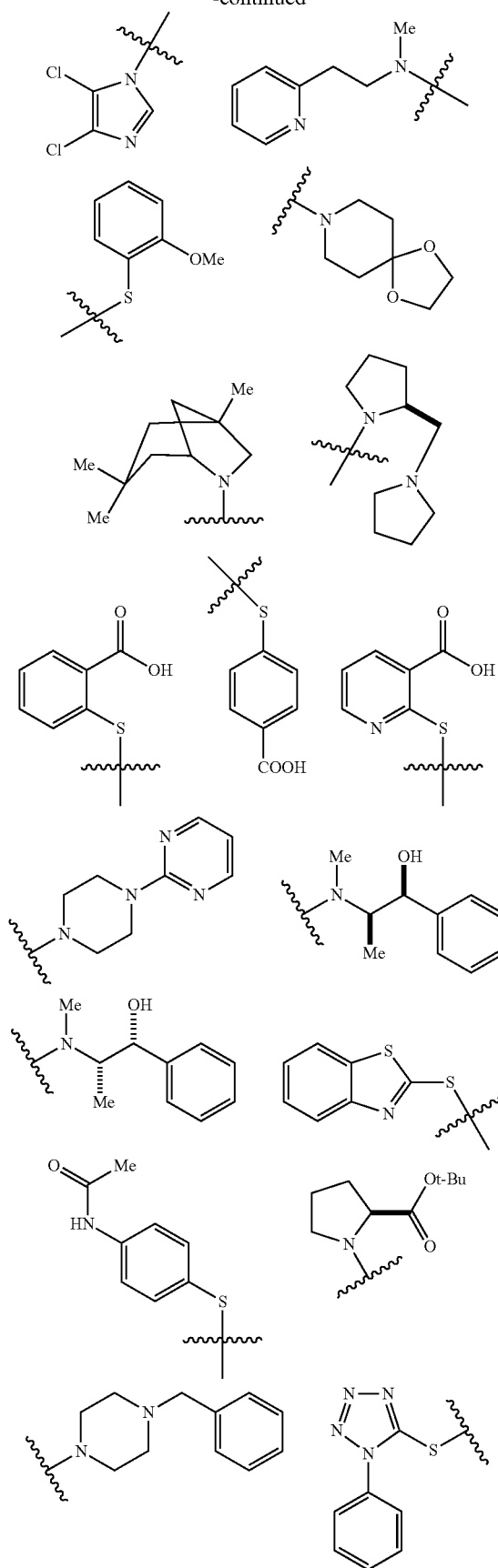
62
-continued
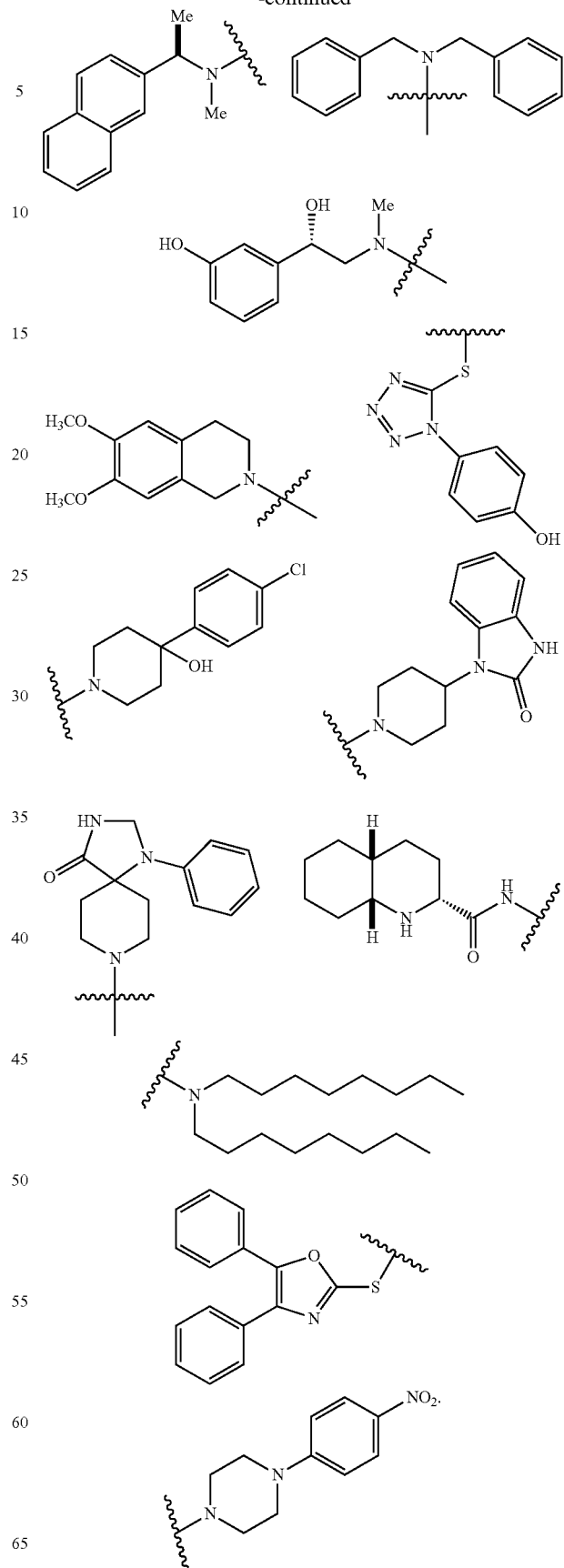

In certain embodiments, $R_2$ is

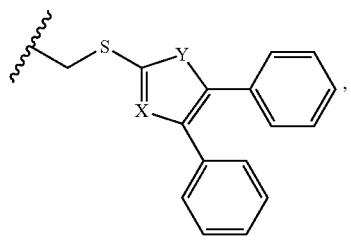

wherein X is N and Y is NH, S, or O. In other embodiments, $R_2$ is

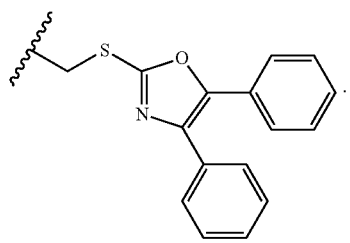 [SMILES: *CSc1nc(-c2ccccc2)c(-c2ccccc2)o1]

In certain embodiments, $R_3$ is substituted or unsubstituted aryl. In certain embodiments, $R_3$ is substituted or unsubstituted phenyl. In certain particular embodiments, $R_3$ is mono-substituted phenyl. In certain embodiments, $R_3$ is para-substituted phenyl. In certain embodiments, $R_3$ is

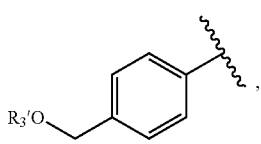

wherein $R_{3'}$ is hydrogen, a protecting group, a solid support unit, an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, $R_3$ is

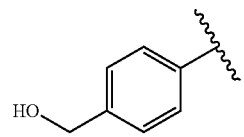

In other embodiments, $R_3$ is substituted or unsubstituted heteroaryl.

Another class of compounds of special interest includes those compounds of the invention as described above and in certain subclasses herein, wherein $R_3$ is a substituted phenyl moiety and the compounds have the formula (II):

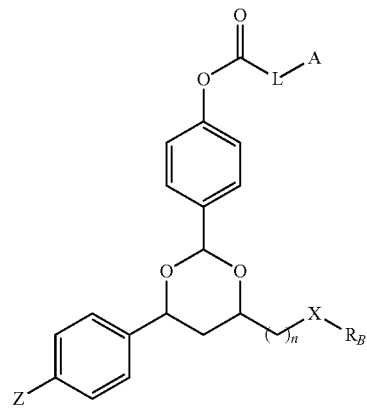

(II)

wherein

L, A, X, and $R_B$ are defined as above;

n is an integer between 0 and 5, inclusive; preferably, between, 1 and 3; more preferably, 2; and Z is hydrogen, —(CH$_2$)$_q$OR$^Z$, —(CH$_2$)$_q$SR$^Z$, —(CH$_2$)$_q$N(R$^Z$)$_2$, —C(=O)R$^Z$, —C(=O)N(R$^Z$)$_2$, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0-4, and wherein each occurrence of $R^Z$ is independently hydrogen, a protecting group, a solid support unit, or an alkyl, acyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety. In certain embodiments, $R^Z$ is hydrogen. In other embodiments, $R^Z$ is C$_1$-C$_6$ alkyl. In certain embodiments, $R^Z$ is an oxygen-protecting group.

Another class of compounds includes those compounds of formula (II), wherein Z is —CH$_2$OR$^Z$, and the compounds have the general structure (Im):

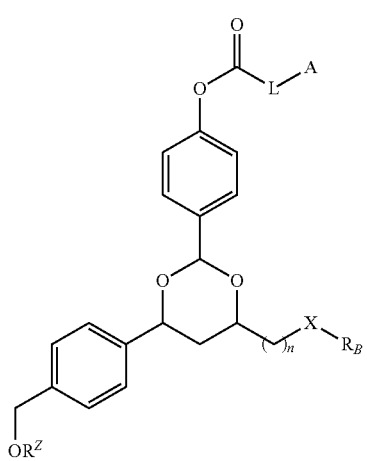

(Im)

wherein $R_B$, $R^Z$, X, L, n, and A are defined generally above and in classes and subclasses herein. In certain embodiments, X is S. In other embodiments, X is O.

Yet another class of compounds of particular interest includes those compounds of formula (Ii), wherein X is S and the compounds have the general structure (In):

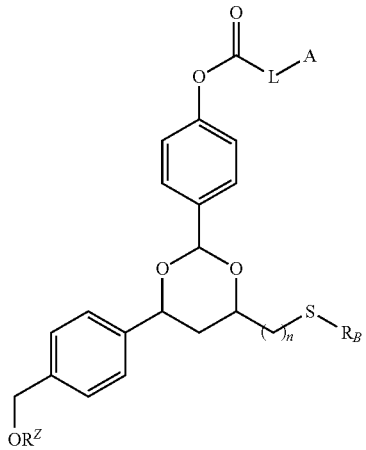

(In)

wherein

R$_B$, X, L, n, and A are defined as above; and

R$^Z$ is as defined generally above and in classes and subclasses herein.

Yet another class of compounds of special interest includes those compounds of formula (Ii), wherein X is —NR$^{2A}$ and the compounds have the general structure (Io):

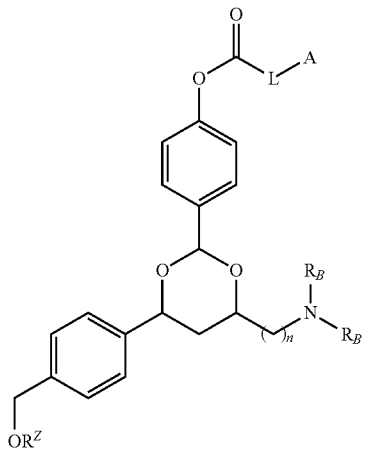

(Io)

wherein

R$_B$, R$^Z$, X, L, n, and A are defined generally above and in classes and subclasses herein.

Yet another class of compounds of special interest includes those compounds of formula (Ii), wherein X is O and the compounds have the general structure (Ip):

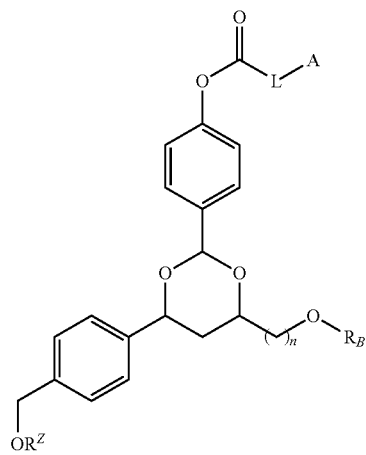

(Ip)

wherein

R$_B$, R$^Z$, X, L, n, and A are defined generally above and in classes and subclasses herein.

Exemplary compounds of the invention are shown:

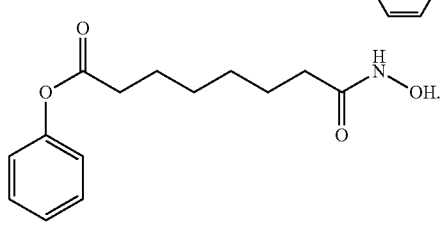

SAHP

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of the compound under different conditions and may exist as one or a combination of polymorphs of the compound forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

Synthetic Overview

The synthesis of the various monomeric compounds used to prepare the dimeric, multimeric, and polymeric compounds of the invention are known in the art. These published syntheses may be utilized to prepare the compounds of the invention. Exemplary synthetic methods for preparing compounds of the invention are described in U.S. Pat. No. 6,960,685; U.S. Pat. No. 6,897,220; U.S. Pat. No. 6,541,661; U.S. Pat. No. 6,512,123; U.S. Pat. No. 6,495,719; US 2006/0020131; US 2004/087631; US 2004/127522; US 2004/0072849; US 2003/0187027; WO 2005/018578; WO 2005/007091; WO 2005/007091; WO 2005/018578; WO 2004/046104; WO 2002/89782; each of which is incorporated herein by reference. In many cases, an amide moiety is changed to an ester moiety to prepare the inventive compounds.

Figure 13:
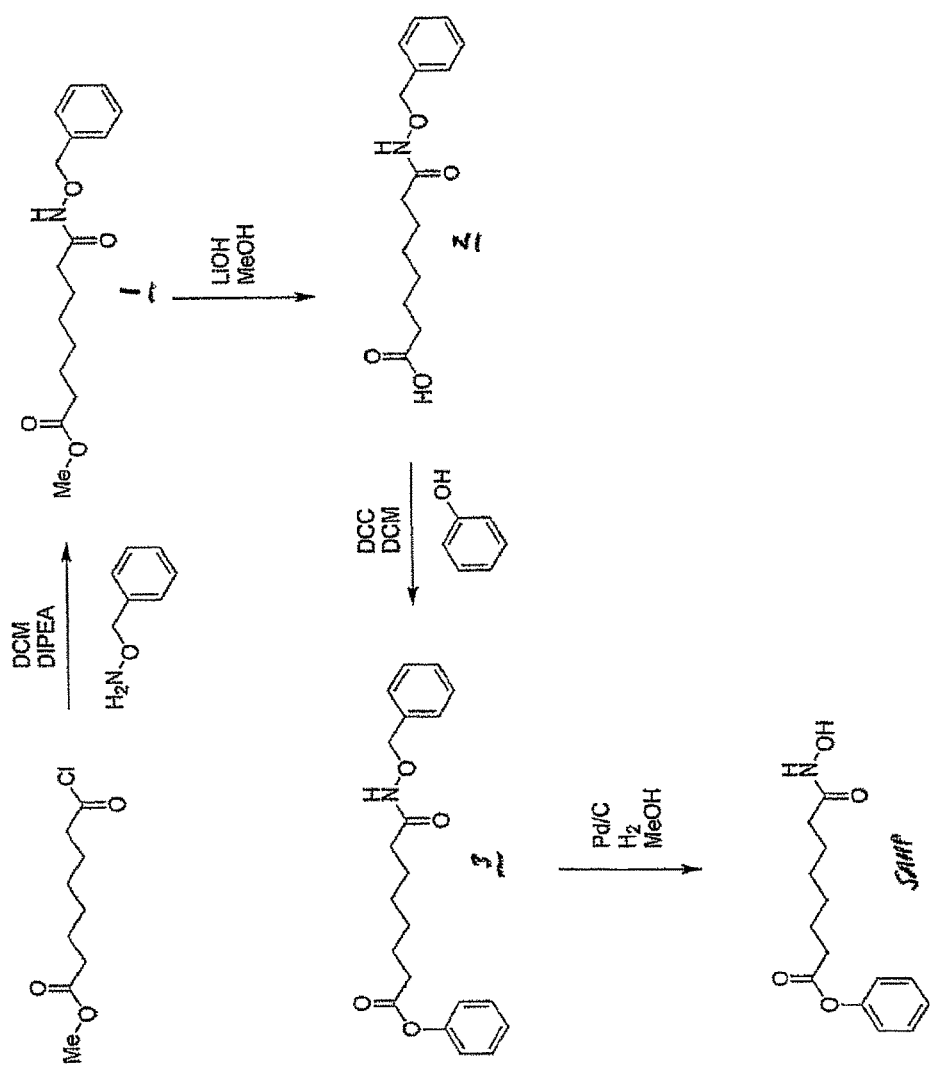

An exemplary synthetic scheme for preparing SAHP is shown in FIG. 13. Those of skill in the art will realize that based on this teaching and those in the art as referenced above one could prepare any of the esterase-sensitive compounds of the invention.

In yet another aspect of the invention, methods for producing intermediates useful for the preparation of certain compounds of the invention are provided.

In one aspect of the invention, a method for the synthesis of the core structure of certain compounds is provided, one method comprising steps of:

providing an epoxy alcohol having the structure:

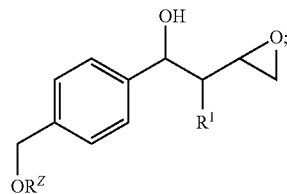

reacting the epoxy alcohol with a reagent having the structure $R^2XH$ under suitable conditions to generate a diol having the core structure:

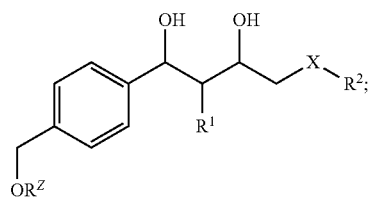

reacting the diol with a reagent having the structure $R^3CH(OMe)_2$ under suitable conditions to generate a scaffold having the core structure:

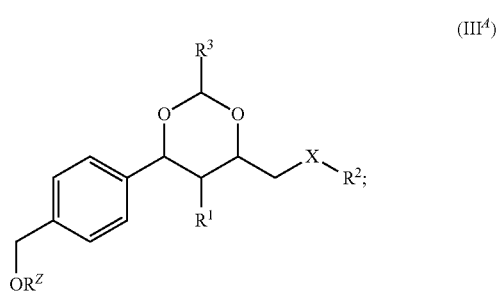

wherein $R^1$ is hydrogen, or an aliphatic, alicyclic, heteroaliphatic, heterocyclic, aromatic or heteroaromatic moiety;

$R^2$ is hydrogen, a protecting group, or an aliphatic, alicyclic, heteroaliphatic, heterocyclic, aromatic or heteroaromatic moiety;

X is —O—, —C($R^{2A}$)$_2$—, —S—, or —N$R^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of $R^2$ and $R^{2A}$, taken together, form an alicyclic or heterocyclic moiety, or an aryl or heteroaryl moiety;

$R^3$ is an aliphatic, alicyclic, heteroaliphatic, heterocyclic, aromatic or heteroaromatic moiety; and $R^Z$ is an aliphatic, alicyclic, heteroaliphatic, heterocyclic, aromatic or heteroaromatic moiety and is optionally attached to a solid support.

In certain exemplary embodiments, the epoxy alcohol has the structure:

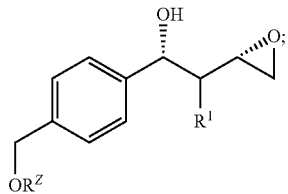

the diol has the structure:

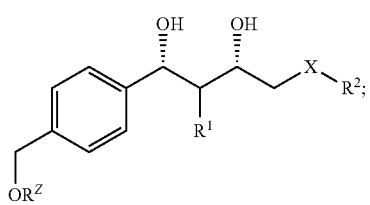

and the core scaffold has the structure:

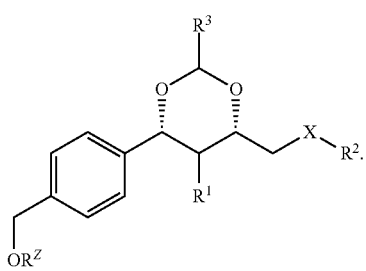

In certain other exemplary embodiments, the epoxy alcohol has the structure:

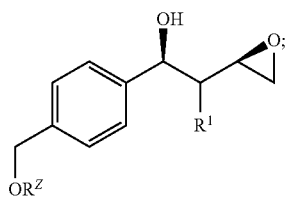

the diol has the structure:

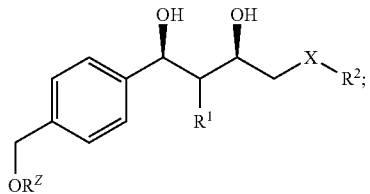

and the the core scaffold has the structure:

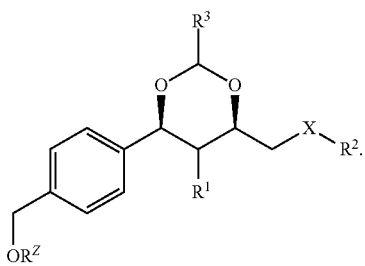

In certain embodiments, $R^3$ has the following structure:

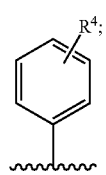

and the method described above generates the structure:

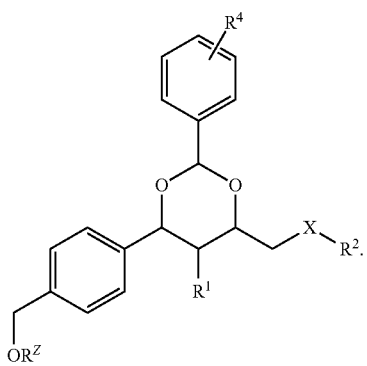

In another aspect of the invention, a method for the synthesis of the core structure of certain compounds of the invention is provided, one method comprising steps of:

providing an epoxy alcohol having the structure:

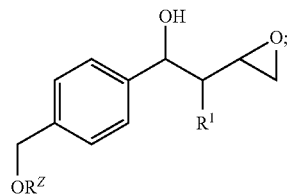

reacting the epoxy alcohol with a reagent having the structure $R^2XH$ under suitable conditions to generate a diol having the core structure:

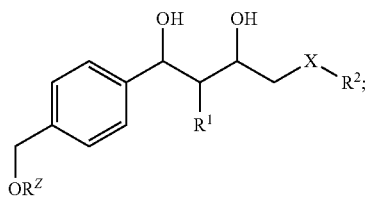

subjecting the diol to a reagent having the structure:

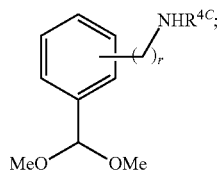

wherein $R^{4C}$ is a nitrogen protecting group; to suitable conditions to generate an amine having the structure:

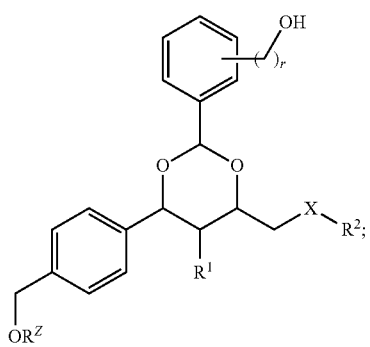

reacting the amine with a reagent having the structure:

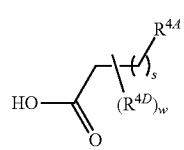

under suitable conditions to generate a scaffold having the core structure:

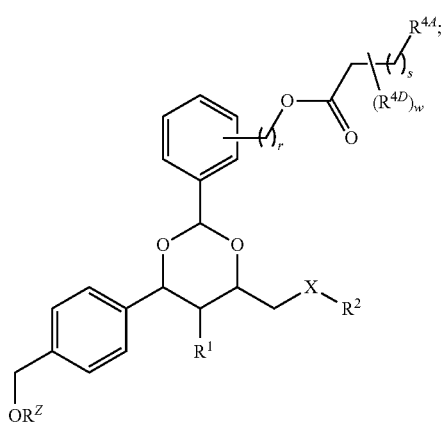

wherein $R^1$ is hydrogen, or an aliphatic, alicyclic, heteroaliphatic, heterocyclic, aromatic or heteroaromatic moiety;

$R^2$ is hydrogen, a protecting group, or an aliphatic, alicyclic, heteroaliphatic, heterocyclic, aromatic or heteroaromatic moiety;

X is —O—, —C($R^{2A}$)$_2$—, —S—, or —N$R^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of $R^2$ and $R^{2A}$, taken together, form an alicyclic or heterocyclic moiety, or an aryl or heteroaryl moiety;

r is 0 or 1;

s is an integer from 2-5;

w is an integer from 0-4;

$R^{4A}$ comprises a metal chelator;

each occurrence of $R^{4D}$ is independently hydrogen, alkyl, heteroalkyl, cycloalkyl, heterocyclic, alkenyl, alkynyl, aryl, heteroaryl, halogen, CN, NO$_2$, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety; and $R^Z$ is an aliphatic, alicyclic, heteroaliphatic, heterocyclic, aromatic or heteroaromatic moiety and is optionally attached to a solid support.

In certain exemplary embodiments, the epoxy alcohol has the structure:

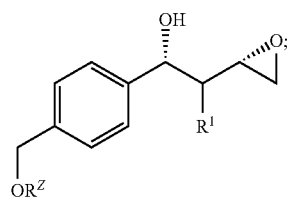

the diol has the structure:

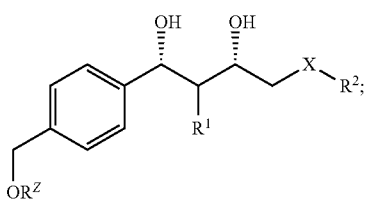

the amine has the structure:

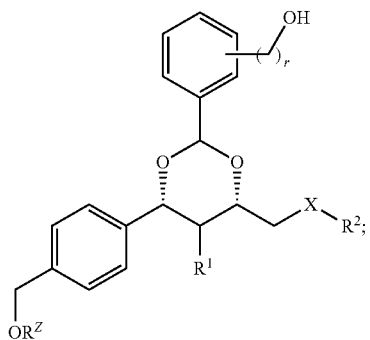

and the core scaffold has the structure:

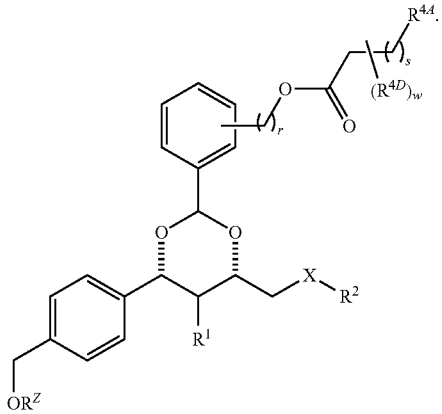

In certain exemplary embodiments, the epoxy alcohol has the structure:

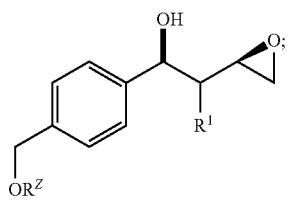

the diol has the structure:

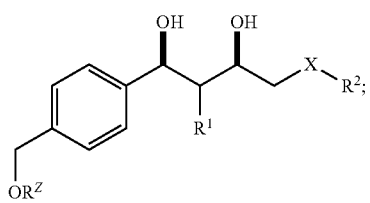

the amine has the structure:

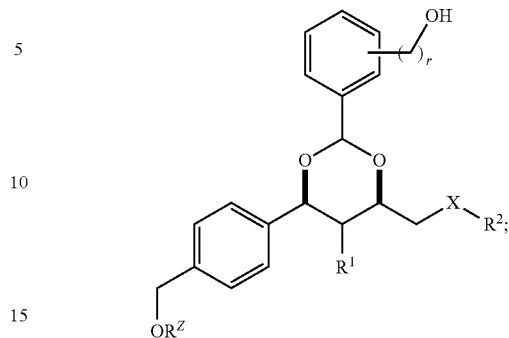

and the core scaffold has the structure:

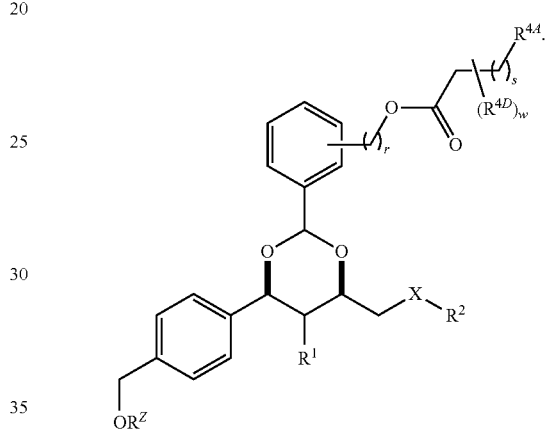

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

Pharmaceutical Compositions

As discussed above, the present invention provides novel compounds having antitumor and antiproliferative activity, and thus the inventive compounds are useful for the treatment of cancer (e.g., cutaneous T-cell lymphoma). Benign proliferative diseases may also be treated using the inventive compounds. The compounds are also useful in the treatment of other diseases or condition that benefit from inhibition of deacetylation activity (e.g. HDAC inhibition). In certain embodiments, the compounds are useful in the treatment of baldness based on the discovery that HDAC inhibition (particularly, HDAC6 inhibition) blocks androgen signaling vis hsp90. HDAC inhibition has also been shown to inhibit estrogen signaling. In certain embodiments, the compounds are useful in blocking the hyperpigmentation of skin by HDAC inhibition.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved chemotherapeutic agent, or it may be any one of a number of agents undergoing approval in the Food and Drug Administration that ultimately obtain approval for the treatment of hair loss, skin hyperpigmentation, protozoal infections, and/or any disorder associated with cellular hyperproliferation. In certain other embodiments, the additional therapeutic agent is an anticancer agent, as discussed in more detail herein. In certain other embodiments, the compositions of the invention are useful for the treatment of protozoal infections.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci nih gov) and the Food and Drug Administration (FDA) website for a list of the FDA approved oncology drugs (www.fda.gov/cder/cancer/drug-listframe).

In certain embodiments, the pharmaceutical compositions of the present invention further comprise one or more additional therapeutically active ingredients (e.g., chemotherapeutic and/or palliative). For purposes of the invention, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present invention provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Research Uses, Pharmaceutical Uses and Methods of Treatment

Research Uses

According to the present invention, the inventive compounds may be assayed in any of the available assays known in the art for identifying compounds having antiprotozoal, HDAC inhibitory, hair growth, androgen signalling inhibitory, estrogen signaling inhibitory, and/or antiproliferative activity. For example, the assay may be cellular or non-cellular, in vivo or in vitro, high- or low-throughput format, etc.

Thus, in one aspect, compounds of this invention which are of particular interest include those which:
exhibit HDAC-inhibitory activity;
exhibit HDAC Class I inhibitory activity (e.g., HDAC1, HDAC2, HDAC3, HDAC8);
exhibit HDAC Class II inhibitory activity (e.g., HDAC4, HDAC5, HDAC6, HDAC7, HDAC9a, HDAC9b, HDRP/HDAC9c, HDAC10);
exhibit the ability to inhibit HDAC1 (Genbank Accession No. NP_004955, incorporated herein by reference);
exhibit the ability to inhibit HDAC2 (Genbank Accession No. NP_001518, incorporated herein by reference);
exhibit the ability to inhibit HDAC3 (Genbank Accession No. O15739, incorporated herein by reference);
exhibit the ability to inhibit HDAC4 (Genbank Accession No. AAD29046, incorporated herein by reference);
exhibit the ability to inhibit HDAC5 (Genbank Accession No. NP_005465, incorporated herein by reference);
exhibit the ability to inhibit HDAC6 (Genbank Accession No. NP_006035, incorporated herein by reference);
exhibit the ability to inhibit HDAC7 (Genbank Accession No. AAP63491, incorporated herein by reference);
exhibit the ability to inhibit HDAC8 (Genbank Accession No. AAF73428, NM_018486, AF245664, AF230097, each of which is incorporated herein by reference);
exhibit the ability to inhibit HDAC9 (Genbank Accession No. NM_178425, NM_178423, NM_058176, NM_014707, BC111735, NM_058177, each of which is incorporated herein by reference)
exhibit the ability to inhibit HDAC10 (Genbank Accession No. NM_032019, incorporated herein by reference)
exhibit the ability to inhibit HDAC11 (Genbank Accession No. BC009676, incorporated herein by reference);
exhibit the ability to inhibit tubulin deacetylation (TDAC);
exhibit the ability to modulate the glucose-sensitive subset of genes downstream of Ure2p;
exhibit cytotoxic or growth inhibitory effect on cancer cell lines maintained in vitro or in animal studies using a scientifically acceptable cancer cell xenograft model; and/or
exhibit a therapeutic profile (e.g., optimum safety and curative effect) that is superior to existing chemotherapeutic agents.

As detailed in the exemplification herein, in assays to determine the ability of compounds to inhibit cancer cell growth certain inventive compounds may exhibit $IC_{50}$ values $\leq 100$ µM. In certain other embodiments, inventive compounds exhibit $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain embodiments, inventive compounds exhibit $IC_{50}$ values $\leq 5$ µM. In certain other embodiments, inventive compounds exhibit $IC_{50}$ values $\leq 2.5$ µM. In certain embodiments, inventive compounds exhibit $IC_{50}$ values $\leq 1$ µM. In certain embodiments, inventive compounds exhibit $IC_{50}$ values $\leq 0.75$ µM. In certain embodiments, inventive compounds exhibit $IC_{50}$ values $\leq 0.5$ µM. In certain embodiments, inventive compounds exhibit $IC_{50}$ values $\leq 0.25$ µM. In certain embodiments, inventive compounds exhibit $IC_{50}$ values $\leq 0.1$ µM. In certain other embodiments, inventive compounds exhibit $IC_{50}$ values $\leq 75$ nM. In certain other embodiments, inventive compounds exhibit $IC_{50}$ values $\leq 50$ nM. In certain other embodiments, inventive compounds exhibit $IC_{50}$ values $\leq 25$ nM. In certain other embodiments, inventive compounds exhibit $IC_{50}$ values $\leq 10$ nM. In other embodiments, exemplary compounds exhibited $IC_{50}$ values $\leq 7.5$ nM. In other embodiments, exemplary compounds exhibited $IC_{50}$ values $\leq 5$ nM.

Pharmaceutical Uses and Methods of Treatment

In general, methods of using the compounds of the present invention comprise administering to a subject in need thereof a therapeutically effective amount of a compound of the present invention. The compounds of the invention are generally inhibitors of deacetyalse activity. As discussed above, the compounds of the invention are typically inhibitors of histone deacetylases and, as such, are useful in the treatment of disorders modulated by histone deacetylases. Other deacetylase such as tubulin deacetylases may also be inhibited by the inventive compounds.

In certain embodiments, compounds of the invention are useful in the treatment of proliferative diseases (e.g., cancer, benign neoplasms, inflammatory disease, autoimmune diseases). In certain embodiments, given the esterase sensitive ester linkage in the compounds of the invention, they are particularly useful in treating skin disorders modulated by histone deacetyalses where systemic effects of the drug are to be avoided or at least minimized. This feature of the inventive compounds may allow the use of compounds normally too toxic for administration to a subject systemically. In certain embodiments, these skin disorders are proliferative disorders. For example, the inventive compounds are particularly useful in the treatment of skin cancer and benign skin tumors. In certain embodiments, the compounds are useful in the treatment of cutaneous T-cell lymphoma. In certain embodiments, the compounds are useful in the treatment of neurofibromatosis. Accordingly, in yet another aspect, according to the methods of treatment of the present invention, tumor cells are killed, or their growth is inhibited by contacting said tumor cells with an inventive compound or composition, as described herein. In other embodiments, the compounds are useful in treating inflammatory diseases of the skin such as psoriasis or dermatitis. In other embodiments, the compounds are useful in the treatment or prevention of hair loss. In certain embodiments, the compounds are useful in the treatment of diseases associated with skin pigmentation. For example, the compounds may be used to prevent the hyperpigmentation of skin.

Thus, in another aspect of the invention, methods for the treatment of cancer are provided comprising administering a therapeutically effective amount of an inventive compound, as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. Preferably, the inventive compounds is administered topically. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. In certain embodiments of the present invention a "therapeutically effective amount" of the inventive compound or pharmaceutical composition is that amount effective for inhibiting deacetylase activity (in particular, HDAC activity) in skin cells. In certain embodiments of the present invention a "therapeutically effective amount" of the inventive compound or pharmaceutical composition is that amount effective to kill or inhibit the growth of skin cells.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors.

In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing restenosis (See, for example, Presbitero P. et al., "Drug eluting stents do they make the difference?", *Minerva Cardioangiol,* 2002, 50(5):431-442; Ruygrok P. N. et al., "Rapamycin in cardiovascular medicine", *Intern. Med. J.,* 2003, 33(3):103-109; and Marx S. O. et al., "Bench to bedside: the development of rapamycin and its application to stent restenosis", *Circulation,* 2001, 104(8):852-855, each of these references is incorporated herein by reference in its entirety). Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral and/or vascular obstruction.

Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in U.S. Patent Application Publication No.: 2003/0004209 in paragraphs [0146]-[0155], which paragraphs are hereby incorporated herein by reference.

Another aspect of the invention relates to a method for inhibiting the growth of multidrug resistant cells in a biological sample or a patient, which method comprises administering to the patient, or contacting said biological sample with a compound of formula I or a composition comprising said compound.

Additionally, the present invention provides pharmaceutically acceptable derivatives of the inventive compounds, and methods of treating a subject using these compounds, pharmaceutical compositions thereof, or either of these in combination with one or more additional therapeutic agents.

Another aspect of the invention relates to a method of treating or lessening the severity of a disease or condition associated with a proliferation disorder in a patient, said method comprising a step of administering to said patient, a compound of formula I or a composition comprising said compound.

It will be appreciated that the compounds and compositions, according to the method of the present invention, may be administered using any amount and any route of administration effective for the treatment of cancer and/or disorders associated with cell hyperproliferation. For example, when using the inventive compounds for the treatment of cancer, the expression "effective amount" as used herein, refers to a sufficient amount of agent to inhibit cell proliferation, or refers to a sufficient amount to reduce the effects of cancer. The exact amount required will vary from subject to subject, depending on the species, age, and general condition of the subject, the severity of the diseases, the particular anticancer agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Another aspect of the invention relates to a method for inhibiting histone deacetylase activity in a biological sample or a patient, which method comprises administering to the patient, or contacting said biological sample with an inventive compound or a composition comprising said compound.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the topical delivery of the inventive compounds. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

Examples

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Description of Synthetic Methods

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of a variety combinatorial techniques, parallel synthesis and/or solid phase synthetic methods such as those discussed in detail below may be used. Alternatively or additionally, the inventive compounds may be prepared using any of a variety of solution phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Synthesis of Exemplary Compounds

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein.

Example 1: Synthesis of SAHP for Use as HDAC Inhibitors

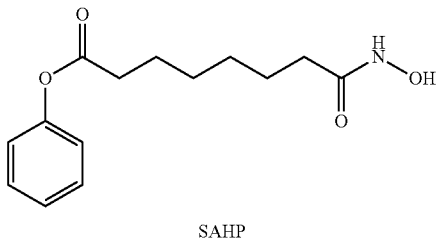 [SMILES: O=C(CCCCCCC(=O)Oc1ccccc1)NO]

SAHP

Figure 12:
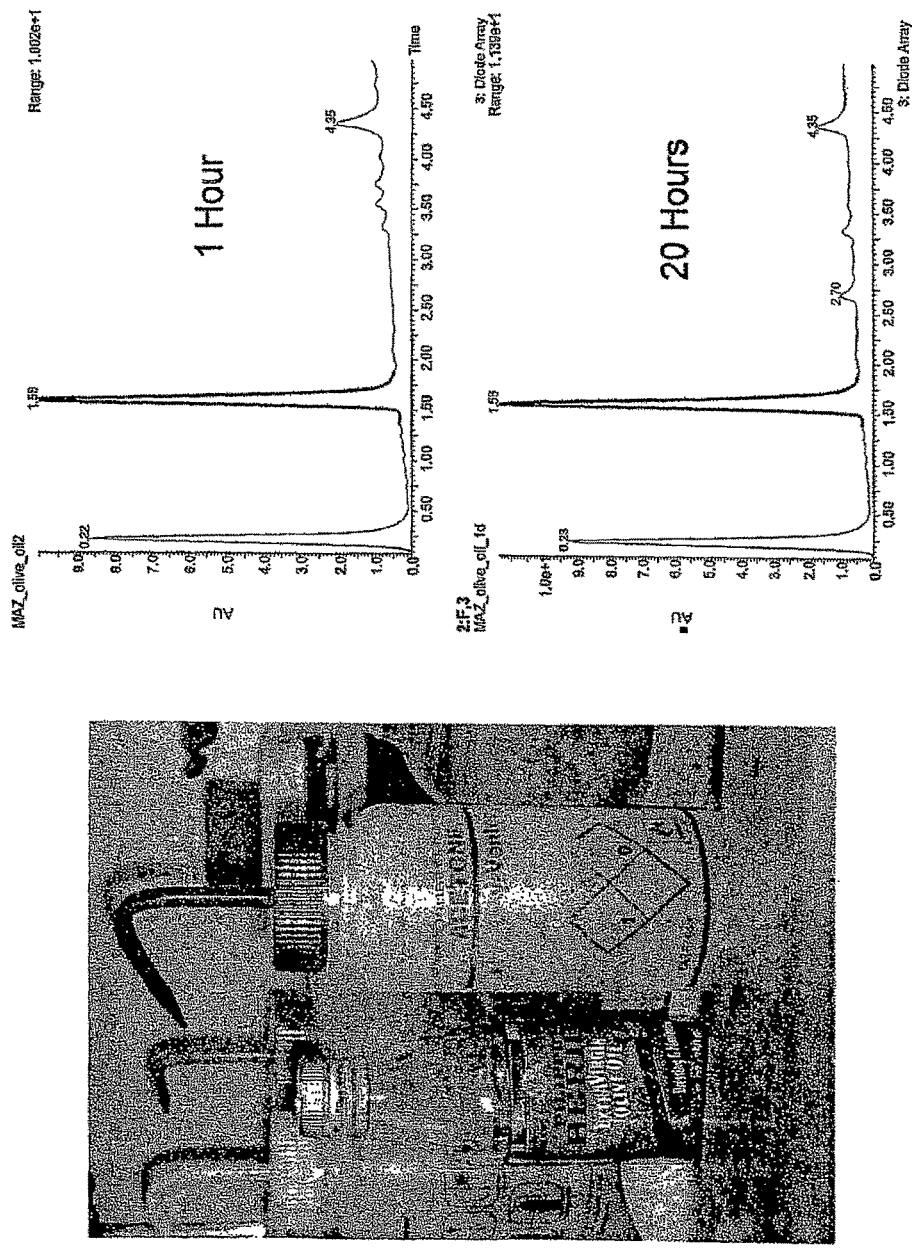

Described below is the synthesis of a SAHP, an ester-containing analog of SAHA (as shown in FIG. 12).

3.86 g (24.2 mmol) O-benzylhydroxylamine hydrochloride and 13 mL (75 mmol) diisopropylethylamine were dissolved in 100 mL methylene chloride and cooled to 0° C. 5.00 g (24.2 mmol) methyl 8-chloro-8-oxooctanoate were dissolved in 10 mL methylene chloride and slowly added to the reaction mixture. The reaction mixture was stirred for 1 h at 0° C. and warmed to room temperature. After stirring for additional 12 h, 300 mL 0.5N HCl were added. The organic layer was separated and washed with brine and sat. bicarb. After drying over sodium sulfate, the organic solvent was removed under reduced pressure and the crude product was purified on silica (methylene chloride/methanol 12:1, rf=0.7) to yield the desired compound 1 as white solid (6.3 g, 89%).

6.3 g (21.5 mmol) methyl ester 1 were dissolved in 200 mL methanol, followed by the addition of 50 mL 2N LiOH.

The reaction mixture was heated to reflux for 1 h and cooled to room temperature. After addition of 100 mL 1N HCl and 200 mL water, the reaction mixture was extracted three times with 150 mL ethyl acetate. The combined organic layers were dried over sodium sulfate and the solvent was removed under reduced pressure to afford the carboxylic acid 2 pure and in quantitative yields as white solid 140 mg carboxylic acid 2 (5 mmol), 56.5 mg phenol (6 mmol) and 113 mg dicyclohexylcarbodiimide (5.5 mmol) are mixed followed by the addition of 10 mL methylene chloride and 30 mg 4-Dimethylaminopyridine. The reaction mixture was stirred for 2 h and applied crude on a silica column followed by elution with haxanes/ethyl acetate (10-100% ethyl acetate). The desired phenol ester 3 was obtained as a white solid in 87% yield (155 mg).

80 mg phenol ester 3 (0.225 mmol) are dissolved in methanol. A catalytical amount of palladium on charcoal (10%) was as added and hydrogen was bubbled through the reaction mixture. After 1 h hour no starting material was detectable by TLC. The reaction mixture was filtered through Celite and the solvent was removed under reduced pressure to yield the free hydroxamte SAHP as brownish solid in quantitative yields (59 mg). The crude product did not show any impurities as judged by LCMS and NMR.

Example 2: Biological Assay Procedures

Cell culture and Transfections.

TAg-Jurkat cells were transfected by electroporation with 5 μg of FLAG-epitope-tagged pBJ5 constructs for expression of recombinant proteins. Cells were harvested 48 h posttransfection.

HDAC assays.

[$^3$H]Acetate-incorporated histones were isolated from butyrate-treated HeLa cells by hydroxyapatite chromatography (as described in Tong, et al. *Nature* 1997, 395, 917-921.) Immunoprecipitates were incubated with 1.4 μg (10,000 dpm) histones for 3 h at 37° C. HDAC activity was determined by scintillation counting of the ethyl acetate-soluble [$^3$H]acetic acid (as described in Taunton, et al., *Science* 1996, 272, 408-411). Compounds were added in DMSO such that final assay concentrations were 1% DMSO. IC50s were calculated using Prism 3.0 software. Curve fitting was done without constraints using the program's Sigmoidal-Dose Response parameters. All data points were acquired in duplicate and IC50s are calculated from the composite results of at least two separate experiments.

Example 3: In Vivo Activity

Although a variety of methods can be utilized, one exemplary method by which the in vivo activity of the inventive compounds is determined is by subcutaneously transplanting a desired tumor mass in mice. Drug treatment is then initiated when tumor mass reaches approximately 100 mm³ after transplantation of the tumor mass. A suitable composition, as described in more detail above, is then administered to the mice, preferably in saline and also preferably administered once a day at doses of 5, 10 and 25 mg/kg, although it will be appreciated that other doses can also be administered. Body weight and tumor size are then measured daily and changes in percent ratio to initial values are plotted. In cases where the transplanted tumor ulcerates, the weight loss exceeds 25-30% of control weight loss, the tumor weight reaches 10% of the body weight of the cancer-bearing mouse, or the cancer-bearing mouse is dying, the animal is sacrificed in accordance with guidelines for animal welfare.

Example 4: Assays to Identify Potential Antiprotozoal Compounds by Inhibition of Histone Deacetylase As detailed in U.S. Pat. No. 6,068,987, inhibitors of histone deacetylases may also be useful as antiprotozoal agents. Described therein are assays for histone deacetylase activity and inhibition and describe a variety of known protozoal diseases. The entire contents of 6,068,987 are hereby incorporated by reference.

The invention claimed is:

1. A method of treating a skin cancer selected from the group consisting of squamous cell carcinoma, basal cell carcinoma and malignant melanoma, in a patient suffering therefrom, said method comprising topically administering to the skin of the patient a compound of the formula (Ib):

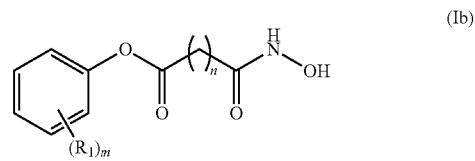

or a pharmaceutically acceptable salt thereof, wherein
n is 5, 6, or 7;
m is an integer from 1 to 5;
each $R_1$ is independently hydrogen; $OR_A$; —N($R_A$)$_2$; —NH$R_A$; substituted or unsubstituted acyl; —C(=O)O$R_A$; —C(=O)N($R_A$)$_2$; —CHO; or —NHC(=O)$R_A$; and
$R_A$ is independently hydrogen or $C_1$-$C_6$ alkyl.

2. The method of claim 1, wherein n is 6.
3. The method of claim 1, wherein m is 1.
4. The method of claim 1, wherein the compound is represented by the structural formula:

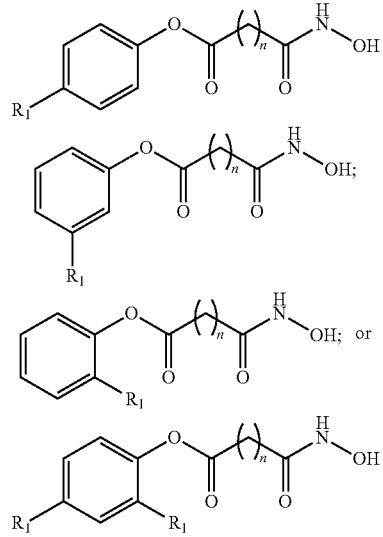

or a pharmaceutically acceptable salt thereof.

5. The method of claim 4, wherein n is 6.
6. The method of claim 4, wherein $R_1$ is —C(=O)O$R_A$; and $R_A$ is methyl, ethyl, n-propyl, isopropyl, n-butyl, sec-butyl, isobutyl, tert-butyl, n-pentyl, sec-pentyl, isopentyl, tert-pentyl, n-hexyl, or sec-hexyl.
7. The method of claim 6, wherein $R_A$ is methyl, ethyl, n-propyl, isopropyl, n-butyl, isobutyl, or tert-butyl.

8. The method of claim 7, wherein $R_A$ is methyl or ethyl.

9. The method of claim 7, wherein $R_A$ is tert-butyl.

10. The method of claim 1, wherein the skin cancer is basal cell carcinoma.

11. The method of claim 1, wherein the compound is of the formula

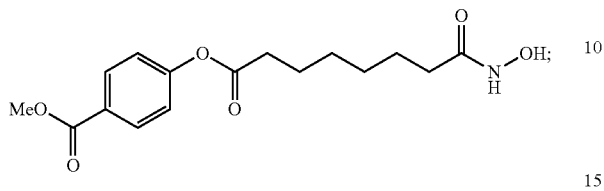

or a pharmaceutically acceptable salt thereof.

12. The method of claim 10, wherein the compound is of the formula

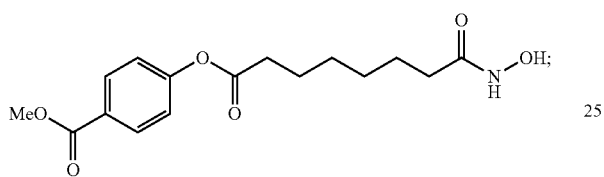

or a pharmaceutically acceptable salt thereof.

* * * * *